US008586041B2

(12) United States Patent
van de Winkel et al.

(10) Patent No.: US 8,586,041 B2
(45) Date of Patent: Nov. 19, 2013

(54) HUMAN MONOCLONAL ANTIBODIES TO EPIDERMAL GROWTH FACTOR RECEPTOR (EGFR)

(75) Inventors: Jan G. J. van de Winkel, Zeist (NL); Marcus Antonius van Dijk, Bilthoven (NL); Edward Halk, Sunnyvale, CA (US); Arnout F. Gerritsen, Bunnik (NL); Jorgen Petersen, Rungsted Kyst (DK); Ole Baadsgaard, Hellerup (DK)

(73) Assignee: Genmab A/S, Copenhagen (DK)

( * ) Notice: Subject to any disclaimer, the term of this patent is extended or adjusted under 35 U.S.C. 154(b) by 584 days.

(21) Appl. No.: 12/464,057

(22) Filed: May 11, 2009

(65) Prior Publication Data

US 2010/0008929 A1     Jan. 14, 2010

Related U.S. Application Data

(60) Division of application No. 10/320,094, filed on Dec. 16, 2002, now Pat. No. 7,595,378, which is a continuation-in-part of application No. 10/172,317, filed on Jun. 13, 2002, now Pat. No. 7,247,301.

(60) Provisional application No. 60/298,172, filed on Jun. 13, 2001.

(51) Int. Cl.
*A61K 39/395* (2006.01)
*C12P 21/08* (2006.01)
*C07K 16/28* (2006.01)

(52) U.S. Cl.
USPC ............... 424/142.1; 424/130.1; 424/133.1; 424/135.1; 424/136.1; 424/141.1; 424/143.1; 424/156.1; 424/178.1; 530/387.3; 530/388.1; 530/388.15; 530/388.22

(58) Field of Classification Search
None
See application file for complete search history.

(56) References Cited

U.S. PATENT DOCUMENTS

| | | | |
|---|---|---|---|
| 4,943,533 A | 7/1990 | Mendelsohn et al. | |
| 4,954,617 A | 9/1990 | Fanger et al. | |
| 5,218,090 A | 6/1993 | Connors | |
| 5,459,061 A | 10/1995 | Sato et al. | |
| 5,470,571 A | 11/1995 | Herlyn et al. | |
| 5,614,488 A | 3/1997 | Bacha | |
| 5,635,600 A * | 6/1997 | Fanger et al. | 530/387.3 |
| 5,643,759 A | 7/1997 | Pfreundschuh et al. | |
| 5,705,157 A | 1/1998 | Greene | |
| 5,708,156 A | 1/1998 | Ilekis | |
| 5,770,195 A | 6/1998 | Hudziak et al. | |
| 5,844,093 A | 12/1998 | Kettleborough et al. | |
| 5,874,299 A | 2/1999 | Lonberg et al. | |
| 5,906,820 A | 5/1999 | Bacha | |
| 6,217,866 B1 | 4/2001 | Schlessinger et al. | |
| 6,235,883 B1 * | 5/2001 | Jakobovits et al. | 530/388.22 |
| 6,309,636 B1 | 10/2001 | do Couto et al. | |
| 6,538,114 B1 | 3/2003 | Persson et al. | |
| 6,680,209 B1 | 1/2004 | Buechler et al. | |
| 7,060,808 B1 * | 6/2006 | Goldstein et al. | 536/23.1 |
| 2002/0004587 A1 | 1/2002 | Miller et al. | |

FOREIGN PATENT DOCUMENTS

| | | |
|---|---|---|
| EP | 0667165 B1 | 8/1995 |
| EP | 0706799 A2 | 4/1996 |
| EP | 1170011 A1 | 1/2002 |
| EP | 0586002 A2 | 3/2004 |
| EP | 0586002 B1 | 3/2004 |
| WO | WO-95/16037 A1 | 6/1995 |
| WO | WO-95/20045 | 7/1995 |
| WO | WO-98/50433 A2 | 11/1998 |
| WO | WO-98/50433 A3 | 11/1998 |
| WO | WO-00/37025 | 6/2000 |
| WO | WO-01/09187 A2 | 2/2001 |
| WO | WO-01/25492 A1 | 4/2001 |
| WO | WO-01/88138 A1 | 11/2001 |
| WO | WO-02/11677 A2 | 2/2002 |
| WO | WO-02/100348 A2 | 12/2002 |

OTHER PUBLICATIONS

Albanell, Joan, et al., "Activated Extracellular Signal-regulated Kinases: Association with Epidermal Growth Factor Receptor/Transforming Growth Factor α Expression in Head and Neck Squamous Carcinoma and Inhibition by Anti-Epidermal Growth Factor Receptor Treatments," *Cancer Research*, vol. 61:6500-6510 (2001).

Baselga, J., "The EGFR as a target for anticancer therapy—focus on cetuximab," *European Journal of Cancer*, vol. 37:S16-S22 (2001).

Baselga, José, "Monoclonal antibodies directed at growth factor receptors," *Ann. Oncol.*, vol. 11(Suppl. 3):187-190 (2000).

Baselga, José, "New Therapeutic Agents Targeting the Epidermal Growth Factor Receptor," *Journal of Clinical Oncology*, vol. 18(21s):54s-59s (2000).

Bastholt, L., et al., "A novel fully human monoclonal antibody against Epidermal Growth Factor Receptor (EGFR), First clinical and FDG-PET imaging results from a phase I/II trial conducted by the Danish Head and Neck Cancer Study Group (DAHANCA) in patients with squamous cell carcinoma of the head and neck (SCCHN)," found online at: http://meeting.jco.org/cgi/content/abstract/23/16_suppl/5530.

Bastholt, L., et al., "HuMax-EGFr, a Novel Fully Human Monoclonal Antibody against EGFr Safety and Pharmacokinetics in Patients with Squamous Cell Carcinoma of the Head and Neck (SCCHN)".

(Continued)

*Primary Examiner* — Xiaozhen Xie
(74) *Attorney, Agent, or Firm* — Nelson Mullins Riley & Scarborough LLP; Jane E. Remillard, Esq.; Jeanne M. DiGiorgio, Esq.

(57) ABSTRACT

Isolated human monoclonal antibodies which specifically bind to human EGFR, and related antibody-based compositions and molecules, are disclosed. The human antibodies can be produced by a transfectoma or in a non-human transgenic animal, e.g., a transgenic mouse, capable of producing multiple isotypes of human monoclonal antibodies by undergoing V-D-J recombination and isotype switching. Also disclosed are pharmaceutical compositions comprising the human antibodies, non-human transgenic animals and hybridomas which produce the human antibodies, and therapeutic and diagnostic methods for using the human antibodies.

23 Claims, 18 Drawing Sheets

(56) References Cited

OTHER PUBLICATIONS

Bier, Henning, et al., "Anti-(epidermal growth factor) receptor monoclonal antibodies for the induction of antibody-dependent cell-mediated cytotoxicity against squamous cell carcinoma lines of the head and neck," *Cancer Immunoll Immunother.*, vol. 46:167-173 (1998).

Bishop, Philippe C., et al., "Differential sensitivity of cancer cells to inhibitors of the epidermal growth factor receptor family," *Oncogene*, vol. 21:119-127 (2002).

Bleeker, Wim K. et al, "Dual Mode of Action of a Human Anti-Epidermal Growth Factor Receptor Monoclonal Antibody for Cancer Therapy," *The Journal of Immunology*, vol. 173:4699-4707 (2004).

Buchsbaum, Donald J. et al., "Treatment of Pancreatic Cancer Xenografts with Erbitux (IMC-C225) Anti-EGFR Antibody, Gemcitabine, and Radiation," Int. *J. Radiation Oncology Biol. Phys.*, vol. 54(4):1180-1193 (2002).

Bunn, Paul A., et al., "Epidermal Growth Factor Receptor Expression, Signal Pathway, and Inhibitors in Non-Small Cell Lung Cancer," *Seminars in Oncology*, vol. 29(5, Suppl. 4):38-44 (2002).

Cacia, J. et al., "Isomerization of an aspartic acid residue in the complementarity-determining regions of a recombinant antibody to human IgE: identification and effect on binding affinity," *Biochemistry*, vol. 35(6):1897-1903 (1996).

Chao, G. et al., "Fine epitope mapping of anti-epidermal growth factor receptor antibodies through random mutagenesis and yeast surface display," *J. Mol. Biol.*, vol. 342(2):539-550 (2004).

Ciardiello, Fortunato, et al., "Anti-epidermal growth factor receptor drugs in cancer therapy," *Expert Opin. Investig. Drugs*, vol. 11(6):755-768 (2002).

Ciardiello, Fortunato, et al., "A Novel Approach in the Treatment of Cancer: Targeting the Epidermal Growth Factor Receptor," *Clinical Cancer Research*, vol. 7:2958-2970 (2001).

Cochran, J.R. et al., "Domain-level antibody epitope mapping through yeast surface display of epidermal growth factor receptor fragments," *J. Immunol. Methods*, vol. 287(1-2):147-158 (2004).

Da Costa et al., "The role of the mouse macrophage scavenger receptor in myelin phagocytosis," *European Journal of Neuroscience*, vol. 9:2650-2657 (1997).

Elsasser, et al., "Preclinical studies combining bispecific antibodies with cytokine-stimulated effector cells for immunotherapy of renal cell carcinoma," Anticancer Research, vol. 19:1525-1528 (1999).

Fishwild, Dianne M. et al, "High-avidity human IgGκ monoclonal antibodies from a novel strain of minilocus transgenic mice," *Nature Biotechnology*, vol. 14:845-851 (1996).

Genmab, "Genmab Presents New Humax-CD20 and Humax-EFGr Pre-Clinical Data," *Genmab*, Release No. 4/2003.

Genmab, "Genmab's HuMax-EGFr Eradicates Tumors in Mouse Cancer Studies HuMax-EGFr Highly Effective," *.Genmab*, Release No. 21.

Genmab, "Genmab Announces Positive Phase I/II Humax™-EGFR Safety Data," *Genmab* Release No. 66/2004.

Genmab, "Genmab Announces Encouraging Efficacy Data from Humax-EGFR Phase I/II Trial in Head and Neck Cancer," *Genmab*, Release No. 74/2004.

Genmab, "Genmab Presents Additional Humax®-EGFR Phase I/II Efficacy Data at ASCO Conference," *Genmab*, Release No. 23/2005.

Gill, Gordon N. et al., "Monoclonal Anti-epidermal Growth Factor Receptor Antibodies Which Are Inhibitors of Epidermal Growth Factor Binding and Antagonists of Epidermal Growth Factor-stimulated Tyrosine Protein Kinase Activity," *The Journal of Biological Chemistry*, vol. 259(12):7755-7760 (1984).

Harlow, et al., Antibodies: a laboratory manual, Cold Spring Harbor Laboratory, New York, (1988).

Heitner, et al. "Selection of cell binding and internalizing epidermal growth factor receptor antibodies from a phage display library," J. Immunol. Methods., vol. 248(1-2):17-30 (2001).

Khuri, Fadlo R., et al., "Treatment of Patients with Recurrent or Metastatic Squamous Cell Carcinoma of the Head and Neck: Current Status and Future Directions," *Seminars in Oncology*, vol. 27(4, Suppl. 8):25-33 (2000).

Lammerts van Bueren, Jeroen J. et al., "The antibody zalutumumab inhibits epidermal growth factor receptor signaling by limiting intra- and intermolecular flexibility," *PNAS*, vol. 105(16):6109-6114 (2008).

Masui, et al. "Growth inhibition of human tumor cells in athymic mice by anti-epidermal growth factor receptor monoclonal antibodies," Cancer Res., vol. 44(3):1002-7 (1984).

Mendelsohn, John, et al., "The EGF receptor family as targets for cancer therapy," *Oncogene*, vol. 19:6550-6565 (2000).

Modjtahedi, H. et al., "The receptor for EGF and its ligands: Expression, prognostic value and target for therapy in cancer (Review)," International Journal of Oncology, vol. 4:277-296 (1994).

Rudikoff, Stuart et al., "Single amino acid substitution altering antigen-binding specificity," *Proc. Natl. Acad. Sci. USA*, vol. 79:1979-1983 (1982).

Sato, J. Denry et al., "Biological Effects in Vitro of Monoclonal Antibodies to Human Epidermal Growth Factor Receptors," *Mol. Biol. Med.*, vol. 1:511-529 (1983).

Stadick, et al., "Epidermal growth factor receptor and G250: Useful target antigens for antibody mediated cellular cytotoxicity against renal cell carcinoma?" The Journal of Urology, vol. 167:707-712 (2002).

van Bueren, J.J., L., et al., "Impact of receptor-mediated antibody internationalization on the dose-effect relationship of a therapeutic mAb against EGFR," *Joint Annual Meeting of the German and Dutch Societies for Immunology (JAMI) / Immunology*, vol. 209:367-368 (2004).

Van Spriel, et al. "Immunotherapeutic perspective for bispecific antibodies," Immunology Today, vol. 21:8: 391-97 (2000).

van Zoelen, E.J.J., et al., "Rational Design for the Development of Epidermal Growth Factor Receptor Antagonists," *Path. Res. Pract.*, vol. 192:761-767 (1996).

Wang, X. et al. "Epidermal growth factor receptor is a cellular receptor for human cytomegalovirus." *Nature*, vol. 424(6947):456-61 (2003).

Wang et al. "Human Cytomegalovirus Receptor: HCMV Infection of HEL Cell is EGF Receptor Dependent," Poster Presentation at 26th International Herpes Workshop, Jul. 28-Aug. 3, 2001 Germany.

Wang et al. "Receptor for Human Cytomegalovirus: HCMV Infection of HEL and HUVE Cells is EGF Receptor Dependent," Poster Presentation at 26th International Herpes Workshop, Jul. 28-Aug. 3, 2001, Germany.

Yang, Xiao-Dong, et al., "Development of ABX-EGF, a fully human anti-EGF receptor monoclonal antibody, for cancer therapy," *Critical Reviews in Oncology/Hematology*, vol. 38:17-23 (2001).

Yang, Xiao-Dong et al., "Eradication of Established Tumors by a Fully Human Monoclonal Antibody to the Epidermal Growth Factor Receptor without Concomitant Chemotherapy," *Cancer Research*, vol. 59:1236-1243 (1999).

Supplementary Partial European Search Report Application No. 03808487.7, dated Jan. 5, 2006.

European Search Report for Application No. 03808487.7, dated Apr. 28, 2006.

Beers, Richard et al., "Immunotoxins with Increased Activity against Epidermal Growth Factor Receptor vIII-expressing Cells Produced by Antibody Phage Display," Clinical Cancer Research, vol. 6:2835-2843 (2000).

Mendez, Michael J. et al., "Functional transplant of megabase human immunoglobulin loci recapitulates human antibody response in mice," Nat. Genet, vol. 15(2):146-156 (1997).

Wallace, Paul K. et al., "Production of macrophage-activated killer cells for targeting of glioblastoma cells with bispecific antibody to FcgammaRI and the epidermal growth factor receptor," Cancer Immunol. Immunother., vol. 49 (9):493-503 (2000).

\* cited by examiner

```
Anti-EGFR 2F8 VL
    V-segment:      L18
    J segment:      JK4

A   I   Q   L   T   Q   S   P   S   S   L   S   A   S   V   G   D   R
1     GCC ATC CAG TTG ACC CAG TCT CCA TCC TCC CTG TCT GCA TCT GTA GGA GAC AGA

CDR1
                                        ------------------------------------------------
      V   T   I   T   C   R   A   S   Q   D   I   S   S   A   L   V   W   Y
55    GTC ACC ATC ACT TGC CGG GCA AGT CAG GAC ATT AGC AGT GCT TTA GTC TGG TAT

CDR2
                                                      ------------------------
      Q   Q   K   P   G   K   A   P   K   L   L   I   Y   D   A   S   S   L
109   CAG CAG AAA CCA GGG AAA GCT CCT AAG CTC CTG ATC TAT GAT GCC TCC AGT TTG

CDR2
      --------
      E   S   G   V   P   S   R   F   S   G   S   E   S   G   T   D   F   T
163   GAA AGT GGG GTC CCA TCA AGG TTC AGC GGC AGT GAA TCT GGG ACA GAT TTC ACT

CDR3
                                                                        --------
      L   T   I   S   S   L   Q   P   E   D   F   A   T   Y   Y   C   Q   Q
217   CTC ACC ATC AGC AGC CTG CAG CCT GAA GAT TTT GCA ACT TAT TAC TGT CAA CAG

CDR3
      ----------------------------------
      F   N   S   Y   P   L   T   F   G   G   G   T   K   V   E   I   K
271   TTT AAT AGT TAC CCG CTC ACT TTC GGC GGA GGG ACC AAG GTG GAG ATC AAA
```

Fig. 15A

```
Anti-EGFR 2F8 VH
    V-segment:    VH3-33
    D segment:    D3-10
    J segment:    JH4b Q   V   Q   L   V   E   S   G   G   V   V   Q   P   G   R   S   L
  1     CAG GTG CAG CTG GTG GAG TCT GGG GGA GGC GTG GTC CAG CCT GGG AGG TCC CTG CDR1
                                                ~~~~~~~~~~~~~~~~~~~~~
        R   L   S   C   A   A   S   G   F   T   F   S   T   Y   G   M   H   W
 55     AGA CTC TCC TGT GCA GCG TCT GGA TTC ACC TTC AGT ACC TAT GGC ATG CAC TGG CDR2
                                                ~~~~~~~~~~~~~~~~~~~~
        V   R   Q   A   P   G   K   G   L   E   W   V   A   V   I   W   D   D
109     GTC CGC CAG GCT CCA GGC AAG GGG CTG GAG TGG GTG GCA GTT ATA TGG GAT GAT CDR2
        ~~~~~~~~~~~~~~~~~~~~~~~~~~~~~~~~~~~~~~~~~~~~~~~~
        G   S   Y   K   Y   Y   G   D   S   V   K   G   R   F   T   I   S   R
163     GGA AGT TAT AAA TAC TAT GGA GAC TCC GTG AAG GGC CGA TTC ACC ATC TCC AGA D   N   S   K   N   T   L   Y   L   Q   M   N   S   L   R   A   E   D
217     GAC AAT TCC AAG AAC ACG CTG TAT CTG CAA ATG AAC AGC CTG AGA GCC GAG GAC CDR3
                                                ~~~~~~~~~~~~~~~~~~~~~~~~~~~~~
        T   A   V   Y   Y   C   A   R   D   G   I   T   M   V   R   G   V   M
271     ACG GCT GTG TAT TAC TGT GCG AGA GAT GGT ATT ACT ATG GTT CGG GGA GTT ATG CDR3
        ~~~~~~~~~~~~~~~~~~~~~~~~~~
        K   D   Y   F   D   Y   W   G   Q   G   T   L   V   T   V   S   S
325     AAG GAC TAC TTT GAC TAC TGG GGC CAG GGA ACC CTG GTC ACC GTC TCC TCA
```

Fig. 15B

SEQUENCE LISTING

```
<160> NUMBER OF SEQ ID NOS: 12

<210> SEQ ID NO 1
<211> LENGTH: 375
<212> TYPE: DNA
<213> ORGANISM: Homo sapiens

<400> SEQUENCE: 1
caggtgcagc tggtggagtc tggggggaggc gtggtccagc ctgggaggtc cctgagactc      60
tcctgtgcag cgtctggatt caccttcagt acctatggca tgcactgggt ccgccaggct     120
ccaggcaagg ggctggagtg ggtggcagtt atatgggatg atggaagtta taaatactat     180
```

```
ggagactccg tgaagggccg attcaccatc tccagagaca attccaagaa cacgctgtat    240
ctgcaaatga acagcctgag agccgaggac acggctgtgt attactgtgc gagagatggt    300
attactatgg ttcggggagt tatgaaggac tactttgact actggggcca gggaaccctg    360
gtcaccgtct cctca                                                     375
```

<210> SEQ ID NO 2
<211> LENGTH: 125
<212> TYPE: PRT
<213> ORGANISM: Homo sapiens

<400> SEQUENCE: 2

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Thr Tyr
                20                  25                  30

Gly Met His Trp Val Arg Gln Ala Pro Gly Lys Gly Leu Glu Trp Val
            35                  40                  45

Ala Val Ile Trp Asp Asp Gly Ser Tyr Lys Tyr Tyr Gly Asp Ser Val
        50                  55                  60

Lys Gly Arg Phe Thr Ile Ser Arg Asp Asn Ser Lys Asn Thr Leu Tyr
 65                 70                  75                  80

Leu Gln Met Asn Ser Leu Arg Ala Glu Asp Thr Ala Val Tyr Tyr Cys
                85                  90                  95

Ala Arg Asp Gly Ile Thr Met Val Arg Gly Val Met Lys Asp Tyr Phe
            100                 105                 110

Asp Tyr Trp Gly Gln Gly Thr Leu Val Thr Val Ser Ser
        115                 120                 125
```

<210> SEQ ID NO 3
<211> LENGTH: 321
<212> TYPE: DNA
<213> ORGANISM: Homo sapiens

<400> SEQUENCE: 3

```
gccatccagt tgacccagtc tccatcctcc ctgtctgcat ctgtaggaga cagagtcacc     60
atcacttgcc gggcaagtca ggacattagc agtgctttag tctggtatca gcagaaacca    120
gggaaagctc ctaagctcct gatctatgat gcctccagtt tggaaagtgg ggtcccatca    180
aggttcagcg gcagtgaatc tgggacagat ttcactctca ccatcagcag cctgcagcct    240
gaagattttg caacttatta ctgtcaacag tttaatagtt acccgctcac tttcggcgga    300
gggaccaagg tggagatcaa a                                              321
```

<210> SEQ ID NO 4
<211> LENGTH: 107
<212> TYPE: PRT
<213> ORGANISM: Homo sapiens

<400> SEQUENCE: 4

```
Ala Ile Gln Leu Thr Gln Ser Pro Ser Ser Leu Ser Ala Ser Val Gly
 1               5                  10                  15

Asp Arg Val Thr Ile Thr Cys Arg Ala Ser Gln Asp Ile Ser Ser Ala
                20                  25                  30

Leu Val Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
        50                  55                  60
```

```
Ser Glu Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Asn Ser Tyr Pro Leu
                 85                  90                  95

Thr Phe Gly Gly Gly Thr Lys Val Glu Ile Lys
            100                 105

<210> SEQ ID NO 5
<211> LENGTH: 5
<212> TYPE: PRT
<213> ORGANISM: Homo sapiens

<400> SEQUENCE: 5

Thr Tyr Gly Met His
 1               5

<210> SEQ ID NO 6
<211> LENGTH: 17
<212> TYPE: PRT
<213> ORGANISM: Homo sapiens

<400> SEQUENCE: 6

Val Ile Trp Asp Asp Gly Ser Tyr Lys Tyr Tyr Gly Asp Ser Val Lys
 1               5                  10                  15

Gly

<210> SEQ ID NO 7
<211> LENGTH: 16
<212> TYPE: PRT
<213> ORGANISM: Homo sapiens

<400> SEQUENCE: 7

Asp Gly Ile Thr Met Val Arg Gly Val Met Lys Asp Tyr Phe Asp Tyr
 1               5                  10                  15

<210> SEQ ID NO 8
<211> LENGTH: 11
<212> TYPE: PRT
<213> ORGANISM: Homo sapiens

<400> SEQUENCE: 8

Arg Ala Ser Gln Asp Ile Ser Ser Ala Leu Val
 1               5                  10

<210> SEQ ID NO 9
<211> LENGTH: 7
<212> TYPE: PRT
<213> ORGANISM: Homo sapiens

<400> SEQUENCE: 9

Asp Ala Ser Ser Leu Glu Ser
 1               5

<210> SEQ ID NO 10
<211> LENGTH: 9
<212> TYPE: PRT
<213> ORGANISM: Homo sapiens

<400> SEQUENCE: 10

Gln Gln Phe Asn Ser Tyr Pro Leu Thr
 1               5

<210> SEQ ID NO 11
<211> LENGTH: 1394
```

<212> TYPE: DNA
<213> ORGANISM: Homo sapiens

<400> SEQUENCE: 11

```
ctgcagctgt gtccagcctg cccatcctct gctcatttgc atattcccag aacacaacct      60
cctgccctga agacttctta ataggctggt cacacttctt gcaggagtca gacccactca     120
ggacacagca tggacatgag ggtccccgct cagctcctgg ggcttctgct gctctggctc     180
ccaggtaagg aaggagaaca ctaacagttt actcagccca gggggctcag tacagcctgg     240
ctattcaggg aaattctctt actacatgat taattgtgtg gaccatttgt gtttatgctt     300
ccaatctcag gtgccagatg tgccatccag ttgacccagt ctccatcctc cctgtctgca     360
tctgtaggag acagagtcac catcacttgc cgggcaagtc agggcattag cagtgcttta     420
gcctggtatc agcagaaacc agggaaagct cctaagctcc tgatctatga tgcctccagt     480
ttggaaagtg ggtcccatc aaggttcagc ggcagtggat ctgggacaga tttcactctc     540
accatcagca gcctgcagcc tgaagatttt gcaacttatt actgtcaaca gtttaataat     600
taccctcaca tagtgttaca aacccgaaca taaaccccca gggaagcaga tgtgtgagac     660
tgggctgccc cagctgcttc tcctgatgcc tccattggct gagagtgttc ctcagatgca     720
gccacactct gatggtgttg gtagaggagg atatgagatc acctctgcat cccaatttct     780
ttttcttttc tcagccccag ctgcacagac ataacaatgc ctctgctgat ttaataaaga     840
tagagatcat gacacctgaa gagtctagtt tatggctttg gttagaattc atataacaga     900
gaagaagcca ttatagatat tctaagcagg aatagtctta atagatagaa ttagagtcta     960
aagtattgaa gtctaaataa aatgtacaga taaatttagt gttttatttg ctaagaaatt    1020
tttgccaaat ggggcataca ggaaaactca atggtcttca atatgttgga agagcaaaga    1080
gttttataaa aagggaaatt attacctatt gttctttgag aaattttgtt ggctgtagta    1140
agggttggga gctggcaagc tcagactggt aagcagtggg ggtcaaactg aatcctagaa    1200
ttatattaag ttatctcaga agttgtgggt aaatttgctt tcaggttaca ataagccaaa    1260
gcagtgaagc ttgcagagaa ttttgttact gaaatgccag ggattcagta tagatcctgc    1320
ggctcaccac acagaaagcc aatcactaag acaacaagtg ttgtcaaaga acaggcttta    1380
atcaggtgct gcag                                                      1394
```

<210> SEQ ID NO 12
<211> LENGTH: 296
<212> TYPE: DNA
<213> ORGANISM: Homo sapiens

<400> SEQUENCE: 12

```
caggtgcagc tggtggagtc tgggggaggc gtggtccagc ctgggaggtc cctgagactc      60
tcctgtgcag cgtctggatt caccttcagt agctatggca tgcactgggt ccgccaggct     120
ccaggcaagg ggctggagtg gtggcagtt atatggtatg atggaagtaa taaatactat     180
gcagactccg tgaagggccg attcaccatc tccagagaca attccaagaa cacgctgtat     240
ctgcaaatga acagcctgag agccgaggac acggctgtgt attactgtgc gagaga         296
```

HUMAN MONOCLONAL ANTIBODIES TO EPIDERMAL GROWTH FACTOR RECEPTOR (EGFR)

RELATED APPLICATIONS

This application is a divisional of U.S. patent application Ser. No. 10/320,094 filed on Dec. 16, 2002, issued on Sep. 29, 2009 as U.S. Pat. No. 7,595,378, which is a continuation-in-part of U.S. patent application Ser. No. 10/172,317 (filed on Jun. 13, 2002, issued on Jul. 24, 2007 as U.S. Pat. No. 7,247, 301, which claims priority to U.S. Provisional Patent Application No. 60/298,172, filed on Jun. 13, 2001, the contents of which are incorporated herein in their entirety by this reference.

BACKGROUND OF THE INVENTION

The EGF receptor (EGFR) is a 170 kDa type 1 transmembrane molecule. Its expression is found to be upregulated in many human tumors including carcinoma of the head and neck, breast, colon, prostate, lung, and ovaries. The degree of over-expression is correlated to poor clinical prognosis (Baselga, et al. (1994) Pharmac. Therapeut. 64:127-154; Modjtahedi, et al. (1994) Int. J. Oncology 4:277-296). Furthermore, its expression is frequently accompanied by the production of EGFR-ligands, TGF-α and EGF among others, by EGFR-expressing tumor cells which suggests that an autocrine loop participates in the progression of these cells (Baselga, et al. (1994) Pharmac. Therapeut. 64:127-154; Modjtahedi, et al. (1994) Int. J. Oncology. 4:277-296). Blocking the interaction between such EGFR ligands and EGFR therefore can inhibit tumor growth and survival (Baselga, et al. (1994) Pharmac. Therapeut. 64:127-154).

Monoclonal antibodies (MAbs) directed to the ligand-binding domain of EGFR can block the interaction with EGF and TGF-α and, concomitantly, the resultant intracellular signaling pathway. Several murine monoclonal antibodies have been generated which achieve such a block in vitro and which have been evaluated for their ability to affect tumor growth in mouse xenograft models (Masui, et al. (1986) Cancer Res. 46: 5592-5598; Masui, et al. (1984) Cancer Res. 44: 1002-1007; Goldstein, et al. (1995) Clin. Cancer Res. 1: 1311-1318). When administered one day after the human tumor cells, most of the anti-EGFR MAbs were efficacious in preventing tumor formation in athymic mice (Baselga, et al. (1994) Pharmac. Therapeut. 64:127-154). However, when injected into mice bearing established human tumor xenografts, these murine MAbs (e.g., MAbs 225s and 528) caused only partial tumor regression. Co-administration of chemotherapeutic agents was needed to fully eradicate the tumors (Baselga, et al. (1994) Pharmac. Therapeut. 64:127-154; Fan, et al. (1993) Cancer Res. 53: 4322-4328; Baselga, et al. (1993) J. Natl. Cancer Inst. 85: 1327-1333).

Therefore, while the results obtained to date clearly establish EGFR as a target for immunotherapy, they also show that murine antibodies do not constitute ideal therapeutic agents. Moreover, treatment with murine antibodies generally triggers severe immune reactions in patients. To circumvent the immunogenicity of mouse antibodies, therapeutics should ideally be fully human. As a step towards this goal, a chimeric version of the 225 MAb (C225), in which the mouse antibody variable regions are linked to human constant regions, has been developed. While C225 exhibited an improved anti-tumor activity in the treatment of established xenograft tumors in vivo, this was only achieved at high doses (Goldstein, et al. (1995) Clin. Cancer Res. 1:1311-1318). Currently C225 is being evaluated in clinical trials for treatment of various types of solid tumors (Baselga, J. (2000) J. Clin. Oncol. 18: 54S-59S; Baselga, J. (2000) Ann. Oncol. 11 Suppl 3: 187-190, 2000).

Accordingly, the need exists for improved therapeutic antibodies against EGFR which are effective at treating and/or preventing diseases related to overexpression of EGFR when administered at low dosages, and which do not elicit immune reactions in patients. As described above, monoclonal antibodies (MAb) play a prominent role in many diagnostic and therapeutic approaches to diseases and have become even more attractive agents with the recent advent of technologies that allow development of fully human antibodies. Antibodies and antibody derivatives constitute twenty five percent of biological drugs currently under development and many of these are being developed as cancer therapeutics. Antibodies combine target specificity with the capacity to effectively engage the immune system. The combination of these properties and their long biological half-life alerted researchers to the therapeutic potential of antibodies. This has recently culminated in the U.S. Food and Drug Administration (FDA) approval of several antibodies for cancer treatment.

SUMMARY OF THE INVENTION

The present invention provides improved antibody therapeutics for treating and preventing diseases related to expression of EGFR, particularly EGFR-expressing tumors and autoimmune diseases. The antibodies are improved in that they are fully human (referred to herein as "HuMAbS™") and, thus, are less immunogenic in patients. The antibodies are also therapeutically effective (e.g., at preventing growth and/or function of EGFR-expressing cells) at lower dosages than previously reported for other anti-EGFR antibodies. In addition, in certain embodiments, the antibodies have the added benefit of not activating complement (e.g., not inducing complement mediated lysis of target cells) which reduces adverse side-effects during treatment.

Accordingly, in one embodiment, the present invention provides isolated human monoclonal antibodies which specifically bind to human epidermal growth factor receptor (EGFR), as well as compositions containing one or a combination of such antibodies. The human antibodies inhibit (e.g., block) binding of EGFR ligands, such as EGF and TGF-α, to EGFR. For example, binding of EGFR ligand to EGFR can be inhibited by at least about 10%, 20%, 30%, 40%, 50%, 60%, 70%, 80%, 90%, or 100% and preferably results in the prevention of EGFR-mediated cell signaling.

Preferred human antibodies of the invention inhibit the growth and/or mediate the killing (e.g., lysis or phagocytosis) of cells expressing EGFR (in vitro or in vivo) in the presence of human effector cells (e.g., polymorphonuclear cells, monocytes, macrophages and dendritic cells), yet they do not activate complement mediated lysis of cells which express EGFR. Accordingly, human monoclonal antibodies of the invention can be used as diagnostic or therapeutic agents in vivo and in vitro.

In one embodiment exemplified herein, human antibodies of the invention are IgG1 (e.g., IgG1k) antibodies having an IgG1 heavy chain and a kappa light chain. However, other antibody isotypes are also encompassed by the invention, including IgG2, IgG3, IgG4, IgM, IgA1, IgA2, IgAsec, IgD, and IgE. The antibodies can be whole antibodies or antigen-binding fragments of the antibodies, including Fab, $F(ab')_2$, Fv and chain Fv fragments.

In another aspect, the invention relates to an isolated human monoclonal antibody which binds to human EGFR, wherein the antibody is an IgG1,κ or IgG1,λ isotype.

In another aspect, the invention relates to an isolated human monoclonal antibody which binds to human EGFR, wherein the antibody is an IgG4 antibody.

In another aspect, the invention relates to an isolated human monoclonal antibody which binds to human EGFR, wherein the antibody is an IgG4,κ or IgG4,λ isotype.

In another aspect, the invention relates to an isolated human monoclonal antibody which binds to human EGFR, wherein the antibody is selected from the group consisting of IgG1, IgA, IgE, IgM, IgG4, and IgD antibodies, and wherein the antibody comprises a variable heavy chain amino acid sequence as set forth in SEQ ID NO:2.

In another aspect, the invention relates to an isolated human monoclonal antibody which binds to human EGFR, wherein the antibody is selected from the group consisting of IgG1, IgA, IgE, IgM, IgG4, and IgD antibodies, and wherein the antibody comprises a variable heavy chain amino acid sequence which is at least 90% homologous, preferably at least 95% homologous, and more preferably at least 98%, or at least 99% homologous to the amino acid sequence as set forth in SEQ ID NO:2.

In another aspect, the invention relates to an isolated human monoclonal antibody which binds to human EGFR, wherein the antibody is selected from the group consisting of IgG1, IgA, IgE, IgM, IgG4, and IgD antibodies, and wherein the antibody comprises a variable light chain amino acid sequence as set forth in SEQ ID NO:4.

In another aspect, the invention relates to an isolated human monoclonal antibody which binds to human EGFR, wherein the antibody is selected from the group consisting of IgG1, IgA, IgE, IgM, IgG4, and IgD antibodies, and wherein the antibody comprises a variable light chain amino acid sequence which is at least 90% homologous, preferably at least 95% homologous, and more preferably at least 98%, or at least 99% homologous to the amino acid sequence as set forth in SEQ ID NO:4.

In another aspect, the invention relates to an isolated human monoclonal antibody which binds to human EGFR, wherein the antibody is selected from the group consisting of IgG1, IgA, IgE, IgM, IgG4, and IgD antibodies, and wherein the antibody comprises human heavy chain and human kappa light chain variable regions which are at least 90% homologous, preferably at least 95% homologous, and more preferably at least 98%, or at least 99% homologous to the amino acid sequences as set forth in SEQ ID NO:2 and SEQ ID NO:4, respectively.

In another aspect, the invention relates to an isolated human monoclonal antibody which binds to human EGFR, wherein the antibody is selected from the group consisting of IgG1, IgA, IgE, IgM, IgG4, and IgD antibodies, and wherein the antibody comprises at least one CDR sequence selected from the group consisting of:
(i) the CDR1, CDR2, and CDR3 regions shown in FIG. 15 (SEQ ID NOs:5, 6, 7, 8, 9, and 10);
(ii) sequences which are at least 90% homologous, preferably at least 95% homologous, and more preferably at least 98%, or at least 99% homologous to the sequences defined in (i); and
(iii) fragments of any one of the sequences defined in (i) or (ii), which retain the ability to bind to human EGFR.

In another aspect, the invention relates to an isolated human monoclonal antibody which binds to human EGFR, wherein the antibody is selected from the group consisting of IgG1, IgA, IgE, IgM, IgG4, and IgD antibodies, and wherein the antibody comprises the heavy chain CDR3 region shown in FIG. 15 (SEQ ID NO:7), a sequence which is at least 90% homologous, preferably at least 95% homologous, and more preferably at least 98%, or at least 99% homologous to SEQ ID NO:7, or a fragment thereof, which retains the ability to bind to human EGFR.

In another aspect the invention relates to an isolated human monoclonal antibody which binds to human EGFR, wherein the antibody is selected from the group consisting of IgG1, IgA, IgE, IgM, IgG4, and IgD antibodies, and wherein the antibody comprises at least four CDRs selected from (i) the CDR regions shown in FIG. 15 (SEQ ID NOs:5, 6, 7, 8, 9, or 10); (ii) sequences which are at least 90% homologous, preferably at least 95% homologous, and more preferably at least 98%, or at least 99% homologous to the sequences defined in (i); and (iii) fragments of the sequences defined in (i) or (ii), which retain the ability to bind to human EGFR.

In another aspect the invention relates to an isolated human monoclonal antibody which binds to human EGFR, wherein the antibody is selected from the group consisting of IgG1, IgA, IgE, IgM, IgG4, and IgD antibodies, and wherein the antibody comprises (i) the 6 CDR regions shown in FIG. 15 (SEQ ID NOs:5, 6, 7, 8, 9, and 10); (ii) sequences which are at least 90% homologous, preferably at least 95% homologous, and more preferably at least 98%, or at least 99% homologous to the sequences defined in (i); or (iii) fragments of the sequences defined in (i) or (ii), which retain the ability to bind to human EGFR.

In another aspect, the invention relates to an isolated human monoclonal antibody which binds to human EGFR, wherein the antibody is an intact antibody selected from the group consisting of an intact IgG1 antibody, an intact IgG4 antibody, an intact IgM antibody, an intact IgA1 antibody, an intact IgA2 antibody, an intact secretory IgA antibody, an intact IgD antibody, and an intact IgE antibody, wherein the antibody is glycosylated in a eukaryotic cell.

In another aspect, the invention relates to an isolated human monoclonal antibody which binds to human EGFR, wherein the antibody is an intact antibody selected from the group consisting of an intact IgG1,κ antibody, an intact IgG1,λ antibody, an intact IgG4,κ antibody, and an intact IgG4,λ antibody, wherein the antibody is glycosylated in a eukaryotic cell.

In another aspect, the invention relates to an isolated human monoclonal antibody which binds to human EGFR, wherein the antibody is selected from the group consisting of IgG1, IgA, IgE, IgM, IgG4, and IgD antibodies, and wherein the antibody comprises a heavy chain variable region amino acid sequence derived from a human $V_H$3-33 germline sequence (SEQ ID NO:12) and a light chain variable region amino acid sequence derived from a human VκL18 germline sequence (SEQ ID NO:11).

In a particular embodiment, the human antibody is encoded by human IgG heavy chain and human kappa light chain nucleic acids comprising nucleotide sequences in their variable regions as set forth in SEQ ID NO: 1 and SEQ ID NO:3, respectively, and conservative sequence modifications thereof. In another embodiment, the human antibody include IgG heavy chain and kappa light chain variable regions which comprise the amino acid sequences shown in SEQ ID NO:2 and SEQ ID NO:4, respectively, and conservative sequence modifications thereof.

In another particular embodiment, the human antibody corresponds to antibody 2F8 or an antibody that binds to the same epitope as (e.g., competes with) or has the same functional binding characteristics as antibody 2F8.

Human antibodies of the invention can be produced recombinantly in a host cell, such as a transfectoma (e.g., a transfectoma consisting of immortalized CHO cells or lymphocytic cells) containing nucleic acids encoding the heavy and light chains of the antibody, or be obtained directly from a hybridoma which expresses the antibody (e.g., which includes a B cell obtained from a transgenic non-human animal, e.g., a transgenic mouse, having a genome comprising a human heavy chain transgene and a human light chain transgene that encode the antibody, fused to an immortalized cell). In a particular embodiment, the antibodies are produced by a hybridoma referred to herein as 2F8 or by a host cell (e.g., a CHO cell) transfectoma containing human heavy chain and human light chain nucleic acids which comprise nucleotide sequences in their variable regions as set forth in SEQ ID NOs:1 and 3, respectively, and conservative modifications thereof.

In another embodiment, human anti-EGFR antibodies of the present invention can be characterized by one or more of the following properties:

a) specificity for the EGFR;

b) a binding affinity to EGFR with an equilibrium association constant ($K_A$) of at least about $10^7$ $M^{-1}$, preferably about, $10^8$ $M^{-1}$, $10^9$ $M^{-1}$, and more preferably, about $10^{10}$ $M^{-1}$ to $10^{11}$ $M^{-1}$ or higher;

c) a dissociation constant ($K_D$) from EGFR of about $10^{-3}$ $s^{-1}$, preferably about $10^{-4}$ $s^{-1}$, more preferably, $10^{-5}$ $s^{-1}$, and most preferably, $10^{-6}$ $s^{-1}$;

d) the ability to opsonize a cell expressing EGFR; or e) the ability to inhibit growth and/or mediate phagocytosis and killing of cells expressing EGFR (e.g., a tumor cell) in the presence of human effector cells at a concentration of about 10 µg/ml or less (e.g., in vitro).

Examples of EGFR-expressing tumor cells which can be targeted (e.g., opsonized) by human antibodies of the present invention include, but are not limited to, bladder, breast, colon, kidney, ovarian, prostate, renal cell, squamous cell, lung (non-small cell), or head and neck tumor cells. Other EGFR-expressing cells include synovial fibroblast cells and keratinocytes which can be used, for example, as target cells in the treatment of arthritis and psoriasis, respectively.

In another embodiment, human antibodies of the invention bind to EGFR antigen with an affinity constant of at least about $10^8$ $M^{-1}$, more preferably at least about $10^9$ $M^{-1}$ or $10^{10}$ $M^{-1}$, and are capable of inhibiting growth and/or mediating phagocytosis and killing of cells expressing EGFR by human effector cells, e.g., polymorphonuclear cells (PMNs), monocytes and macrophages, with an $IC_{50}$ of about $1 \times 10^{-7}$ M or less, or at a concentration of about 10 µg/ml or less in vitro.

In yet another embodiment, human antibodies of the invention inhibit EGFR-mediated cell signaling. For example, the antibodies can inhibit EGFR ligand (e.g., EGF or TGF-α) induced autophosphorylation of EGFR. The antibodies also can inhibit autocrine EGF or TGF-α induced cell activation or by inducing lysis (ADCC) of EGFR expressing cells in the presence of human polymorphonuclear cells. Cells which express EGFR include, among others, a bladder cell, a breast cell, a colon cell, a kidney cell, an ovarian cell, a prostate cell, a renal cell, a squamous cell, a non-small lung cell, a synovial fibroblast cell, and a keratinocyte.

In another aspect, the present invention provides nucleic acid molecules encoding the antibodies, or antigen-binding portions, of the invention. Recombinant expression vectors which include nucleic acids encoding antibodies of the invention, and host cells transfected with such vectors, are also encompassed by the invention, as are methods of making the antibodies of the invention by culturing such host cells, e.g., an expression vector comprising a nucleotide sequence encoding the variable and constant regions of the heavy and light chains of antibody 2F8 produced by the hybridoma.

In yet another aspect, the invention provides isolated B-cells from a transgenic non-human animal, e.g., a transgenic mouse, which express human anti-EGFR antibodies of the invention. Preferably, the isolated B cells are obtained from a transgenic non-human animal, e.g., a transgenic mouse, which has been immunized with a purified or enriched preparation of EGFR antigen and/or cells expressing the EGFR. Preferably, the transgenic non-human animal, e.g., a transgenic mouse, has a genome comprising a human heavy chain transgene and a human light chain transgene encoding all or a portion of an antibody of the invention. The isolated B-cells are then immortalized to provide a source (e.g., a hybridoma) of human anti-EGFR antibodies.

Accordingly, the present invention also provides a hybridoma capable of producing human monoclonal antibodies of the invention that specifically bind to EGFR. In one embodiment, the hybridoma includes a B cell obtained from a transgenic non-human animal, e.g., a transgenic mouse having a genome comprising a human heavy chain transgene and a human light chain transgene encoding all or a portion of an antibody of the invention, fused to an immortalized cell. Particular hybridomas of the invention include 2F8.

In another aspect the invention relates to a hybridoma comprising a B cell obtained from a transgenic nonhuman animal in which V-(D)-J gene segment rearrangements have resulted in the formation of a functional human heavy chain transgene and a functional light chain transgene fused to an immortalized cell, wherein the hybridoma produces a detectable amount of the monoclonal antibody of the invention as defined in any of the claims or embodiments herein.

In another aspect the invention relates to a transfectoma comprising nucleic acids encoding a human heavy chain and a human light chain, wherein the transfectoma produces a detectable amount of the monoclonal antibody of the invention as defined in any of the claims or embodiments herein.

In yet another aspect, the invention provides a transgenic non-human animal, such as a transgenic mouse (also referred to herein as a "HuMAb"), which express human monoclonal antibodies that specifically bind to EGFR. In a particular embodiment, the transgenic non-human animal is a transgenic mouse having a genome comprising a human heavy chain transgene and a human light chain transgene encoding all or a portion of an antibody of the invention. The transgenic non-human animal can be immunized with a purified or enriched preparation of EGFR antigen and/or cells expressing EGFR. Preferably, the transgenic non-human animal, e.g., the transgenic mouse, is capable of producing multiple isotypes of human monoclonal antibodies to EGFR (e.g., IgG, IgA and/or IgM) by undergoing V-D-J recombination and isotype switching. Isotype switching may occur by, e.g., classical or non-classical isotype switching.

In another aspect, the present invention provides methods for producing human monoclonal antibodies which specifically react with EGFR. In one embodiment, the method includes immunizing a transgenic non-human animal, e.g., a transgenic mouse, having a genome comprising a human heavy chain transgene and a human light chain transgene encoding all or a portion of an antibody of the invention, with a purified or enriched preparation of EGFR antigen and/or cells expressing EGFR. B cells (e.g., splenic B cells) of the animal are then obtained and fused with myeloma cells to form immortal, hybridoma cells that secrete human monoclonal antibodies against EGFR.

In yet another aspect, human anti-EGFR antibodies of the invention are derivatized, linked to or co-expressed with another functional molecule, e.g., another peptide or protein (e.g., an Fab' fragment). For example, an antibody or antigen-binding portion of the invention can be functionally linked (e.g., by chemical coupling, genetic fusion, noncovalent association or otherwise) to one or more other molecular entities, such as another antibody (e.g., to produce a bispecific or a multispecific antibody), a cytoxin, a cellular ligand or an antigen. Accordingly, present invention encompasses a large variety of antibody conjugates, bi- and multispecific molecules, and fusion proteins, all of which bind to EGFR expressing cells and which target other molecules to the cells, or which bind to EGFR and to other molecules or cells.

In a particular embodiment, the invention includes a bispecific or multispecific molecule comprising at least one first binding specificity for EGFR (e.g., a human anti-EGFR antibody or fragment or mimetic thereof), and a second binding specificity for an Fc receptor, e.g., human FcγRI or a human Fcα receptor, or another antigen on an antigen presenting cell (APC). Typically, bispecific and multispecific molecules of the invention comprise at least one antibody, or fragment thereof (e.g., an Fab, Fab', F(ab')$_2$, Fv, or a single chain Fv), preferably a human antibody or a portion thereof, or a "chimeric" or a "humanized" antibody or a portion thereof (e.g., has a variable region, or at least a complementarity determining region (CDR), derived from a non-human antibody (e.g., murine) with the remaining portion(s) being human in origin).

Accordingly, the present invention includes bispecific and multispecific molecules that bind to both human EGFR and to an Fc receptor, e.g., a human IgG receptor, e.g., an Fc-gamma receptor (FcγR), such as FcγRI (CD64), FcγRII (CD32), and FcγRIII (CD16). Other Fc receptors, such as human IgA receptors (e.g., FcαRI), also can be targeted. The Fc receptor is preferably located on the surface of an effector cell, e.g., a monocyte, macrophage or an activated polymorphonuclear cell. In a preferred embodiment, the bispecific and multispecific molecules bind to an Fc receptor at a site which is distinct from the immunoglobulin Fc (e.g., IgG or IgA) binding site of the receptor. Therefore, the binding of the bispecific and multispecific molecules is not blocked by physiological levels of immunoglobulins.

In another aspect, the present invention provides a conjugate comprising a human anti-EGFR antibody of the invention linked to a therapeutic moiety, e.g., a cytotoxic drug, an enzymatically active toxin, or a fragment thereof, a radioisotope, or a small molecule anti-cancer drug.

Alternatively, human antibodies of the invention can be co-administered with such therapeutic and cytotoxic agents, but not linked to them. They can be coadministered simultaneously with such agents (e.g., in a single composition or separately) or can be administered before or after administration of such agents. Such agents can include chemotherapeutic agents such as doxorubicin (adriamycin), cisplatin bleomycin sulfate, carmustine, chlorambucil, and cyclophosphamide hydroxyurea. Human antibodies of the invention also can be administered in conjunction with radiation therapy.

In another aspect, the present invention provides compositions, e.g., pharmaceutical and diagnostic compositions/kits, comprising a pharmaceutically acceptable carrier and at least one human monoclonal antibody of the invention, or an antigen-binding portion thereof, which specifically binds to EGFR. In one embodiment, the composition comprises a combination of the human antibodies or antigen-binding portions thereof, preferably each of which binds to a distinct epitope. For example, a pharmaceutical composition comprising a human monoclonal antibody that mediates highly effective killing of target cells in the presence of effector cells can be combined with another human monoclonal antibody that inhibits the growth of cells expressing EGFR. Thus, the combination provides multiple therapies tailored to provide the maximum therapeutic benefit. Compositions, e.g., pharmaceutical compositions, comprising a combination of at least one human monoclonal antibody of the invention, or antigen-binding portions thereof, and at least one bispecific or multispecific molecule of the invention, are also within the scope of the invention.

In another aspect the invention relates to a pharmaceutical composition comprising the human antibody of the invention as defined in any of the claims or embodiments herein and a pharmaceutically acceptable carrier.

In another aspect the pharmaceutical composition is in a form suitable for injection or infusion.

In another aspect the pharmaceutical composition is a liposome formulation.

In yet another aspect, the invention provides a method for inhibiting the proliferation and/or growth of a cell expressing EGFR, and/or inducing killing of a cell expressing EGFR, using human antibodies of the invention and related compositions as described above. In one embodiment, the method comprises contacting a cell expressing EGFR either in vitro or in vivo with one or a combination of human monoclonal antibodies of the invention in the presence of a human effector cell. The method can be employed in culture, e.g., in vitro or ex vivo (e.g., cultures comprising cells expressing EGFR and effector cells). For example, a sample containing cells expressing EGFR and effector cells can be cultured in vitro, and combined with an antibody of the invention, or an antigen-binding portion thereof (or a bispecific or multispecific molecule of the invention). Alternatively, the method can be performed in a subject, e.g., as part of an in vivo (e.g., therapeutic or prophylactic) protocol.

For use in in vivo treatment and prevention of diseases related to EGFR expression (e.g., over-expression), human antibodies of the invention are administered to patients (e.g., human subjects) at therapeutically effective dosages (e.g., dosages which result in growth inhibition, phagocytosis and/or killing of tumor cells expressing EGFR) using any suitable route of administration, such as injection and other routes of administration known in the art for antibody-based clinical products.

Typical EGFR-related diseases which can be treated and/or prevented using the human antibodies of the invention include, but are not limited to, autoimmune diseases and cancers. For example, cancers which can be treated and/or prevented include cancer of the bladder, breast, uterine/cervical, colon, kidney, ovarian, prostate, renal cell, pancreatic, colorectal, stomach, squamous cell, lung (non-small cell), esophageal, head and neck. Autoimmune diseases which can be treated include, for example, psoriasis and inflammatory arthritis, e.g., rheumatoid arthritis, systemic lupus erythematosus-associated arthritis, psoriatic arthritis, Menetrier's disease, systemic sclerosis, Sjögren's syndrome, pulmonary fibrosis, bronchial asthma, myelofibrosis, diabetic nephropathy, chronic allograft rejection, chronic glomerulonephritis, Crohn's disease, ulcerative colitis, hepatic cirrhosis, sclerosing cholangitis, chronic uveitis, or cicatricial pemphigoid.

In another aspect the invention relates to a method of treating or preventing Alzheimer's disease or other forms of dementia.

In one embodiment, the patient is additionally treated with one or more further therapeutic agents and/or physical therapies (e.g., radiation therapy, hyperthermia, transplantation (e.g., bone marrow transplantation), surgery, sunlight, or phototherapy), such as one or more further therapeutic agents and/or physical therapies as disclosed in the following. The patient can also be additionally treated with a chemotherapeutic agent, radiation, or an agent that modulates, e.g., enhances or inhibits, the expression or activity of an Fc receptor, e.g., an Fcα receptor or an Fcγ receptor, such as a cytokine. Typical cytokines for administration during treatment include granulocyte colony-stimulating factor (G-CSF), granulocyte-macrophage colony-stimulating factor (GM-CSF), interferon-γ (IFN-γ), and tumor necrosis factor (TNF). Typical therapeutic agents include, among others, anti-neoplastic agents such as doxorubicin (adriamycin), cisplatin bleomycin sulfate, carmustine, chlorambucil, and cyclophosphamide hydroxyurea.

The additional therapeutic agents and/or physical therapies may be administered either prior to, simultaneously with, or following administration of the human antibody.

In another aspect the pharmaceutical composition comprises one or more further therapeutic agents, such as one or more agents selected from chemotherapeutic agents, immunosuppressive agent, anti-inflammatory agents, and anti-psoriasis agents, and/or physical therapies (e.g., radiation therapy, hyperthermia, transplantation (e.g., bone marrow transplantation), surgery, sunlight, or phototherapy).

In another aspect the pharmaceutical composition comprises one or more further chemotherapeutic agents selected from the group consisting of nitrogen mustards (e.g., cyclophosphamide and ifosfamide), aziridines (e.g., thiotepa), alkyl sulfonates (e.g., busulfan), nitrosoureas (e.g., carmustine and streptozocin), platinum complexes (e.g., carboplatin and cisplatin), non-classical alkylating agents (e.g., dacarbazine and temozolamide), folate analogs (e.g., methotrexate), purine analogs (e.g., fludarabine and mercaptopurine), adenosine analogs (e.g., cladribine and pentostatin), pyrimidine analogs (e.g., fluorouracil (alone or in combination with leucovorin) and gemcitabine), substituted ureas (e.g., hydroxyurea), antitumor antibiotics (e.g., bleomycin and doxorubicin), epipodophyllotoxins (e.g., etoposide and teniposide), microtubule agents (e.g., docetaxel and paclitaxel), camptothecin analogs (e.g., irinotecan and topotecan), enzymes (e.g., asparaginase), cytokines (e.g., interleukin-2 and interferon-α), monoclonal antibodies (e.g., trastuzumab and bevacizumab), recombinant toxins and immunotoxins (e.g., recombinant cholera toxin-B and TP-38), cancer gene therapies, and cancer vaccines (e.g., vaccine against telomerase). Other treatments may include hyperthermia, radiation therapy, transplantation and surgery.

In another aspect the pharmaceutical composition comprises one or more further therapeutic agents selected from the group consisting of immunosuppressive antibodies (e.g., antibodies against MHC, CD2, CD3, CD4, CD7, CD28, B7, CD40, CD45, IFN-γ TNF-α, IL-4, IL-5, IL-6R, IL-7, IL-8, IL-10, CD11a, CD20, or CD58, or antibodies against their ligands) and other immunomodulatory compounds (e.g., soluble IL-15R or IL-10).

In another aspect the pharmaceutical composition comprises one or more further immunosuppressive agents selected from the group consisting of cyclosporine, azathioprine, mycophenolic acid, mycophenolate mofetil, corticosteroids (e.g., prednisone), methotrexate, gold salts, sulfasalazine, antimalarials, brequinar, leflunomide, mizoribine, 15-deoxyspergualine, 6-mercaptopurine, cyclophosphamide, rapamycin, tacrolimus (FK-506), OKT3, and anti-thymocyte globulin.

In another aspect the pharmaceutical composition comprises one or more further anti-inflammatory agents selected from the group consisting of aspirin and other salicylates, steroidal drugs, NSAIDs (nonsteroidal anti-inflammatory drugs) (e.g., ibuprofen, fenoprofen, naproxen, sulindac, diclofenac, piroxicam, ketoprofen, diflunisal, nabumetone, etodolac, oxaprozin, and indomethacin), Cox-2 inhibitors (e.g., rofecoxib and celecoxib), and DMARDs (disease modifying antirheumatic drugs) (e.g., methotrexate, hydroxychloroquine, sulfasalazine, azathioprine, pyrimidine synthesis inhibitors (e.g., leflunomide), IL-1 receptor blocking agents (e.g., anakinra), TNF-α blocking agents (e.g., etanercept, infliximab and adalimumab), anti-IL-6R antibodies, CTLA4Ig, and anti-IL-15 antibodies).

In another aspect the pharmaceutical composition comprises one or more further anti-psoriasis agents selected from the group consisting of coal tar, A vitamin, anthralin, calcipotrien, tarazotene, corticosteroids, methotrexate, retinoids (e.g., acitretin), cyclosporine, etanercept, alefacept, efaluzimab, 6-thioguanine, mycophenolate mofetil, tacrolimus (FK-506), and hydroxyurea.

Other treatments may include exposure to sunlight or phototherapy, including UVB (broad-band and narrow-band ultraviolet B), UVA (ultraviolet A) and PUVA (psoralen methoxalen plus ultraviolet A).

In one embodiment the antibodies of the invention are administered in combination with two or more of the above therapies, such as in combination with methotrexate+phototherapy (PUVA or UVA); methotrexate+acitretin; acitretin+phototherapy (PUVA or UVA); methotrexate+acitretin+phototherapy (PUVA or UVB); hydroxyurea+phototherapy (PUVA or UVB); hydroxyurea+acitretin; cyclosporine+methotrexate; or calcipotrien+phototherapy (UVB).

In another aspect, the invention relates to an immunoconjugate comprising an antibody according to the invention linked to a radioisotope, cytotoxic agent (e.g., calicheamicin and duocarmycin), a cytostatic agent, or a chemotherapeutic drug.

In another aspect the invention relates to an immunoconjugate, wherein the antibody is linked to a radioisotope (e.g., iodine-131, yttrium-90 or indium-111).

In another aspect the invention relates to an immunoconjugate, wherein the antibody is linked to any one of the chemotherapeutic agents as defined above.

To increase the therapeutic efficacy of human anti-EGFR antibodies of the invention against cancer cells which do not highly express EGFR, the antibodies can be co-administered with an agent which upregulates or otherwise effects expression of EGFR, such as a lymphokine preparation which cause upregulated and more homogeneous expression of EGFR on tumor cells. Lymphokine preparations suitable for administration include interferon-gamma, tumor necrosis factor, and combinations thereof. These can be administered intravenously. Suitable dosages of lymphokine typically range from 10,000 to 1,000,000 units/patient.

In another aspect, the invention relates to a pharmaceutical composition comprising an expression vector comprising a nucleotide sequence encoding the variable region of a light chain, heavy chain or both light and heavy chains of a human antibody which binds EGFR.

In another aspect, the invention relates to a pharmaceutical composition comprising an expression vector comprising a nucleotide sequence encoding the variable region of a light chain, heavy chain or both light and heavy chains of a human antibody which binds EGFR, and further comprising a nucleotide sequence encoding the constant region of a light chain, heavy chain or both light and heavy chains of a human antibody which binds EGFR.

In another aspect, the invention relates to a pharmaceutical composition comprising an expression vector comprising a nucleotide sequence encoding heavy chain and light chain variable regions which comprise the amino acid sequences shown in SEQ ID NO:2 and SEQ ID NO:4, respectively, and conservative sequence modifications thereof.

In yet another aspect, the present invention provides a method for detecting in vitro or in vivo the presence of EGFR antigen in a sample, e.g., for diagnosing an EGFR-related disease. In one embodiment, this is achieved by contacting a sample to be tested, optionally along with a control sample, with a human monoclonal antibody of the invention (or an antigen-binding portion thereof) under conditions that allow for formation of a complex between the antibody and EGFR. Complex formation is then detected (e.g., using an ELISA). When using a control sample along with the test sample, complex is detected in both samples and any statistically significant difference in the formation of complexes between the samples is indicative the presence of EGFR antigen in the test sample.

Other features and advantages of the instant invention be apparent from the following detailed description and claims.

BRIEF DESCRIPTION OF THE DRAWINGS

FIGS. 15A and 15B show the nucleotide (SEQ ID NOs:1 and 3) and amino acid (SEQ ID NOs:2, and 4) sequences of the $V_H$- and $V_L$-regions of 2F8, respectively, with CDR regions designated (SEQ ID NOs:5, 6, 7, 8, 9, and 10).

DETAILED DESCRIPTION OF THE INVENTION

Figure 1:
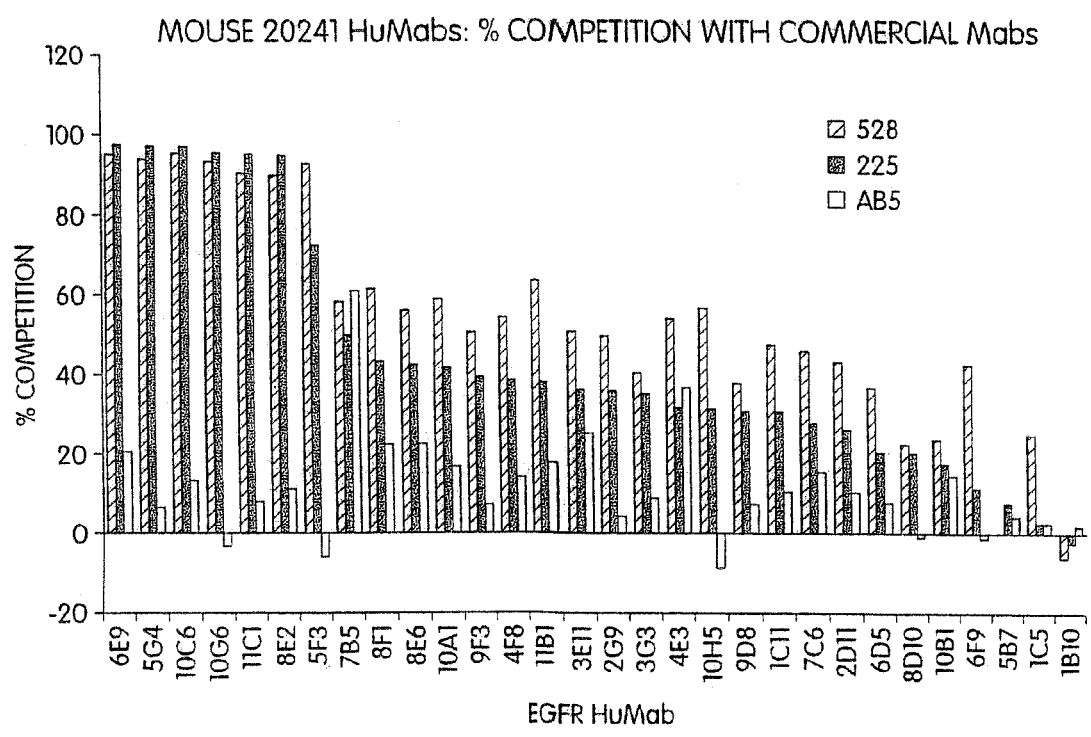
FIG. 1 is a graph showing competitive ELISA with hybridoma supernatants from mouse 20241 versus murine monoclonal anti-EGFR MAbs 225, 528, and AB5.

The present invention provides novel antibody-based therapies for treating and diagnosing diseases characterized by expression, particularly over-expression, of epidermal growth factor receptor antigen (referred to herein as "EGFR"). Therapies of the invention employ isolated human IgG monoclonal antibodies, or antigen-binding portions thereof, which bind to an epitope present on EGFR. Other isolated human monoclonal antibodies encompassed by the present invention include IgA, IgG1-4, IgE, IgM, and IgD antibodies, e.g., IgG1,κ or IgG1,λ isotypes, or IgG4,κ or IgG4,λ isotypes. In one embodiment, the human antibodies are produced in a non-human transgenic animal, e.g., a transgenic mouse, capable of producing multiple isotypes of human monoclonal antibodies to EGFR (e.g., IgG, IgA and/ or IgE) by undergoing V-D-J recombination and isotype switching. Accordingly, aspects of the invention include not only antibodies, antibody fragments, and pharmaceutical compositions thereof, but also non-human transgenic animals, B-cells, host cell transfectomas, and hybridomas which produce monoclonal antibodies. Methods of using the antibodies of the invention to detect a cell expressing EGFR or a related, cross-reactive growth factor receptor, or to inhibit growth, differentiation and/or motility of a cell expressing EGFR, either in vitro or in vivo, are also encompassed by the invention.

In order that the present invention may be more readily understood, certain terms are first defined. Additional definitions are set forth throughout the detailed description.

The terms "epidermal growth factor receptor," "EGFR," and "EGFR antigen" are used interchangeably herein, and include variants, isoforms and species homologs of human EGFR. In a preferred embodiment, binding of an antibody of the invention to the EGFR-antigen inhibits the growth of cells expressing EGFR (e.g., a tumor cell) by inhibiting or blocking binding of EGFR ligand to EGFR. The term "EGFR ligand" encompasses all (e.g., physiological) ligands for EGFR, including EGF, TGF-α, heparin binding EGF (HB-EGF), amphiregulin (AR), and epiregulin (EPI). In another preferred embodiment, binding of an antibody of the invention to the EGFR-antigen mediates effector cell phagocytosis and/or killing of cells expressing EGFR.

As used herein, the term "inhibits growth" (e.g., referring to cells) is intended to include any measurable decrease in the growth of a cell when contacted with an anti-EGFR antibody as compared to the growth of the same cell not in contact with an anti-EGFR antibody, e.g., the inhibition of growth of a cell by at least about 10%, 20%, 30%, 40%, 50%, 60%, 70%, 80%, 90%, 99%, or 100%.

As used herein, the terms "inhibits binding" and "blocks binding" (e.g., referring to inhibition/blocking of binding of EGFR ligand to EGFR) are used interchangeably and encompass both partial and complete inhibition/blocking. The inhibition/blocking of EGFR ligand to EGFR preferably reduces or alters the normal level or type of cell signaling that occurs when EGFR ligand binds to EGFR without inhibition or blocking. Inhibition and blocking are also intended to include any measurable decrease in the binding affinity of EGFR ligand to EGFR when in contact with an anti-EGFR antibody as compared to the ligand not in contact with an anti-EGFR antibody, e.g., the blocking of EGFR ligands to EGFR by at least about 10%, 20%, 30%, 40%, 50%, 60%, 70%, 80%, 90%, 99%, or 100%.

The term "antibody" as referred to herein includes whole antibodies and any antigen binding fragment (i.e., "antigen-binding portion") or single chain thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding portion" of an antibody (or simply "antibody portion"), as used herein, refers to one or more fragments of an antibody that retain the ability to specifically bind to an antigen (e.g., EGFR). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')₂ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

The term "bispecific molecule" is intended to include any agent, e.g., a protein, peptide, or protein or peptide complex, which has two different binding specificities. For example, the molecule may bind to, or interact with, (a) a cell surface antigen and (b) an Fc receptor on the surface of an effector cell. The term "multispecific molecule" or "heterospecific molecule" is intended to include any agent, e.g., a protein, peptide, or protein or peptide complex, which has more than two different binding specificities. For example, the molecule may bind to, or interact with, (a) a cell surface antigen, (b) an Fc receptor on the surface of an effector cell, and (c) at least one other component. Accordingly, the invention includes, but is not limited to, bispecific, trispecific, tetraspecific, and other multispecific molecules which are directed to cell surface antigens, such as EGFR, and to other targets, such as Fc receptors on effector cells.

The term "bispecific antibodies" also includes diabodies. Diabodies are bivalent, bispecific antibodies in which the VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123).

As used herein, the term "heteroantibodies" refers to two or more antibodies, antibody binding fragments (e.g., Fab), derivatives therefrom, or antigen binding regions linked together, at least two of which have different specificities. These different specificities include a binding specificity for an Fc receptor on an effector cell, and a binding specificity for an antigen or epitope on a target cell, e.g., a tumor cell. The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The terms "monoclonal antibody" or "monoclonal antibody composition" as used herein refer to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences. In one embodiment, the human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

The term "recombinant human antibody", as used herein, is intended to include all human antibodies that are prepared, expressed, created or isolated by recombinant means, such as (a) antibodies isolated from an animal (e.g., a mouse) that is transgenic for human immunoglobulin genes or a hybridoma prepared therefrom (described further in Section I, below), (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable and constant regions derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

As used herein, a "heterologous antibody" is defined in relation to the transgenic non-human organism producing such an antibody. This term refers to an antibody having an amino acid sequence or an encoding nucleic acid sequence corresponding to that found in an organism not consisting of the transgenic non-human animal, and generally from a species other than that of the transgenic non-human animal.

As used herein, a "heterohybrid antibody" refers to an antibody having a light and heavy chains of different organismal origins. For example, an antibody having a human heavy chain associated with a murine light chain is a heterohybrid antibody. Examples of heterohybrid antibodies include chimeric and humanized antibodies, discussed supra.

An "isolated antibody," as used herein, is intended to refer to an antibody which is substantially free of other antibodies having different antigenic specificities (e.g., an isolated antibody that specifically binds to EGFR is substantially free of antibodies that specifically bind antigens other than EGFR). An isolated antibody that specifically binds to an epitope, isoform or variant of human EGFR may, however, have cross-reactivity to other related antigens, e.g., from other species (e.g., EGFR species homologs). Moreover, an isolated antibody may be substantially free of other cellular material and/or chemicals. In one embodiment of the invention, a combination of "isolated" monoclonal antibodies having different specificities are combined in a well defined composition.

As used herein, "specific binding" refers to antibody binding to a predetermined antigen. Typically, the antibody binds with an affinity of at least about $1 \times 10^7$ $M^{-1}$, and binds to the predetermined antigen with an affinity that is at least two-fold greater than its affinity for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen".

As used herein, the term "high affinity" for an IgG antibody refers to a binding affinity of at least about $10^7$ $M^{-1}$, preferably at least about $10^8$ $M^{-1}$, more preferably at least about $10^9 M^{-1}$, and still more preferably at least about $10^{10}$ $M^{-1}$, $10^{11}$ $M^{-1}$, $10^{12}$ $M^{-1}$ or greater, e.g., up to $10^{13}$ $M^{-1}$ or greater. However, "high affinity" binding can vary for other antibody isotypes. For example, "high affinity" binding for an IgM isotype refers to a binding affinity of at least about $1 \times 10^7 M^{-1}$.

The term "$K_A$", as used herein, is intended to refer to the association constant of a particular antibody-antigen interaction.

The term "$K_D$", as used herein, is intended to refer to the dissociation constant of a particular antibody-antigen interaction.

As used herein, "isotype" refers to the antibody class (e.g., IgM or IgG1) that is encoded by heavy chain constant region genes.

As used herein, "isotype switching" refers to the phenomenon by which the class, or isotype, of an antibody changes from one Ig class to one of the other Ig classes.

As used herein, "nonswitched isotype" refers to the isotypic class of heavy chain that is produced when no isotype switching has taken place; the CH gene encoding the nonswitched isotype is typically the first CH gene immediately downstream from the functionally rearranged VDJ gene. Isotype switching has been classified as classical or non-classical isotype switching. Classical isotype switching occurs by recombination events which involve at least one switch sequence region in the transgene. Non-classical isotype switching may occur by, for example, homologous recombination between human $\sigma_\mu$ and human $\Sigma_\mu$ (δ-associated deletion). Alternative non-classical switching mechanisms, such as intertransgene and/or interchromosomal recombination, among others, may occur and effectuate isotype switching.

As used herein, the term "switch sequence" refers to those DNA sequences responsible for switch recombination. A "switch donor" sequence, typically a μ switch region, will be 5' (i.e., upstream) of the construct region to be deleted during the switch recombination. The "switch acceptor" region will be between the construct region to be deleted and the replacement constant region (e.g., γ, ε, etc.). As there is no specific site where recombination always occurs, the final gene sequence will typically not be predictable from the construct.

As used herein, "glycosylation pattern" is defined as the pattern of carbohydrate units that are covalently attached to a protein, more specifically to an immunoglobulin protein. A glycosylation pattern of a heterologous antibody can be characterized as being substantially similar to glycosylation patterns which occur naturally on antibodies produced by the species of the nonhuman transgenic animal, when one of ordinary skill in the art would recognize the glycosylation pattern of the heterologous antibody as being more similar to said pattern of glycosylation in the species of the nonhuman transgenic animal than to the species from which the CH genes of the transgene were derived.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "rearranged" as used herein refers to a configuration of a heavy chain or light chain immunoglobulin locus wherein a V segment is positioned immediately adjacent to a D-J or J segment in a conformation encoding essentially a complete VH or VL domain, respectively. A rearranged immunoglobulin gene locus can be identified by comparison to germline DNA; a rearranged locus will have at least one recombined heptamer/nonamer homology element.

The term "unrearranged" or "germline configuration" as used herein in reference to a V segment refers to the configuration wherein the V segment is not recombined so as to be immediately adjacent to a D or J segment.

The term "nucleic acid molecule", as used herein, is intended to include DNA molecules and RNA molecules. A nucleic acid molecule may be single-stranded or double-stranded, but preferably is double-stranded DNA.

The term "isolated nucleic acid molecule," as used herein in reference to nucleic acids encoding antibodies or antibody portions (e.g., VH, VL, CDR3) that bind to EGFR, is intended to refer to a nucleic acid molecule in which the nucleotide sequences encoding the antibody or antibody portion are free of other nucleotide sequences encoding antibodies or antibody portions that bind antigens other than EGFR, which other sequences may naturally flank the nucleic acid in human genomic DNA. In one embodiment, the human anti-EGFR antibody, or portion thereof, includes the nucleotide or amino acid sequence of 2F8, as well as heavy chain (VH) and light chain (VL) variable regions having the sequences shown in SEQ ID NOs:1 and 3, and 2 and 4, respectively.

As disclosed and claimed herein, the sequences set forth in SEQ ID NOs: 1-12 include "conservative sequence modifications", i.e., nucleotide and amino acid sequence modifications which do not significantly affect or alter the binding characteristics of the antibody encoded by the nucleotide sequence or containing the amino acid sequence. Such conservative sequence modifications include nucleotide and amino acid substitutions, additions and deletions. Modifications can be introduced into SEQ ID NOs:1-12 by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in a human anti-EGFR antibody is preferably replaced with another amino acid residue from the same side chain family.

Alternatively, in another embodiment, mutations can be introduced randomly along all or part of a anti-EGFR antibody coding sequence, such as by saturation mutagenesis, and the resulting modified anti-EGFR antibodies can be screened for binding activity.

Accordingly, antibodies encoded by the (heavy and light chain variable region) nucleotide sequences disclosed herein and/or containing the (heavy and light chain variable region) amino acid sequences disclosed herein (i.e., SEQ ID NOs:1-12) include substantially similar antibodies encoded by or containing similar sequences which have been conservatively modified. Further discussion as to how such substantially similar antibodies can be generated based on the partial (i.e., heavy and light chain variable regions) sequences disclosed herein as SEQ ID NOs:1-12 is provided below.

For nucleic and amino acids, the term "substantial homology" indicates that two nucleic/amino acids, or designated sequences thereof, when optimally aligned and compared, are identical, with appropriate nucleotide/amino acid residue insertions or deletions, in at least about 80% of the nucleotides/amino acid residues, usually at least about 90% to 95%, and more preferably at least about 98% to 99.5% of the nucleotides/amino acid residues. Alternatively, substantial homology exists for nucleic acids when the segments will hybridize under selective hybridization conditions, to the complement of the strand.

For nucleotide acid and amino acid sequences, the term "homology" indicates the degree of identity between two sequences, when optimally aligned and compared, with appropriate nucleotide insertions or deletions.

The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (*Comput. Appl. Biosci.,* 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* 48:444-453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences of the present invention can further be used as a "query sequence" to perform a search against public databases to, for example, identify related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See http://www.ncbi.nlm.nih.gov.

The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. *Current Protocols in Molecular Biology*, Greene Publishing and Wiley Interscience, New York (1987).

The nucleic acid compositions of the present invention, while often in a native sequence (except for modified restriction sites and the like), from either cDNA, genomic or mixtures may be mutated, thereof in accordance with standard techniques to provide gene sequences. For coding sequences, these mutations, may affect amino acid sequence as desired. In particular, DNA sequences substantially homologous to or derived from native V, D, J, constant, switches and other such sequences described herein are contemplated (where "derived" indicates that a sequence is identical or modified from another sequence).

A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination.

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. Recombinant host cells include, for example, CHO cells and lymphocytic cells.

The term "transfectoma", as used herein, includes recombinant eukaryotic host cell expressing the antibody, such as CHO cells or NS/0 cells.

As used herein, the term "subject" includes any human or nonhuman animal. The term "nonhuman animal" includes all vertebrates, e.g., mammals and non-mammals, such as non-human primates, sheep, dog, cow, chickens, amphibians, reptiles, etc.

The terms "transgenic, nonhuman animal" refers to a nonhuman animal having a genome comprising one or more human heavy and/or light chain transgenes or transchromosomes (either integrated or non-integrated into the animal's natural genomic DNA) and which is capable of expressing fully human antibodies. For example, a transgenic mouse can have a human light chain transgene and either a human heavy chain transgene or human heavy chain transchromosome, such that the mouse produces human anti-EGFR antibodies when immunized with EGFR and/or cells expressing EGFR. The human heavy chain transgene can be integrated into the chromosomal DNA of the mouse, as is the case for transgenic, e.g., HuMAb mice, or the human heavy chain transgene can be maintained extrachromosomally, as is the case for transchromosomal (e.g., KM) mice as described in WO 02/43478. Such transgenic and transchromosomal mice are capable of producing multiple isotypes of human monoclonal antibodies to EGFR (e.g., IgG, IgA and/or IgE) by undergoing V-D-J recombination and isotype switching.

Various aspects of the invention are described in further detail in the following subsections.

I. Production of Human Antibodies to EGFR

The monoclonal antibodies (MAbs) of the invention can be produced by a variety of techniques, including conventional monoclonal antibody methodology e.g., the standard somatic cell hybridization technique of Kohler and Milstein (1975)

*Nature* 256: 495. Although somatic cell hybridization procedures are preferred, in principle, other techniques for producing monoclonal antibody can be employed e.g., viral or oncogenic transformation of B lymphocytes.

The preferred animal system for preparing hybridomas is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known.

In a preferred embodiment, human monoclonal antibodies directed against EGFR can be generated using transgenic mice carrying parts of the human immune system rather than the mouse system. These transgenic mice, referred to herein as "HuMAb" mice, contain a human immunoglobulin gene miniloci that encodes unrearranged human heavy (μ and δ) and κ light chain immunoglobulin sequences, together with targeted mutations that inactivate the endogenous μ and κ chain loci (Lonberg, et al. (1994) *Nature* 368(6474): 856-859). Accordingly, the mice exhibit reduced expression of mouse IgM or κ, and in response to immunization, the introduced human heavy and light chain transgenes undergo class switching and somatic mutation to generate high affinity human IgGκ monoclonal antibodies (Lonberg, N. et al. (1994), supra; reviewed in Lonberg, N. (1994) *Handbook of Experimental Pharmacology* 113:49-101; Lonberg, N. and Huszar, D. (1995) *Intern. Rev. Immunol.* Vol. 13: 65-93, and Harding, F. and Lonberg, N. (1995) *Ann. N.Y. Acad. Sci.* 764:536-546). The preparation of HuMAb mice is described in detail Section II below and in Taylor, L. et al. (1992) *Nucleic Acids Research* 20:6287-6295; Chen, J. et al. (1993) *International Immunology* 5: 647-656; Tuaillon et al. (1993) *Proc. Natl. Acad. Sci. USA* 90:3720-3724; Choi et al. (1993) *Nature Genetics* 4:117-123; Chen, J. et al. (1993) *EMBO J.* 12: 821-830; Tuaillon et al. (1994) *J. Immunol.* 152:2912-2920; Lonberg et al., (1994) *Nature* 368(6474): 856-859; Lonberg, N. (1994) *Handbook of Experimental Pharmacology* 113:49-101; Taylor, L. et al. (1994) *International Immunology* 6: 579-591; Lonberg, N. and Huszar, D. (1995) *Intern. Rev. Immunol.* Vol. 13: 65-93; Harding, F. and Lonberg, N. (1995) *Ann. N.Y. Acad. Sci.* 764:536-546; Fishwild, D. et al. (1996) *Nature Biotechnology* 14: 845-851, the contents of all of which are hereby incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay, and GenPharm International; U.S. Pat. No. 5,545,807 to Surani et al.; International Publication Nos. WO 98/24884, published on Jun. 11, 1998; WO 94/25585, published Nov. 10, 1994; WO 93/1227, published Jun. 24, 1993; WO 92/22645, published Dec. 23, 1992; WO 92/03918, published Mar. 19, 1992, the disclosures of all of which are hereby incorporated by reference in their entity. Alternatively, the HCO12 transgenic mice described in Example 2, can be used to generate human anti-EGFR antibodies.

Human Antibody Immunizations

To generate fully human monoclonal antibodies to EGFR, HuMAb mice can be immunized with a purified or enriched preparation of EGFR antigen and/or cells expressing EGFR, as described by Lonberg, N. et al. (1994) *Nature* 368(6474): 856-859; Fishwild, D. et al. (1996) *Nature Biotechnology* 14: 845-851 and WO 98/24884. Preferably, the mice will be 6-16 weeks of age upon the first infusion. For example, a purified or enriched preparation (5-20 μg) of EGFR antigen (e.g., purified from EGFR-expressing LNCaP cells) can be used to immunize the HuMAb mice intraperitoneally. In the event that immunizations using a purified or enriched preparation of EGFR antigen do not result in antibodies, mice can also be immunized with cells expressing EGFR, e.g., a tumor cell line, to promote immune responses.

Cumulative experience with various antigens has shown that the HuMAb transgenic mice respond best when initially immunized intraperitoneally (IP) with antigen in complete Freund's adjuvant, followed by every other week i.p. immunizations (up to a total of 6) with antigen in incomplete Freund's adjuvant. The immune response can be monitored over the course of the immunization protocol with plasma samples being obtained by retroorbital bleeds. The plasma can be screened by ELISA (as described below), and mice with sufficient titers of anti-EGFR human immunoglobulin can be used for fusions. Mice can be boosted intravenously with antigen 3 days before sacrifice and removal of the spleen. It is expected that 2-3 fusions for each antigen may need to be performed. Several mice will be immunized for each antigen. For example, a total of twelve HuMAb mice of the HCO7 and HCO12 strains can be immunized.

Generation of Hybridomas Producing Human Monoclonal Antibodies to EGFR

The mouse splenocytes can be isolated and fused with PEG to a mouse myeloma cell line based upon standard protocols. The resulting hybridomas are then screened for the production of antigen-specific antibodies. For example, single cell suspensions of splenic lymphocytes from immunized mice are fused to one-sixth the number of P3X63-Ag8.653 nonsecreting mouse myeloma cells (ATCC, CRL 1580) with 50% PEG. Cells are plated at approximately $2 \times 10^5$ in flat bottom microtiter plate, followed by a two week incubation in selective medium containing 20% fetal Clone Serum, 18% "653" conditioned media, 5% origen (IGEN), 4 mM L-glutamine, 1 mM L~glutamine, 1 mM sodium pyruvate, 5 mM HEPES, 0.055 mM 2-mercaptoethanol, 50 units/ml penicillin, 50 mg/ml streptomycin, 50 mg/ml gentamycin and 1×HAT (Sigma; the HAT is added 24 hours after the fusion). After two weeks, cells are cultured in medium in which the HAT is replaced with HT. Individual wells are then screened by ELISA for human anti-EGFR monoclonal IgM and IgG antibodies. Once extensive hybridoma growth occurs, medium is observed usually after 10-14 days. The antibody secreting hybridomas are replated, screened again, and if still positive for human IgG, anti-EGFR monoclonal antibodies, can be subcloned at least twice by limiting dilution. The stable subclones are then cultured in vitro to generate small amounts of antibody in tissue culture medium for characterization.

Generation of Transfectomas Producing Human Monoclonal Antibodies to EGFR

Human antibodies of the invention can also be produced in a host cell transfectoma using, for example, a combination of recombinant DNA techniques and gene transfection methods as is well known in the art (Morrison, S. (1985) *Science* 229:1202).

For example, to express the antibodies, or antibody fragments thereof, DNAs encoding partial or full-length light and heavy chains, can be obtained by standard molecular biology techniques (e.g., PCR amplification, site directed mutagenesis) and can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_L$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to includes promoters, enhancers and other expression control elements (e.g., polyadenylation signals) that control the transcription or translation of the antibody chain genes. Such regulatory sequences are described, for example, in Goeddel; Gene Expression Technology. Methods in Enzymology 185, Academic Press, San Diego, Calif. (1990). It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP)) and polyoma. Alternatively, nonviral regulatory sequences may be used, such as the ubiquitin promoter or β-globin promoter.

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody.

Preferred mammalian host cells for expressing the recombinant antibodies of the invention include Chinese Hamster Ovary (CHO cells) (including dhfr-CHO cells, described in Urlaub and Chasin, (1980) Proc. Natl. Acad. Sci. USA 77:4216-4220, used with a DHFR selectable marker, e.g., as described in R. J. Kaufman and P. A. Sharp (1982) Mol. Biol. 159:601-621), NS/0 myeloma cells, COS cells and SP2.0 cells. In particular for use with NS/0 myeloma cells, another preferred expression system is the GS gene expression system disclosed in WO 87/04462, WO 89/01036 and EP 338 841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Use of Partial Antibody Sequences to Express Intact Antibodies

Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al., 1998, *Nature* 332:323-327; Jones, P. et al., 1986, *Nature* 321:522-525; and Queen, C. et al., 1989, *Proc. Natl. Acad. See. U.S.A.* 86:10029-10033). Such framework sequences can be obtained from public DNA databases that include germline antibody gene sequences. These germline sequences will differ from mature antibody gene sequences because they will not include completely assembled variable genes, which are formed by V(D)J joining during B cell maturation. Germline gene sequences will also differ from the sequences of a high affinity secondary repertoire antibody at individual evenly across the variable region. For example, somatic mutations are relatively infrequent in the amino-terminal portion of framework region. For example, somatic mutations are relatively infrequent in the amino terminal portion of framework region 1 and in the carboxy-terminal portion of framework region 4. Furthermore, many somatic mutations do not significantly alter the binding properties of the antibody. For this reason, it is not necessary to obtain the entire DNA sequence of a particular antibody in order to recreate an intact recombinant antibody having binding properties similar to those of the original antibody (see PCT/US99/05535 filed on Mar. 12, 1999, which is herein incorporated by referenced for all purposes). Partial heavy and light chain sequence spanning the CDR regions is typically sufficient for this purpose. The partial sequence is used to determine which germline variable and joining gene segments contributed to the recombined antibody variable genes. The germline sequence is then used to fill in missing portions of the variable regions. Heavy and light chain leader sequences are cleaved during protein maturation and do not contribute to the properties of the final antibody. For this reason, it is necessary to use the corresponding germline leader sequence for expression constructs. To add missing sequences, cloned cDNA sequences cab be combined with synthetic oligonucleotides by ligation or PCR amplification. Alternatively, the entire variable region can be synthesized as a set of short, overlapping, oligonucleotides and combined by PCR amplification to create an entirely synthetic variable region clone. This process has certain advantages such as elimination or inclusion or particular restriction sites, or optimization of particular codons.

The nucleotide sequences of heavy and light chain transcripts from a hybridomas are used to design an overlapping set of synthetic oligonucleotides to create synthetic V sequences with identical amino acid coding capacities as the natural sequences. The synthetic heavy and kappa chain sequences can differ from the natural sequences in three ways: strings of repeated nucleotide bases are interrupted to facilitate oligonucleotide synthesis and PCR amplification; optimal translation initiation sites are incorporated according to Kozak's rules (Kozak, 1991, J. Biol. Chem. 266:19867-19870); and, HindIII sites are engineered upstream of the translation initiation sites.

For both the heavy and light chain variable regions, the optimized coding, and corresponding non-coding, strand sequences are broken down into 30-50 nucleotide approximately the midpoint of the corresponding non-coding oligonucleotide. Thus, for each chain, the oligonucleotides can be assemble into overlapping double stranded sets that span segments of 150-400 nucleotides. The pools are then used as templates to produce PCR amplification products of 150-400 nucleotides. Typically, a single variable region oligonucleotide set will be broken down into two pools which are separately amplified to generate two overlapping PCV products. These overlapping products are then combined by PCT amplification to form the complete variable region. It may also be desirable to include an overlapping fragment of the heavy or light chain constant region (including the BbsI site of the kappa light chain, or the AgeI site if the gamma heavy chain) in the PCR amplification to generate fragments that can easily be cloned into the expression vector constructs.

The reconstructed heavy and light chain variable regions are then combined with cloned promoter, translation initiation, constant region, 3' untranslated, polyadenylation, and transcription termination, sequences to form expression vector constructs. The heavy and light chain expression constructs can be combined into a single vector, co-transfected, serially transfected, or separately transfected into host cells which are then fused to form a host cell expressing both chains.

Plasmids for use in construction of expression vectors for human IgGκ are described below. The plasmids were constructed so that PCR amplified V heavy and V kappa light chain cDNA sequences could be used to reconstruct complete heavy and light chain minigenes. These plasmids can be used to express completely human, or chimeric IgG1κ or IgG$_4$κ antibodies. Similar plasmids can be constructed for expression of other heavy chain isotypes, or for expression of antibodies comprising lambda light chains.

Thus, in another aspect of the invention, the structural features of an human anti-EGFR antibodies of the invention, e.g., 2F8, are used to create structurally related human anti-EGFR antibodies that retain at least one functional property of the antibodies of the invention, such as binding to EGFR. More specifically, one or more CDR regions of 2F8 can be combined recombinantly with known human framework regions and CDRs to create additional, recombinantly-engineered, human anti-EGFR antibodies of the invention.

Accordingly, in another embodiment, the invention provides a method for preparing an anti-EGFR antibody comprising:

preparing an antibody comprising (1) human heavy chain framework regions and human heavy chain CDRs, wherein at least one of the human heavy chain CDRs comprises an amino acid sequence selected from the amino acid sequences of CDRs shown in FIG. 15 (SEQ ID NOs:5, 6, and 7); and (2) human light chain framework regions and human light chain CDRs, wherein at least one of the human light chain CDRs comprises an amino acid sequence selected from the amino acid sequences of CDRs shown in FIG. 15 (SEQ ID NOs:8, 9, and 10); wherein the antibody retains the ability to bind to EGFR.

The ability of the antibody to bind EGFR can be determined using standard binding assays, such as those set forth in the Examples (e.g., an ELISA). Since it is well known in the art that antibody heavy and light chain CDR3 domains play a particularly important role in the binding specificity/affinity of an antibody for an antigen, the recombinant antibodies of the invention prepared as set forth above preferably comprise the heavy and light chain CDR3s of 2F8. The antibodies further can comprise the CDR2s of 2F8. The antibodies further can comprise the CDR1s of 2F8. Accordingly, the invention further provides anti-EGFR antibodies comprising: (1) human heavy chain framework regions, a human heavy chain CDR1 region, a human heavy chain CDR2 region, and a human heavy chain CDR3 region, wherein the human heavy chain CDR3 region is the CDR3 of 2F8 as shown in FIG. 15 (SEQ ID NO:7); and (2) human light chain framework regions, a human light chain CDR1 region, a human light chain CDR2 region, and a human light chain CDR3 region, wherein the human light chain CDR3 region is the CDR3 of 2F8 as shown in FIG. 15 (SEQ ID NO: 10), wherein the antibody binds EGFR. The antibody may further comprise the heavy chain CDR2 and/or the light chain CDR2 of 2F8. The antibody may further comprise the heavy chain CDR1 and/or the light chain CDR1 of 2F8.

Preferably, the CDR1, 2, and/or 3 of the engineered antibodies described above comprise the exact amino acid sequence(s) as those of 2F8 disclosed herein. However, the ordinarily skilled artisan will appreciate that some deviation from the exact CDR sequences of 2F8 may be possible while still retaining the ability of the antibody to bind EGFR effectively (e.g., conservative substitutions). Accordingly, in another embodiment, the engineered antibody may be composed of one or more CDRs that are, for example, 90%, 95%, 98% or 99.5% identical to one or more CDRs of 2F8.

In addition or alternative, to simply binding EGFR, engineered antibodies such as those described above may be selected for their retention of other functional properties of antibodies of the invention, such as:

(1) binding to live cells expressing EGFR;
(2) high affinity binding to EGFR;
(3) binding to a unique epitope on EGFR (to eliminate the possibility that monoclonal antibodies with complimentary activities when used in combination would compete for binding to the same epitope);
(4) opsonization of cells expressing EGFR; and/or
(5) mediation of growth inhibition, phagocytosis and/or killing of cells expressing EGFR in the presence of human effector cells.

Characterization of Binding of Human Monoclonal Antibodies to EGFR

To characterize binding of human monoclonal EGFR antibodies of the invention, sera from immunized mice can be tested, for example, by ELISA. Briefly, microtiter plates are coated with purified EGFR at 0.25 μg/ml in PBS, and then blocked with 5% bovine serum albumin in PBS. Dilutions of plasma from EGFR-immunized mice are added to each well and incubated for 1-2 hours at 37° C. The plates are washed with PBS/Tween and then incubated with a goat-anti-human IgG Fc-specific polyclonal reagent conjugated to alkaline phosphatase for 1 hour at 37° C. After washing, the plates are developed with pNPP substrate (1 mg/ml), and analyzed at OD of 405-650. Preferably, mice which develop the highest titers will be used for fusions.

An ELISA assay as described above can also be used to screen for hybridomas that show positive reactivity with EGFR immunogen. Hybridomas that bind with high avidity to EGFR will be subcloned and further characterized. One clone from each hybridoma, which retains the reactivity of the parent cells (by ELISA), can be chosen for making a 5-10 vial cell bank stored at −140° C., and for antibody purification.

To purify human anti-EGFR antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by $OD_{280}$ using 1.43 extinction coefficient. The monoclonal antibodies can be aliquoted and stored at −80° C.

To determine if the selected human anti-EGFR monoclonal antibodies bind to unique epitopes, each antibody can be biotinylated using commercially available reagents (Pierce, Rockford, Ill.). Competition studies using unlabeled monoclonal antibodies and biotinylated monoclonal antibodies can be performed using EGFR coated-ELISA plates as described above. Biotinylated MAb binding can be detected with a strep-avidin-alkaline phosphatase probe.

To determine the isotype of purified antibodies, isotype ELISAs can be performed. Wells of microtiter plates can be coated with 10 □g/ml of anti-human Ig overnight at 4° C. After blocking with 5% BSA, the plates are reacted with 10 □g/ml of monoclonal antibodies or purified isotype controls, at ambient temperature for two hours. The wells can then be reacted with either human IgG1 or human IgM-specific alkaline phosphatase-conjugated probes. Plates are developed and analyzed as described above.

In order to demonstrate binding of monoclonal antibodies to live cells expressing the EGFR, flow cytometry can be used. Briefly, cell lines expressing EGFR (grown under standard growth conditions) are mixed with various concentrations of monoclonal antibodies in PBS containing 0.1% Tween 80 and 20% mouse serum, and incubated at 37° C. for 1 hour. After washing, the cells are reacted with Fluorescein-labeled anti-human IgG antibody under the same conditions as the primary antibody staining. The samples can be analyzed by FACScan instrument using light and side scatter properties to gate on single cells. An alternative assay using fluorescence microscopy may be used (in addition to or instead of) the flow cytometry assay. Cells can be stained exactly as described above and examined by fluorescence microscopy. This method allows visualization of individual cells, but may have diminished sensitivity depending on the density of the antigen.

Anti-EGFR human IgGs can be further tested for reactivity with EGFR antigen by Western blotting. Briefly, cell extracts from cells expressing EGFR can be prepared and subjected to sodium dodecyl sulfate (SDS) polyacrylamide gel electrophoresis. After electrophoresis, the separated antigens will be transferred to nitrocellulose membranes, blocked with 20% mouse serum, and probed with the monoclonal antibodies to be tested. Human IgG binding can be detected using anti-human IgG alkaline phosphatase and developed with BCIP/NBT substrate tablets (Sigma Chem. Co., St. Louis, Mo.).

Phagocytic and Cell Killing Activities of Human Monoclonal Antibodies to EGFR

In addition to binding specifically to EGFR, human monoclonal anti-EGFR antibodies can be tested for their ability to mediate phagocytosis and killing of cells expressing EGFR. The testing of monoclonal antibody activity in vitro will provide an initial screening prior to testing in vivo models. Briefly, polymorphonuclear cells (PMN), or other effector cells, from healthy donors can be purified by Ficoll Hypaque density centrifugation, followed by lysis of contaminating erythrocytes. Washed PMNs, can be suspended in RPMI supplemented with 10% heat-inactivated fetal calf serum and mixed with $^{51}Cr$ labeled cells expressing EGFR, at various ratios of effector cells to tumor cells (-effector cells:tumor cells). Purified human anti-EGFR IgGs can then be added at various concentrations. Irrelevant human IgG can be used as negative control. Assays can be carried out for 0-120 minutes at 37° C. Samples can be assayed for cytolysis by measuring $^{51}Cr$ release into the culture supernatant. Anti-EGFR monoclonal can also be tested in combinations with each other to determine whether cytolysis is enhanced with multiple monoclonal antibodies.

Human monoclonal antibodies which bind to EGFR also can be tested in an in vivo model (e.g., in mice) to determine their efficacy in mediating phagocytosis and killing of cells expressing EGFR, e.g., tumor cells. These antibodies can be selected, for example, based on the following criteria, which are not intended to be exclusive:

1.) binding to live cells expressing EGFR;
2.) high affinity of binding to EGFR;
3.) binding to a unique epitope on EGFR (to eliminate the possibility that monoclonal antibodies with complimentary activities when used in combination would compete for binding to the same epitope);
4.) opsonization of cells expressing EGFR;
5.) mediation of growth inhibition, phagocytosis and/or killing of cells expressing EGFR in the presence of human effector cells.

Preferred human monoclonal antibodies of the invention meet one or more, and preferably all, of these criteria. In a particular embodiment, the human monoclonal antibodies are used in combination, e.g., as a pharmaceutical composition comprising two or more anti-EGFR monoclonal antibodies or fragments thereof. For example, human anti-EGFR monoclonal antibodies having different, but complementary activities can be combined in a single therapy to achieve a desired therapeutic or diagnostic effect. An illustration of this would be a composition containing an anti-EGFR human monoclonal antibody that mediates highly effective killing of target cells in the presence of effector cells, combined with another human anti-EGFR monoclonal antibody that inhibits the growth of cells expressing EGFR.

II. Production of Transgenic Nonhuman Animals Which Generate Human Monoclonal Anti-EGFR Antibodies In yet another aspect, the invention provides transgenic non-human animals, e.g., a transgenic mice, which are capable of expressing human monoclonal antibodies that specifically bind to EGFR, preferably with high affinity. In a preferred embodiment, the transgenic non-human animals, e.g., the transgenic mice (HuMAb mice), have a genome comprising a human heavy chain transgene and a light chain transgene. In one embodiment, the transgenic non-human animals, e.g., the transgenic mice, have been immunized with a purified or enriched preparation of EGFR antigen and/or cells expressing EGFR. Preferably, the transgenic non-human animals, e.g., the transgenic mice, are capable of producing multiple isotypes of human monoclonal antibodies to EGFR (e.g., IgG, IgA and/or IgE) by undergoing V-D-J recombination and isotype switching. Isotype switching may occur by, e.g., classical or non-classical isotype switching.

The design of a transgenic non-human animal that responds to foreign antigen stimulation with a heterologous antibody repertoire, requires that the heterologous immunoglobulin transgenes contain within the transgenic animal function correctly throughout the pathway of B-cell development. In a preferred embodiment, correct function of a heterologous heavy chain transgene includes isotype switching. Accordingly, the transgenes of the invention are constructed so as to produce isotype switching and one or more of the following: (1) high level and cell-type specific expression, (2) functional gene rearrangement, (3) activation of and response to allelic exclusion, (4) expression of a sufficient primary repertoire, (5) signal transduction, (6) somatic hypermutation, and (7) domination of the transgene antibody locus during the immune response.

Not all of the foregoing criteria need be met. For example, in those embodiments wherein the endogenous immunoglobulin loci of the transgenic animal are functionally disrupted, the transgene need not activate allelic exclusion. Further, in those embodiments wherein the transgene comprises a functionally rearranged heavy and/or light chain immunoglobulin gene, the second criteria of functional gene rearrangement is unnecessary, at least for that transgene which is already rearranged. For background on molecular immunology, see, *Fundamental Immunology,* 2nd edition (1989), Paul William E., ed. Raven Press, N.Y., which is incorporated herein by reference.

In certain embodiments, the transgenic non-human animals used to generate the human monoclonal antibodies of the invention contain rearranged, unrearranged or a combination of rearranged and unrearranged heterologous immunoglobulin heavy and light chain transgenes in the germline of the transgenic animal. Each of the heavy chain transgenes comprises at least one $C_H$ gene. In addition, the heavy chain transgene may contain functional isotype switch sequences, which are capable of supporting isotype switching of a heterologous transgene encoding multiple $C_H$ genes in the B-cells of the transgenic animal. Such switch sequences may be those which occur naturally in the germline immunoglobulin locus from the species that serves as the source of the transgene $C_H$ genes, or such switch sequences may be derived from those which occur in the species that is to receive the transgene construct (the transgenic animal). For example, a human transgene construct that is used to produce a transgenic mouse may produce a higher frequency of isotype switching events if it incorporates switch sequences similar to those that occur naturally in the mouse heavy chain locus, as presumably the mouse switch sequences are optimized to function with the mouse switch recombinase enzyme system, whereas the human switch sequences are not. Switch sequences may be isolated and cloned by conventional cloning methods, or may be synthesized de novo from overlapping synthetic oligonucleotides designed on the basis of published sequence information relating to immunoglobulin switch region sequences (Mills et al., *Nucl. Acids Res.* 15:7305-7316 (1991); Sideras et al., *Intl. Immunol.* 1:631-642 (1989), which are incorporated herein by reference).

For each of the foregoing transgenic animals, functionally rearranged heterologous heavy and light chain immunoglobulin transgenes are found in a significant fraction of the B-cells of the transgenic animal (at least 10 percent).

The transgenes used to generate the transgenic animals of the invention include a heavy chain transgene comprising DNA encoding at least one variable gene segment, one diversity gene segment, one joining gene segment and at least one constant region gene segment. The immunoglobulin light chain transgene comprises DNA encoding at least one variable gene segment, one joining gene segment and at least one constant region gene segment. The gene segments encoding the light and heavy chain gene segments are heterologous to the transgenic non-human animal in that they are derived from, or correspond to, DNA encoding immunoglobulin heavy and light chain gene segments from a species not consisting of the transgenic non-human animal. In one aspect of the invention, the transgene is constructed such that the individual gene segments are unrearranged, i.e., not rearranged so as to encode a functional immunoglobulin light or heavy chain. Such unrearranged transgenes support recombination of the V, D, and J gene segments (functional rearrangement) and preferably support incorporation of all or a portion of a D region gene segment in the resultant rearranged immunoglobulin heavy chain within the transgenic non-human animal when exposed to EGFR antigen.

In an alternate embodiment, the transgenes comprise an unrearranged "mini-locus." Such transgenes typically comprise a substantial portion of the C, D, and J segments as well as a subset of the V gene segments. In such transgene constructs, the various regulatory sequences, e.g., promoters, enhancers, class switch regions, splice-donor and splice-acceptor sequences for RNA processing, recombination signals and the like, comprise corresponding sequences derived from the heterologous DNA. Such regulatory sequences may be incorporated into the transgene from the same or a related species of the non-human animal used in the invention. For example, human immunoglobulin gene segments may be combined in a transgene with a rodent immunoglobulin enhancer sequence for use in a transgenic mouse. Alternatively, synthetic regulatory sequences may be incorporated into the transgene, wherein such synthetic regulatory sequences are not homologous to a functional DNA sequence that is known to occur naturally in the genomes of mammals. Synthetic regulatory sequences are designed according to consensus rules, such as, for example, those specifying the permissible sequences of a splice-acceptor site or a promoter/enhancer motif. For example, a minilocus comprises a portion of the genomic immunoglobulin locus having at least one internal (i.e., not at a terminus of the portion) deletion of a non-essential DNA portion (e.g., intervening sequence; intron or portion thereof) as compared to the naturally-occurring germline Ig locus.

In a preferred embodiment of the invention, the transgenic animal used to generate human antibodies to EGFR contains at least one, typically 2-10, and sometimes 25-50 or more copies of the transgene described in Example 12 of WO 98/24884 (e.g., pHC1 or pHC2) bred with an animal containing a single copy of a light chain transgene described in Examples 5, 6, 8, or 14 of WO 98/24884, and the offspring bred with the $J_H$ deleted animal described in Example 10 of WO 98/24884, the contents of which are hereby expressly incorporated by reference. Animals are bred to homozygosity for each of these three traits. Such animals have the following genotype: a single copy (per haploid set of chromosomes) of a human heavy chain unrearranged mini-locus (described in Example 12 of WO 98/24884), a single copy (per haploid set of chromosomes) of a rearranged human K light chain construct (described in Example 14 of WO 98/24884), and a deletion at each endogenous mouse heavy chain locus that removes all of the functional $J_H$ segments (described in Example 10 of WO 98/24884). Such animals are bred with mice that are homozygous for the deletion of the $J_H$ segments (Examples 10 of WO 98/24884) to produce offspring that are homozygous for the $J_H$ deletion and hemizygous for the human heavy and light chain constructs. The resultant animals are injected with antigens and used for production of human monoclonal antibodies against these antigens.

B cells isolated from such an animal are monospecific with regard to the human heavy and light chains because they contain only a single copy of each gene. Furthermore, they will be monospecific with regards to human or mouse heavy chains because both endogenous mouse heavy chain gene copies are nonfunctional by virtue of the deletion spanning the $J_H$ region introduced as described in Example 9 and 12 of WO 98/24884. Furthermore, a substantial fraction of the B cells will be monospecific with regards to the human or mouse light chains because expression of the single copy of the rearranged human κ light chain gene will allelically and isotypically exclude the rearrangement of the endogenous mouse K and lambda chain genes in a significant fraction of B-cells.

The transgenic mouse of the preferred embodiment will exhibit immunoglobulin production with a significant repertoire, ideally substantially similar to that of a native mouse. Thus, for example, in embodiments where the endogenous Ig genes have been inactivated, the total immunoglobulin levels will range from about 0.1 to 10 mg/ml of serum, preferably 0.5 to 5 mg/ml, ideally at least about 1.0 mg/ml. When a transgene capable of effecting a switch to IgG from IgM has been introduced into the transgenic mouse, the adult mouse ratio of serum IgG to IgM is preferably about 10:1. The IgG to IgM ratio will be much lower in the immature mouse. In general, greater than about 10%, preferably 40 to 80% of the spleen and lymph node B cells express exclusively human IgG protein.

The repertoire will ideally approximate that shown in a non-transgenic mouse, usually at least about 10% as high, preferably 25 to 50% or more. Generally, at least about a thousand different immunoglobulins (ideally IgG), preferably $10^4$ to $10^6$ or more, will be produced, depending primarily on the number of different V, J and D regions introduced into the mouse genome. These immunoglobulins will typically recognize about one-half or more of highly antigenic proteins, e.g., *staphylococcus* protein A. Typically, the immunoglobulins will exhibit an affinity for preselected antigens of at least about $10^7 M^{-1}$, preferably at least about $10^9 M^{-1}$, more preferably at least about $10^{10} M^{-1}$, $10^{-11} M^{-1}$, $10^{12} M^{-1}$, or greater, e.g., up to $10^{13} M^{-1}$ or greater.

In some embodiments, it may be preferable to generate mice with predetermined repertoires to limit the selection of V genes represented in the antibody response to a predetermined antigen type. A heavy chain transgene having a predetermined repertoire may comprise, for example, human VH genes which are preferentially used in antibody responses to the predetermined antigen type in humans. Alternatively, some VH genes may be excluded from a defined repertoire for various reasons (e.g., have a low likelihood of encoding high affinity V regions for the predetermined antigen; have a low propensity to undergo somatic mutation and affinity sharpening; or are immunogenic to certain humans). Thus, prior to rearrangement of a transgene containing various heavy or light chain gene segments, such gene segments may be readily identified, e.g., by hybridization or DNA sequencing, as being from a species of organism other than the transgenic animal.

The transgenic mice of the present invention can be immunized with a purified or enriched preparation of EGFR antigen and/or cells expressing EGFR as described previously. The mice will produce B cells which undergo class-switching via intratransgene switch recombination (cis-switching) and express immunoglobulins reactive with EGFR. The immunoglobulins can be human sequence antibodies, wherein the heavy and light chain polypeptides are encoded by human transgene sequences, which may include sequences derived by somatic mutation and V region recombinatorial joints, as well as germline-encoded sequences; these human sequence immunoglobulins can be referred to as being substantially identical to a polypeptide sequence encoded by a human $V_L$ or $V_H$ gene segment and a human $J_L$ or $J_L$ segment, even though other non-germline sequences may be present as a result of somatic mutation and differential V-J and V-D-J recombination joints. With respect to such human sequence antibodies, the variable regions of each chain are typically at least 80 percent encoded by human germline V, J, and, in the case of heavy chains, D, gene segments; frequently at least 85 percent of the variable regions are encoded by human germline sequences present on the transgene; often 90 or 95 percent or more of the variable region sequences are encoded by human germline sequences present on the transgene. However, since non-germline sequences are introduced by somatic mutation and VJ and VDJ joining, the human sequence antibodies will frequently have some variable region sequences (and less frequently constant region sequences) which are not encoded by human V, D, or J gene segments as found in the human transgene(s) in the germline of the mice. Typically, such non-germline sequences (or individual nucleotide positions) will cluster in or near CDRs, or in regions where somatic mutations are known to cluster.

The human sequence antibodies which bind to the predetermined antigen can result from isotype switching, such that human antibodies comprising a human sequence γ chain (such as γ1, γ2a, γ2B, or γ3) and a human sequence light chain (such as K) are produced. Such isotype-switched human sequence antibodies often contain one or more somatic mutation(s), typically in the variable region and often in or within about 10 residues of a CDR) as a result of affinity maturation and selection of B cells by antigen, particularly subsequent to secondary (or subsequent) antigen challenge. These high affinity human sequence antibodies may have binding affinities of at least $1 \times 10^9 M^{-1}$, typically at least $5 \times 10^9 M^{-1}$, frequently more than $1 \times 10^{10} M^{-1}$, and sometimes $5 \times 10^{10} M^{-1}$ to $1 \times 10^{11} M^{-1}$ or greater.

Another aspect of the invention pertains to the B cells from such mice which can be used to generate hybridomas expressing human monoclonal antibodies which bind with high affinity (e.g., greater than $2 \times 10^9 M^{-1}$) to EGFR. Thus, in another embodiment of the invention, these hybridomas are used to generate a composition comprising an immunoglobulin having an affinity constant ($K_A$) of at least $2 \times 10^9 M^{-1}$ for binding EGFR, wherein said immunoglobulin comprises:

a human sequence light chain composed of (1) a light chain variable region having a polypeptide sequence which is substantially identical to a polypeptide sequence encoded by a human $V_L$ gene segment and a human $J_L$ segment, and (2) a light chain constant region having a polypeptide sequence which is substantially identical to a polypeptide sequence encoded by a human $C_L$ gene segment; and a human sequence heavy chain composed of a (1) a heavy chain variable region having a polypeptide sequence which is substantially identical to a polypeptide sequence encoded by a human $V_H$ gene segment, optionally a D region, and a human $J_H$ segment, and (2) a constant region having a polypeptide sequence which is substantially identical to a polypeptide sequence encoded by a human $C_H$ gene segment.

The development of high affinity human monoclonal antibodies against EGFR is facilitated by a method for expanding the repertoire of human variable region gene segments in a transgenic mouse having a genome comprising an integrated human immunoglobulin transgene, said method comprising introducing into the genome a V gene transgene comprising V region gene segments which are not present in said integrated human immunoglobulin transgene. Often, the V region transgene is a yeast artificial chromosome comprising a portion of a human $V_H$ or $V_L$ ($V_K$) gene segment array, as may naturally occur in a human genome or as may be spliced together separately by recombinant methods, which may include out-of-order or omitted V gene segments. Often at least five or more functional V gene segments are contained on the YAC. In this variation, it is possible to make a transgenic mouse produced by the V repertoire expansion method, wherein the mouse expresses an immunoglobulin chain comprising a variable region sequence encoded by a V region gene segment present on the V region transgene and a C region encoded on the human Ig transgene. By means of the V repertoire expansion method, transgenic mice having at least 5 distinct V genes can be generated; as can mice containing at least about 24 V genes or more. Some V gene segments may be non-functional (e.g., pseudogenes and the like); these segments may be retained or may be selectively deleted by recombinant methods available to the skilled artisan, if desired.

Once the mouse germline has been engineered to contain a functional YAC having an expanded V segment repertoire, substantially not present in the human Ig transgene containing the J and C gene segments, the trait can be propagated and bred into other genetic backgrounds, including backgrounds where the functional YAC having an expanded V segment repertoire is bred into a mouse germline having a different human Ig transgene. Multiple functional YACs having an expanded V segment repertoire may be bred into a germline to work with a human Ig transgene (or multiple human Ig transgenes). Although referred to herein as YAC transgenes, such transgenes when integrated into the genome may substantially lack yeast sequences, such as sequences required for autonomous replication in yeast; such sequences may optionally be removed by genetic engineering (e.g., restriction digestion and pulsed-field gel electrophoresis or other suitable method) after replication in yeast in no longer necessary (i.e., prior to introduction into a mouse ES cell or mouse prozygote). Methods of propagating the trait of human sequence immunoglobulin expression, include breeding a transgenic mouse having the human Ig transgene(s), and optionally also having a functional YAC having an expanded V segment repertoire. Both $V_H$ and $V_L$ gene segments may be present on the YAC. The transgenic mouse may be bred into any background desired by the practitioner, including backgrounds harboring other human transgenes, including human Ig transgenes and/or transgenes encoding other human lymphocyte proteins. The invention also provides a high affinity human sequence immunoglobulin produced by a transgenic mouse having an expanded V region repertoire YAC transgene. Although the foregoing describes a preferred embodiment of the transgenic animal of the invention, other embodiments are contemplated which have been classified in four categories:

I. Transgenic animals containing an unrearranged heavy and rearranged light immunoglobulin transgene;

II. Transgenic animals containing an unrearranged heavy and unrearranged light immunoglobulin transgene;

III. Transgenic animal containing rearranged heavy and an unrearranged light immunoglobulin transgene; and IV. Transgenic animals containing rearranged heavy and rearranged light immunoglobulin transgenes.

Of these categories of transgenic animal, the preferred order of preference is as follows II>I>III>IV where the endogenous light chain genes (or at least the K gene) have been knocked out by homologous recombination (or other method) and I>II>III>IV where the endogenous light chain genes have not been knocked out and must be dominated by allelic exclusion.

III. Bispecific/Multispecific Molecules which Bind to EGFR

In yet another embodiment of the invention, human monoclonal antibodies to EGFR, or antigen-binding portions thereof, can be derivatized or linked to another functional molecule, e.g., another peptide or protein (e.g., an Fab' fragment) to generate a bispecific or multispecific molecule which binds to multiple binding sites or target epitopes. For example, an antibody or antigen-binding portion of the invention can be functionally linked (e.g., by chemical coupling, genetic fusion, noncovalent association or otherwise) to one or more other binding molecules, such as another antibody, antibody fragment, peptide or binding mimetic.

Accordingly, the present invention includes bispecific and multispecific molecules comprising at least one first binding specificity for EGFR and a second binding specificity for a second target epitope. In a particular embodiment of the invention, the second target epitope is an Fc receptor, e.g., human FcγRI (CD64) or a human Fcα receptor (CD89). Therefore, the invention includes bispecific and multispecific molecules capable of binding both to FcγR, FcαR or FcεR expressing effector cells (e.g., monocytes, macrophages or polymorphonuclear cells (PMNs)), and to target cells expressing EGFR. These bispecific and multispecific molecules target EGFR expressing cells to effector cell and, like the human monoclonal antibodies of the invention, trigger Fc receptor-mediated effector cell activities, such as phagocytosis of a EGFR expressing cells, antibody dependent cell-mediated cytotoxicity (ADCC), cytokine release, or generation of superoxide anion.

Bispecific and multispecific molecules of the invention can further include a third binding specificity, in addition to an anti-Fc binding specificity and an anti-EGFR binding specificity. In one embodiment, the third binding specificity is an anti-enhancement factor (EF) portion, e.g., a molecule which binds to a surface protein involved in cytotoxic activity and thereby increases the immune response against the target cell. The "anti-enhancement factor portion" can be an antibody, functional antibody fragment or a ligand that binds to a given molecule, e.g., an antigen or a receptor, and thereby results in an enhancement of the effect of the binding determinants for the $F_c$ receptor or target cell antigen. The "anti-enhancement factor portion" can bind an $F_c$ receptor or a target cell antigen. Alternatively, the anti-enhancement factor portion can bind to an entity that is different from the entity to which the first and second binding specificities bind. For example, the anti-enhancement factor portion can bind a cytotoxic T-cell (e.g., via CD2, CD3, CD8, CD28, CD4, CD40, ICAM-1 or other immune cell that results in an increased immune response against the target cell).

In one embodiment, the bispecific and multispecific molecules of the invention comprise as a binding specificity at least one antibody, or an antibody fragment thereof, including, e.g., an Fab, Fab', F(ab')$_2$, Fv, or a single chain Fv. The antibody may also be a light chain or heavy chain dimer, or any minimal fragment thereof such as a Fv or a single chain construct as described in Ladner et al. U.S. Pat. No. 4,946,778, issued Aug. 7, 1990, the contents of which is expressly incorporated by reference.

In one embodiment bispecific and multispecific molecules of the invention comprise a binding specificity for an FcαR or an FcγR present on the surface of an effector cell, and a second binding specificity for a target cell antigen, e.g., EGFR.

In one embodiment, the binding specificity for an Fc receptor is provided by a human monoclonal antibody, the binding of which is not blocked by human immunoglobulin G (IgG). As used herein, the term "IgG receptor" refers to any of the eight γ-chain genes located on chromosome 1. These genes encode a total of twelve transmembrane or soluble receptor isoforms which are grouped into three Fcγ receptor classes: FcγRI (CD64), FcγRII (CD32), and FcγRIII (CD16). In one preferred embodiment, the Fcγ receptor a human high affinity FcγRI. The human FcγRI is a 72 kDa molecule, which shows high affinity for monomeric IgG ($10^8$-$10^9$ M$^{-1}$).

The production and characterization of these preferred monoclonal antibodies are described by Fanger et al. in PCT application WO 88/00052 and in U.S. Pat. No. 4,954,617, the teachings of which are fully incorporated by reference herein. These antibodies bind to an epitope of FcγRI, FcγRII or FcγRIII at a site which is distinct from the Fcγ binding site of the receptor and, thus, their binding is not blocked substantially by physiological levels of IgG. Specific anti-FcγRI antibodies useful in this invention are MAb 22, MAb 32, MAb 44, MAb 62 and MAb 197. The hybridoma producing MAb 32 is available from the American Type Culture Collection, ATCC Accession No. HB9469. Anti-FcγRI MAb 22, F(ab')$_2$ fragments of MAb 22, and can be obtained from Medarex, Inc. (Annandale, N.J.). In other embodiments, the anti-Fcγ receptor antibody is a humanized form of monoclonal antibody 22 (H22). The production and characterization of the H22 antibody is described in Graziano, R. F. et al. (1995) J. Immunol. 155 (10): 4996-5002 and PCT/US93/10384. The H22 antibody producing cell line was deposited at the American Type Culture Collection on Nov. 4, 1992 under the designation HA022CL1 and has the accession no. CRL 11177.

In still other preferred embodiments, the binding specificity for an Fc receptor is provided by an antibody that binds to a human IgA receptor, e.g., an Fc-alpha receptor (FcαRI (CD89)), the binding of which is preferably not blocked by human immunoglobulin A (IgA). The term "IgA receptor" is intended to include the gene product of one α-gene (FcαRI) located on chromosome 19. This gene is known to encode several alternatively spliced transmembrane isoforms of 55 to 110 kDa. FcαRI (CD89) is constitutively expressed on monocytes/macrophages, eosinophilic and neutrophilic granulocytes, but not on non-effector cell populations. FcαRI has medium affinity ($\approx 5\times10^7$ M$^{-1}$) for both IgA1 and IgA2, which is increased upon exposure to cytokines such as G-CSF or GM-CSF (Morton, H. C. et al. (1996) Critical Reviews in Immunology 16:423-440). Four FcαRI-specific monoclonal antibodies, identified as A3, A59, A62 and A77, which bind FcαRI outside the IgA ligand binding domain, have been described (Monteiro, R. C. et al., 1992, J. Immunol. 148: 1764).

FcαRI and FcγRI are preferred trigger receptors for use in the invention because they are (1) expressed primarily on immune effector cells, e.g., monocytes, PMNs, macrophages and dendritic cells; (2) expressed at high levels (e.g., 5,000-100,000 per cell); (3) mediators of cytotoxic activities (e.g., ADCC, phagocytosis); (4) mediate enhanced antigen presentation of antigens, including self-antigens, targeted to them.

In other embodiments, bispecific and multispecific molecules of the invention further comprise a binding specificity which recognizes, e.g., binds to, a target cell antigen, e.g., EGFR. In a preferred embodiment, the binding specificity is provided by a human monoclonal antibody of the present invention.

An "effector cell specific antibody" as used herein refers to an antibody or functional antibody fragment that binds the Fc receptor of effector cells. Preferred antibodies for use in the subject invention bind the Fc receptor of effector cells at a site which is not bound by endogenous immunoglobulin.

As used herein, the term "effector cell" refers to an immune cell which is involved in the effector phase of an immune response, as opposed to the cognitive and activation phases of an immune response. Exemplary immune cells include a cell of a myeloid or lymphoid origin, e.g., lymphocytes (e.g., B cells and T cells including cytolytic T cells (CTLs)), killer cells, natural killer cells, macrophages, monocytes, eosinophils, neutrophils, polymorphonuclear cells, granulocytes, mast cells, and basophils. Some effector cells express specific Fc receptors and carry out specific immune functions. In preferred embodiments, an effector cell is capable of inducing antibody-dependent cell-mediated cytotoxicity (ADCC), e.g., a neutrophil capable of inducing ADCC. For example, monocytes, macrophages, which express FcR are involved in specific killing of target cells and presenting antigens to other components of the immune system, or binding to cells that present antigens. In other embodiments, an effector cell can phagocytose a target antigen, target cell, or microorganism. The expression of a particular FcR on an effector cell can be regulated by humoral factors such as cytokines. For example, expression of FcγRI has been found to be up-regulated by interferon gamma (IFN-γ). This enhanced expression increases the cytotoxic activity of FcγRI-bearing cells against targets. An effector cell can phagocytose or lyse a target antigen or a target cell.

"Target cell" shall mean any undesirable cell in a subject (e.g., a human or animal) that can be targeted by a composition (e.g., a human monoclonal antibody, a bispecific or a multispecific molecule) of the invention. In preferred embodiments, the target cell is a cell expressing or overexpressing EGFR. Cells expressing EGFR typically include tumor cells, such as bladder, breast, colon, kidney, ovarian, prostate, renal cell, squamous cell, lung (non-small cell), and head and neck tumor cells. Other EGFR-expressing cells include synovial fibroblast cells and keratinocytes which can be used as targets in the treatment of arthritis and psoriasis, respectively.

While human monoclonal antibodies are preferred, other antibodies which can be employed in the bispecific or multispecific molecules of the invention are murine, chimeric and humanized monoclonal antibodies.

Chimeric mouse-human monoclonal antibodies (i.e., chimeric antibodies) can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted. (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125,023; Better et al. (1988 Science 240:1041-1043); Liu et al. (1987) PNAS 84:3439-3443; Liu et al., 1987, J. Immunol. 139:3521-3526; Sun et al. (1987) PNAS 84:214-218; Nishimura et al., 1987, Canc. Res. 47:999-1005; Wood et al. (1985) Nature 314:446-449; and Shaw et al., 1988, J. Natl Cancer Inst. 80:1553-1559).

The chimeric antibody can be further humanized by replacing sequences of the Fv variable region which are not directly involved in antigen binding with equivalent sequences from human Fv variable regions. General reviews of humanized chimeric antibodies are provided by Morrison, S. L., 1985, *Science* 229:1202-1207 and by Oi et al., 1986, *BioTechniques* 4:214. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from 7E3, an anti-$GPII_bIII_a$ antibody producing hybridoma. The recombinant DNA encoding the chimeric antibody, or fragment thereof, can then be cloned into an appropriate expression vector. Suitable humanized antibodies can alternatively be produced by CDR substitution U.S. Pat. No. 5,225,539; Jones et al. 1986 Nature 321:552-525; Verhoeyan et al. 1988 Science 239:1534; and Beidler et al. 1988 J. Immunol. 141:4053-4060.

All of the CDRs of a particular human antibody may be replaced with at least a portion of a non-human CDR or only some of the CDRs may be replaced with non-human CDRs. It is only necessary to replace the number of CDRs required for binding of the humanized antibody to the Fc receptor.

An antibody can be humanized by any method, which is capable of replacing at least a portion of a CDR of a human antibody with a CDR derived from a non-human antibody. Winter describes a method which may be used to prepare the humanized antibodies of the present invention (UK Patent Application GB 2188638A, filed on Mar. 26, 1987), the contents of which is expressly incorporated by reference. The human CDRs may be replaced with non-human CDRs using oligonucleotide site-directed mutagenesis as described in International Application WO 94/10332 entitled, Humanized Antibodies to Fc Receptors for Immunoglobulin G on Human Mononuclear Phagocytes.

Also within the scope of the invention are chimeric and humanized antibodies in which specific amino acids have been substituted, deleted or added. In particular, preferred humanized antibodies have amino acid substitutions in the framework region, such as to improve binding to the antigen. For example, in a humanized antibody having mouse CDRs, amino acids located in the human framework region can be replaced with the amino acids located at the corresponding positions in the mouse antibody. Such substitutions are known to improve binding of humanized antibodies to the antigen in some instances. Antibodies in which amino acids have been added, deleted, or substituted are referred to herein as modified antibodies or altered antibodies.

The term modified antibody is also intended to include antibodies, such as monoclonal antibodies, chimeric antibodies, and humanized antibodies which have been modified by, e.g., deleting, adding, or substituting portions of the antibody. For example, an antibody can be modified by deleting the constant region and replacing it with a constant region meant to increase half-life, e.g., serum half-life, stability or affinity of the antibody. Any modification is within the scope of the invention so long as the bispecific and multispecific molecule has at least one antigen binding region specific for an FcγR and triggers at least one effector function.

Bispecific and multi specific molecules of the present invention can be made using chemical techniques (see e.g., D. M. Kranz et al. (1981) *Proc. Natl. Acad. Sci.* USA 78:5807), "polydoma" techniques (See U.S. Pat. No. 4,474,893, to Reading), or recombinant DNA techniques.

In particular, bispecific and multi specific molecules of the present invention can be prepared by conjugating the constituent binding specificities, e.g., the anti-FcR and anti-EGFR binding specificities, using methods known in the art and described in the examples provided herein. For example, each binding specificity of the bispecific and multispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-5-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl)cyclohaxane-1-carboxylate (sulfo-SMCC) (see e.g., Karpovsky et al. (1984) J. Exp. Med. 160:1686; Liu, M A et al. (1985) Proc. Natl. Acad. Sci. USA 82:8648). Other methods include those described by Paulus (Behring Ins. Mitt. (1985) No. 78, 118-132); Brennan et al. (Science (1985) 229:81-83), and Glennie et al. (J. Immunol. (1987) 139: 2367-2375). Preferred conjugating agents are SATA and sulfo-SMCC, both available from Pierce Chemical Co. (Rockford, Ill.).

When the binding specificities are antibodies (e.g., two humanized antibodies), they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific and multispecific molecule is a MAb×MAb, MAb×Fab, Fab×F(ab')$_2$ or ligand x Fab fusion protein. A bispecific and multispecific molecule of the invention, e.g., a bispecific molecule can be a single chain molecule, such as a single chain bispecific antibody, a single chain bispecific molecule comprising one single chain antibody and a binding determinant, or a single chain bispecific molecule comprising two binding determinants. Bispecific and multispecific molecules can also be single chain molecules or may comprise at least two single chain molecules. Methods for preparing bi- and multispecific molecules are described for example in U.S. Pat. No. 5,260,203; U.S. Pat. No. 5,455,030; U.S. Pat. No. 4,881,175; U.S. Pat. No. 5,132,405; U.S. Pat. No. 5,091,513; U.S. Pat. No. 5,476,786; U.S. Pat. No. 5,013,653; U.S. Pat. No. 5,258,498; and U.S. Pat. No. 5,482,858.

Binding of the bispecific and multi specific molecules to their specific targets can be confirmed by enzyme-linked immunosorbent assay (ELISA), a radioimmunoassay (RIA), FACS analysis, a bioassay (e.g., growth inhibition), or a Western Blot Assay. Each of these assays generally detects the presence of protein-antibody complexes of particular interest by employing a labeled reagent (e.g., an antibody) specific for the complex of interest. For example, the FcR-antibody complexes can be detected using e.g., an enzyme-linked antibody or antibody fragment which recognizes and specifically binds to the antibody-FcR complexes. Alternatively, the complexes can be detected using any of a variety of other immunoassays. For example, the antibody can be radioactively labeled and used in a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a γ counter or a scintillation counter or by autoradiography.

IV. Antibody Conjugates/Immunotoxins

In another aspect, the present invention features a human anti-EGFR monoclonal antibody, or a fragment thereof, conjugated to a therapeutic moiety, such as a cytotoxin, a drug or a radioisotope. When conjugated to a cytotoxin, these antibody conjugates are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). Other examples of therapeutic cytotoxins that can be conjugated to an antibody of the invention include calicheamicin and duocarmycin. An antibody of the present invention can be conjugated to a radioisotope, e.g., radioactive iodine, to generate cytotoxic radiopharmaceuticals for treating a EGFR-related disorder, such as a cancer The antibody conjugates of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

V. Pharmaceutical Compositions

In another aspect, the present invention provides a composition, e.g., a pharmaceutical composition, containing one or a combination of human monoclonal antibodies, or antigen-binding portion(s) thereof, of the present invention, formulated together with a pharmaceutically acceptable carrier. In a preferred embodiment, the compositions include a combination of multiple (e.g., two or more) isolated human antibodies or antigen-binding portions thereof of the invention. Preferably, each of the antibodies or antigen-binding portions thereof of the composition binds to a distinct, pre-selected epitope of EGFR.

In one embodiment, human anti-EGFR monoclonal antibodies having complementary activities are used in combination, e.g., as a pharmaceutical composition, comprising two or more human anti-EGFR monoclonal antibodies. For example, a human monoclonal antibody that mediates highly effective killing of target cells in the presence of effector cells can be combined with another human monoclonal antibody that inhibits the growth of cells expressing EGFR.

In another embodiment, the composition comprises one or a combination of bispecific or multispecific molecules of the invention (e.g., which contains at least one binding specificity for an Fc receptor and at least one binding specificity for EGFR).

Pharmaceutical compositions of the invention also can be administered in combination therapy, i.e., combined with other agents. For example, the combination therapy can include a composition of the present invention with at least one anti-tumor agent or other conventional therapy.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, bispecific and multispecific molecule, may be coated in a material to protect the compound from the action of acids and other natural conditions that may inactivate the compound.

A "pharmaceutically acceptable salt" refers to a salt that retains the desired biological activity of the parent compound and does not impart any undesired toxicological effects (see e.g., Berge, S. M., et al. (1977) J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A composition of the present invention can be administered by a variety of methods known in the art. As will be appreciated by the skilled artisan, the route and/or mode of administration will vary depending upon the desired results. The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al. (1984) *J. Neuroimmunol.* 7:27).

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

For the therapeutic compositions, formulations of the present invention include those suitable for oral, nasal, topical (including buccal and sublingual), rectal, vaginal and/or parenteral administration. The formulations may conveniently be presented in unit dosage form and may be prepared by any methods known in the art of pharmacy. The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent.

Formulations of the present invention which are suitable for vaginal administration also include pessaries, tampons, creams, gels, pastes, foams or spray formulations containing such carriers as are known in the art to be appropriate. Dosage forms for the topical or transdermal administration of compositions of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

When the compounds of the present invention are administered as pharmaceuticals, to humans and animals, they can be given alone or as a pharmaceutical composition containing, for example, 0.01 to 99.5% (more preferably, 0.1 to 90%) of active ingredient in combination with a pharmaceutically acceptable carrier.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. In general, a suitable daily dose of a compositions of the invention will be that amount of the compound which is the lowest dose effective to produce a therapeutic effect. Such an effective dose will generally depend upon the factors described above. It is preferred that administration be intravenous, intramuscular, intraperitoneal, or subcutaneous, preferably administered proximal to the site of the target. If desired, the effective daily dose of a therapeutic compositions may be administered as two, three, four, five, six or more sub-doses administered separately at appropriate intervals throughout the day, optionally, in unit dosage forms. While it is possible for a compound of the present invention to be administered alone, it is preferable to administer the compound as a pharmaceutical formulation (composition).

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the human monoclonal antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V.V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) FEBS Lett. 357:140; M. Owais et al. (1995) *Antimicrob. Agents Chemother.* 39:180); surfactant protein A receptor (Briscoe et al. (1995) *Am. J. Physiol.* 1233:134), different species of which may comprise the formulations of the inventions, as well as components of the invented molecules; p 120 (Schreier et al. (1994) *J. Biol. Chem.* 269:9090); see also K. Keinanen; M. L. Laukkanen (1994) FEBS Lett. 346:123; J. J. Killion; I. J. Fidler (1994) *Immunomethods* 4:273. In one embodiment of the invention, the therapeutic compounds of the invention are formulated in liposomes; in a more preferred embodiment, the liposomes include a targeting moiety. In a most preferred embodiment, the therapeutic compounds in the liposomes are delivered by bolus injection to a site proximal to the tumor or infection. The composition must be fluid to the extent that easy syringability exists. It must be stable under the conditions of manufacture and storage and must be preserved against the contaminating action of microorganisms such as bacteria and fungi.

A "therapeutically effective dosage" preferably inhibits tumor growth by at least about 20%, more preferably by at least about 40%, even more preferably by at least about 60%, and still more preferably by at least about 80% relative to untreated subjects. The ability of a compound to inhibit cancer can be evaluated in an animal model system predictive of efficacy in human tumors. Alternatively, this property of a composition can be evaluated by examining the ability of the compound to inhibit, such inhibition in vitro by assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

The composition must be sterile and fluid to the extent that the composition is deliverable by syringe. In addition to water, the carrier can be an isotonic buffered saline solution, ethanol, polyol (for example, glycerol, propylene glycol, and liquid polyetheylene glycol, and the like), and suitable mixtures thereof. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

When the active compound is suitably protected, as described above, the compound may be orally administered, for example, with an inert diluent or an assimilable edible carrier.

VI. Uses and Methods of the Invention

The compositions (e.g., human monoclonal antibodies to EGFR and derivatives/conjugates thereof) of the present invention have in vitro and in vivo diagnostic and therapeutic utilities. For example, these molecules can be administered to cells in culture, e.g., in vitro or ex vivo, or in a subject, e.g., in vivo, to treat, prevent or diagnose a variety of disorders. As used herein, the term "subject" is intended to include human and non-human animals. Preferred human animals include a human patient having disorder characterized by expression, typically aberrant expression (e.g., overexpression) of EGFR. For example, the methods and compositions of the present invention can be used to treat a subject with a tumorigenic disorder, e.g., a disorder characterized by the presence of tumor cells expressing EGFR including, for example, bladder, breast, colon, kidney, ovarian, prostate, renal cell, squamous cell, lung (non-small cell), and head and neck tumor cells. The methods and compositions of the present invention can be also be used to treat other disorders, e.g., autoimmune diseases, cancer, psoriasis, or inflammatory arthritis, e.g., rheumatoid arthritis, systemic lupus erythematosus-associated arthritis, or psoriatic arthritis. The term "non-human animals" of the invention includes all vertebrates, e.g., mammals and non-mammals, such as non-human primates, sheep, dog, cow, chickens, amphibians, reptiles, etc.

The compositions (e.g., human antibodies, multispecific and bispecific molecules) of the invention can be initially tested for binding activity associated with therapeutic or diagnostic use in vitro. For example, compositions of the invention can be tested using the ELISA and flow cytometric assays described in the Examples below. Moreover, the activity of these molecules in triggering at least one effector-mediated effector cell activity, including cytolysis of cells expressing EGFR can be assayed. Protocols for assaying for effector cell-mediated phagocytosis are described in the Examples below.

The compositions (e.g., human antibodies, multispecific and bispecific molecules) of the invention have additional utility in therapy and diagnosis of EGFR-related diseases. For example, the human monoclonal antibodies, the multispecific or bispecific molecules can be used, for example, to elicit in vivo or in vitro one or more of the following biological activities: to opsonize a cell expressing EGFR; to mediate phagocytosis or cytolysis of a cell expressing EGFR in the presence of human effector cells; to inhibit EGF or TGF-α induced autophosphorylation in a cell expressing EGFR; to inhibit autocrine EGF or TGF-α-induced activation of a cell expressing EGFR; or to inhibit the growth of a cell expressing EGFR, e.g., at low dosages.

In another embodiment, the human monoclonal antibodies of the present invention are unable to induce complement-mediated lysis of cells and, therefore, has fewer side effects in triggering complement-activated afflictions, e.g., acne. The primary cause of acne is an alteration in the pattern of keratinization within the follicle that produce sebum. Since keratinocytes express EGFR, interference with EGFR signaling processes in the skin can alter the growth and differentiation of the keratinocytes in the follicles which results in the formation of acne. Direct immunofluorescent studies have shown that in early non-inflamed and inflamed acne lesions there is activation of the classical and alternative complement pathways.

In a particular embodiment, the human antibodies and derivatives thereof are used in vivo to treat, prevent or diagnose a variety of EGFR-related diseases. Examples of EGFR-related diseases include a variety of cancers, such as bladder, breast, uterine/cervical, colon, pancreatic, colorectal, kidney, stomach, ovarian, prostate, renal cell, squamous cell, lung (non-small cell), esophageal, and head and neck cancer.

In another aspect the invention relates to a method of treating or preventing psoriasis, rheumatoid arthritis, systemic lupus erythematosus, psoriatic arthritis, Menetrier's disease, systemic sclerosis, Sjögren's syndrome, pulmonary fibrosis, bronchial asthma, myelofibrosis, diabetic nephropathy, chronic allograft rejection, chronic glomerulonephritis, Crohn's disease, ulcerative colitis, hepatic cirrhosis, sclerosing cholangitis, chronic uveitis, or cicatricial pemphigoid, as well as methods of treating or preventing Alzheimer's disease or other forms of dementia.

Methods of administering the compositions (e.g., human antibodies, multispecific and bispecific molecules) of the invention are known in the art. Suitable dosages of the molecules used will depend on the age and weight of the subject and the particular drug used. The molecules can be coupled to radionuclides, such as 131I, 90Y, 105Rh, indium-111, etc., as described in Goldenberg, D. M. et al. (1981) Cancer Res. 41: 4354-4360, and in EP 0365 997. In another aspect the invention relates to an immunoconjugate comprising an antibody according to the invention linked to a radioisotope, cytotoxic agent (e.g., calicheamicin and duocarmycin), a cytostatic agent, or a chemotherapeutic drug. The compositions (e.g., human antibodies, multispecific and bispecific molecules) of the invention can also be coupled to anti-infectious agents.

In another embodiment, the human anti-EGFR antibodies, or antigen binding fragments thereof, can be co-administered with a therapeutic agent, e.g., a chemotherapeutic agent, an immunosuppressive agent, an ant-inflammatory agent, or an ant-psoriasis agent, or can be co-administered with other known therapies, such as physical therapies, e.g., radiation therapy, hyperthermia, transplantation (e.g., bone marrow transplantation), surgery, sunlight, or phototherapy. Such therapeutic agents include, among others, anti-neoplastic agents such as doxorubicin (adriamycin), cisplatin bleomycin sulfate, carmustine, chlorambucil, and cyclophosphamide hydroxyurea which, by themselves, are only effective at levels which are toxic or subtoxic to a patient. Cisplatin is intravenously administered as a 100 mg/m$^2$ dose once every four weeks and adriamycin is intravenously administered as a 60-75 mg/m$^2$ dose once every 21 days.

Pharmaceutical compositions of the present invention can include one or more further chemotherapeutic agents selected from the group consisting of nitrogen mustards (e.g., cyclophosphamide and ifosfamide), aziridines (e.g., thiotepa), alkyl sulfonates (e.g., busulfan), nitrosoureas (e.g., carmustine and streptozocin), platinum complexes (e.g., carboplatin and cisplatin), non-classical alkylating agents (e.g., dacarbazine and temozolamide), folate analogs (e.g., methotrexate), purine analogs (e.g., fludarabine and mercaptopurine), adenosine analogs (e.g., cladribine and pentostatin), pyrimidine analogs (e.g., fluorouracil (alone or in combination with leucovorin) and gemcitabine), substituted ureas (e.g., hydroxyurea), antitumor antibiotics (e.g., bleomycin and doxorubicin), epipodophyllotoxins (e.g., etoposide and teniposide), microtubule agents (e.g., docetaxel and paclitaxel), camptothecin analogs (e.g., irinotecan and topotecan), enzymes (e.g., asparaginase), cytokines (e.g., interleukin-2 and interferon-α), monoclonal antibodies (e.g., trastuzumab and bevacizumab), recombinant toxins and immunotoxins (e.g., recombinant cholera toxin-B and TP-38), cancer gene therapies, physical therapies (e.g., hyperthermia, radiation therapy, and surgery) and cancer vaccines (e.g., vaccine against telomerase).

In another aspect the pharmaceutical composition comprises one or more further therapeutic agents selected from the group consisting of immunosuppressive antibodies (e.g., antibodies against MHC, CD2, CD3, CD4, CD7, CD28, B7, CD40, CD45, IFN-γ TNF-α, IL-4, IL-5, IL-6R, IL-7, IL-8, IL-10, CD11a, CD20, or CD58, or antibodies against their ligands) and other immunomodulatory compounds (e.g., soluble IL-15R or IL-10).

In another aspect the pharmaceutical composition comprises one or more further immunosuppressive agents selected from the group consisting of cyclosporine, azathioprine, mycophenolic acid, mycophenolate mofetil, corticosteroids (e.g., prednisone), methotrexate, gold salts, sulfasalazine, antimalarials, brequinar, leflunomide, mizoribine, 15-deoxyspergualine, 6-mercaptopurine, cyclophosphamide, rapamycin, tacrolimus (FK-506), OKT3, anti-thymocyte globulin.

In another aspect the pharmaceutical composition comprises one or more further anti-inflammatory agents selected from the group consisting of aspirin and other salicylates, steroidal drugs, NSAIDs (nonsteroidal anti-inflammatory drugs) (e.g., ibuprofen, fenoprofen, naproxen, sulindac, diclofenac, piroxicam, ketoprofen, diflunisal, nabumetone, etodolac, oxaprozin, and indomethacin), Cox-2 inhibitors (e.g., rofecoxib and celecoxib), and DMARDs (disease modifying antirheumatic drugs) (e.g., methotrexate, hydroxychloroquine, sulfasalazine, azathioprine, pyrimidine synthesis inhibitors (e.g., leflunomide), IL-1 receptor blocking agents (e.g., anakinra), TNF-α blocking agents (e.g., etanercept, infliximab and adalimumab), anti-IL-6R antibodies, CTLA4Ig, and anti-IL-15 antibodies).

In another aspect the pharmaceutical composition comprises one or more further anti-psoriasis agents selected from the group consisting of coal tar, A vitamin, anthralin, calcipotrien, tarazotene, corticosteroids, methotrexate, retinoids (e.g., acitretin), cyclosporine, etanercept, alefacept, efaluzimab, 6-thioguanine, mycophenolate mofetil, tacrolimus (FK-506), and hydroxyurea.

Co-administration of the human anti-EGFR antibodies, or antigen binding fragments thereof, of the present invention with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells which would render them unreactive with the antibody.

Target-specific effector cells, e.g., effector cells linked to compositions (e.g., human antibodies, multispecific and bispecific molecules) of the invention can also be used as therapeutic agents. Effector cells for targeting can be human leukocytes such as macrophages, neutrophils or monocytes. Other cells include eosinophils, natural killer cells and other IgG- or IgA-receptor bearing cells. If desired, effector cells can be obtained from the subject to be treated. The target-specific effector cells, can be administered as a suspension of cells in a physiologically acceptable solution. The number of cells administered can be in the order of $10^8$-$10^9$ but will vary depending on the therapeutic purpose. In general, the amount will be sufficient to obtain localization at the target cell, e.g., a tumor cell expressing EGFR, and to effect cell killing by, e.g., phagocytosis. Routes of administration can also vary.

Therapy with target-specific effector cells can be performed in conjunction with other techniques for removal of targeted cells. For example, anti-tumor therapy using the compositions (e.g., human antibodies, multispecific and bispecific molecules) of the invention and/or effector cells armed with these compositions can be used in conjunction with chemotherapy. Additionally, combination immunotherapy may be used to direct two distinct cytotoxic effector populations toward tumor cell rejection. For example, anti-EGFR antibodies linked to anti-Fc-gammaRI or anti-CD3 may be used in conjunction with IgG- or IgA-receptor specific binding agents.

Bispecific and multi specific molecules of the invention can also be used to modulate FcαR or FcγR levels on effector cells, such as by capping and elimination of receptors on the cell surface. Mixtures of anti-Fc receptors can also be used for this purpose.

The compositions (e.g., human antibodies, multi specific and bispecific molecules) of the invention which have complement binding sites, such as portions from IgG1, -2, or -3 or IgM which bind complement, can also be used in the presence of complement. In one embodiment, ex vivo treatment of a population of cells comprising target cells with a binding agent of the invention and appropriate effector cells can be supplemented by the addition of complement or serum containing complement. Phagocytosis of target cells coated with a binding agent of the invention can be improved by binding of complement proteins. In another embodiment target cells coated with the compositions (e.g., human antibodies, multi specific and bispecific molecules) of the invention can also be lysed by complement. In yet another embodiment, the compositions of the invention do not activate complement.

The compositions (e.g., human antibodies, multi specific and bispecific molecules) of the invention can also be administered together with complement. Accordingly, within the scope of the invention are compositions comprising human antibodies, multispecific or bispecific molecules and serum or complement. These compositions are advantageous in that the complement is located in close proximity to the human antibodies, multispecific or bispecific molecules. Alternatively, the human antibodies, multispecific or bispecific molecules of the invention and the complement or serum can be administered separately.

Compositions of the present invention can also include an expression vector comprising a nucleotide sequence encoding the variable region of a light chain, heavy chain or both light and heavy chains of a human antibody which binds EGFR, and further comprising a nucleotide sequence encoding the constant region of a light chain, heavy chain or both light and heavy chains of a human antibody which binds EGFR. In a particular embodiment, the invention relates to a pharmaceutical composition comprising an expression vector comprising a nucleotide sequence encoding heavy chain and light chain variable regions which comprise the amino acid sequences shown in SEQ ID NO:2 and SEQ ID NO:4, respectively, and conservative sequence modifications thereof.

Also within the scope of the invention are kits comprising the compositions (e.g., human antibodies, multispecific and bispecific molecules) of the invention and instructions for use. The kit can further contain a least one additional reagent, such as complement, or one or more additional human antibodies of the invention (e.g., a human antibody having a complementary activity which binds to an epitope in EGFR antigen distinct from the first human antibody).

In other embodiments, the subject can be additionally treated with an agent that modulates, e.g., enhances or inhibits, the expression or activity of Fcα or Fcγ receptors by, for example, treating the subject with a cytokine. Preferred cytokines for administration during treatment with the multispecific molecule include of granulocyte colony-stimulating factor (G-CSF), granulocyte-macrophage colony-stimulating factor (GM-CSF), interferon-γ (IFN-γ), and tumor necrosis factor (TNF).

In another embodiment, the subject can be additionally treated with a lymphokine preparation. Cancer cells which do not highly express EGFR can be induced to do so using lymphokine preparations. Lymphokine preparations can cause a more homogeneous expression of EGFRs among cells of a tumor which can lead to a more effective therapy. Lymphokine preparations suitable for administration include interferon-gamma, tumor necrosis factor, and combinations thereof. These can be administered intravenously. Suitable dosages of lymphokine are 10,000 to 1,000,000 units/patient.

The compositions (e.g., human antibodies, multispecific and bispecific molecules) of the invention can also be used to target cells expressing FcγR or EGFR, for example for labeling such cells. For such use, the binding agent can be linked to a molecule that can be detected. Thus, the invention provides methods for localizing ex vivo or in vitro cells expressing Fc receptors, such as FcγR, or EGFR. The detectable label can be, e.g., a radioisotope, a fluorescent compound, an enzyme, or an enzyme co-factor.

In one embodiment, the invention provides methods for detecting the presence of EGFR antigen in a sample, or measuring the amount of EGFR antigen, comprising contacting the sample, and a control sample, with a human monoclonal antibody, or an antigen binding portion thereof, which specifically binds to EGFR, under conditions that allow for formation of a complex between the antibody or portion thereof and EGFR. The formation of a complex is then detected, wherein a difference complex formation between the sample compared to the control sample is indicative the presence of EGFR antigen in the sample.

In still another embodiment, the invention provides a method for detecting the presence or quantifying the amount of Fc-expressing cells in vivo or in vitro. The method comprises (i) administering to a subject a composition (e.g., a multi- or bispecific molecule) of the invention or a fragment thereof, conjugated to a detectable marker; (ii) exposing the subject to a means for detecting said detectable marker to identify areas containing Fc-expressing cells.

The present invention is further illustrated by the following examples which should not be construed as further limiting. The contents of all figures and all references, patents and published patent applications cited throughout this application are expressly incorporated herein by reference.

EXAMPLES

Materials and Methods

Antigen:

Transgenic mice were immunized with the A431 Human epidermoid carcinoma cell line (CRL-1555, Lot 203945, ATCC Manassas, Va.) and with soluble epidermal growth factor receptor (EGFR) obtained from Sigma Chemical Co (product E 3641 lot 109H4108 and 20K4079). Soluble EGFR was stored at −20° to −80° C. until use.

Media Formulations:

(A) High Glucose DMEM (Mediatech Cellgro #10013) containing 10% FBS, Pennicillin-Streptomycin (Sigma P-7539), and 2-mercaptoethanol (GibcoBRL 21985-023) was used to culture A431 cells and myeloma cells. Additional media supplements were added to the Hybridoma growth media, which included: Origin-Hybridoma Cloning Factor (Igen 21001), OPI supplement (Sigma O-5003), HAT or HT (Sigma H 0262, H 0137). (B) Serum Free Medium contains DMEM, antibiotics and 2-mercaptoethanol only.

Cells for Immunization:

Cells for immunization were grown in DMEM (see above) to confluence on T-75 cell culture flasks, and were harvested with Trypsin EDTA (Cellgrow, Cat #25-053—Cl) solution 5-10 ml per flask. Cells recovered from flasks were resuspended in 50 ml of complete medium and then washed by three cycles of centrifugation (1000 G) and resuspended in 50 ml of sterile PBS. Mice were injected with $1\times10^7$ cells suspended in 0.5 ml of sterile PBS.

EGFR:

Soluble EGFR was mixed with Ribi adjuvant (Sigma, M 6536) in sterile PBS at a concentration of 25 µg EGFR/100 µl. Final tail vein immunizations were performed with soluble EGFR in sterile PBS.

Transgenic Mice:

Mice were housed in filter cages and were evaluated to be in good physical condition on the date of the fusion. Mice that produced the selected hybridomas were males 6-8 weeks old of the (CMD)++; (HCo7)11952+; (JKD)++; (KCo5)9272+ genotype (see Table 1).

TABLE 1

| Genotype Data* | | | | | | |
|---|---|---|---|---|---|---|
| Mouse | Sex | Born | Genotype | | | |
| 20241 | Male | Sep. 21, 1999 | CMD++ | (HCo7) 11952+ | (JKD)++ | (KCo5) 9272 |
| 20242 | Male | Sep. 21, 1999 | CMD++ | (HCo7) 11952+ | (JKD)++ | (KCo5) 9272 |
| 20243 | Male | Sep. 21, 1999 | CMD++ | (HCo7) 11952+ | (JKD)++ | (KCo5) 9272 |

*Individual transgene designations are in parentheses, followed by line numbers for randomly integrated transgenes. The symbols ++ and + indicate homozygous or hemizygous; however, because the mice are routinely screened using a PCR-based assay that does not allow us to distinguish between heterozygosity and homozygosity for the randomly integrated human Ig transgenes, a + designation may be given to mice that are actually homozygous for these elements.

Antibodies:

The following anti-EGFR MAbs were used in vitro and in vivo: 2F8 (also referred to as "Humax-EGFR"), a human IgG1 anti-EGFR antibody (Genmab, Utrecht, The Netherlands); the hybridoma producing m225, a mouse IgG2a anti-EGFR antibody, was obtained from American Type Culture Collection (ATCC, Rockville, Md., HB-8508); irrelevant human IgG isotype control (Genmab) which was used as an irrelevant IgG1 antibody; and fluorescein isothiocynate (FITC)-conjugated F(ab')$_2$ fragment of goat anti-mouse IgG (H+L) which was used as the secondary antibody for indirect immunofluorescence (Protos, San Francisco, Calif.), FITC-conjugated F(ab')$_2$ rabbit-α-human IgG (DAKO, Glostrup, Denmark).

The 2F8 hybridoma was cultured in DMEM (Gibco BRL, Life Technologies, Paisley, Scotland) supplemented with 10% Fetal bovine serum (FBS) (Hyclone, Logan, Utah) and 100 U/ml penicillin and 100 U/ml streptomycin (both Gibco BRL) (pen/strep). The m225 hybridoma was cultured in RPMI1640 (Gibco BRL) supplemented with 15% FBS (Hyclone) and pen/strep (both Gibco BRL). All cell lines were kept at 37° C. in humidified atmosphere containing 5% carbon dioxide. Humax antibody was purified using protein-A affinity chromatography followed by size exclusion on a HR200 column (Pharmacia, New Jersey). Mouse antibodies were purified using protein-G chromatography followed by size exclusion on a HR200 column. The purity of all antibodies was >95% as determined by dodecyl sulphate-polyacrylamide gel electrophoresis (SDS-PAGE). F(ab') fragments were made via pepsin or β-mercaptoethanol treatment followed by protein-A/G purification. Isolated F(ab') fragments were >95% pure as determined by SDS-PAGE.

Cell Lines:

A431, an epidermoid carcinoma which highly over-expresses EGFR, was obtained from the ATCC (Rockville, Md., CRL-155). The cells were cultured in RPMI 1640 medium (Gibco BRL), supplemented with 10% heat-inactivated FBS (Hyclone), 50 µg/ml streptomycin, 50 IU/ml penicillin, and 4 mM L-glutamine (all Gibco BRL). As the cells grow adherent they were detached by using trypsin-EDTA in PBS (Life Technologies, Paisley, Scotland). In tumor models, the cells are always used in log-phase. The cells are tested for stable EGFR expression and mycoplasma contamination before each experiment.

Fusion Procedure:

Spleens were aseptically harvested from freshly euthanized mice, and placed in 20-30 ml cold serum free media (SFM) in a petri plate. Adherent tissue was removed and spleens were rinsed twice in SFM. Spleen cells were gently harvested by homogenization in a tissue grinder in SFM.

Cells were centrifuged at 1000 g for 10 minutes and the red blood cells in the cell pellet were lysed by suspending the spleen cell pellet in 5 ml of ice cold 0.17 M NH$_4$Cl for 2-5 minutes. The cell mix was then diluted with 20 ml of SFM and centrifuged at 1000 g for 10 minutes. Myeloma cells were harvested into 50 ml centrifuge tubes. Spleen cells and myeloma cells were then washed by three cycles of centrifugation at 1000 g and resuspended in 30-40 ml of SFM.

After a cell count, spleen and myeloma cells were mixed at a 1:1 to 4:1 ratio spleen/myeloma. The spleen cell/myeloma cell mix was pelleted by centrifugation and the supernatant was removed by aspiration. The fusion was done by adding 1-2 ml of PEG solution (Sigma # P-7181) drop wise to the cell pellet over 45 seconds and gently mixing the solution for 75 seconds. The PEG solution was slowly diluted by adding 2 ml SFM drop wise over a minute. This was repeated with another 2 ml of SFM and then the solution was allowed to stand for 1 minute.

The solution was then slowly diluted with an additional 30 ml of SFM over 90 seconds. Cells were centrifuged at 1000 g and for 10 minutes and resuspended in 30 Ml of HAT medium. The fusion mix was diluted to 200-300 ml in HAT supplemented medium containing 3% Origin Hybridoma Cloning Factor, and dispersed into 96 well plates at >200 µl/well (~10-15 plates/spleen). Hybridoma plates were examined after 3-7 days for hybridomas. Plates were fed at 7 days by replacing half the medium in each well with fresh HT medium supplemented with 3% Origin. Plates were fed every 3-4 days thereafter with HT Medium.

ELISA Reagents:
1. Phosphate buffered saline (PBS), D-PBS without Ca and Mg, Hyclone D-PBS # SH30013.03, or Sigma P 3813.
2. PBS-T (wash buffer), PBS containing 0.05% Tween 20, Sigma P-1379.
3. PBS-T plus 1% BSA (Sigma A 9647). This serves as the blocking buffer and sample buffer.
4. ELISA plates, Nunc Immuno-plate F96 Maxisorp 442404.
5. Anti-human IgG γ-chain specific antibody, Jackson ImmunoRresearch #109-006-098.
6. Alkaline phosphatase labeled Goat anti-human γ-chain specific IgG, Jackson Immuno Research #109-056-098. An alternate is to use alkaline phosphatase labeled anti-human κ, Sigma A 3813.
7. Alkaline phosphatase labeled anti-human IgG1, or IgG3, Southern Biotechnology #9050-04 & 9210-04, for use in isotype specific ELISA.
8. p nitrophenyl (pNPP), Sigma N2765, or Sigma Fast tablet kit N-2770.
9. pNPP Substrate and buffer—Two options:
A. Diethanolamine buffer: Mix 97 ml of diethanolamine, Sigma D-2286, plus 0.1 g MgCl$_2$.6H$_2$O and 800 ml Di Water. Adjust the pH to 9.8 and adjust final volume to 1.0 L with Di water. Add one 20 mg tablet of pNPP, Sigma N-2765, per 20 ml diethanolamine buffer.
B. Sigma Fast pNPP Tablet Set, Sigma N-2770: Dissolve 1 buffer tablet and 1 pNPP tablet in 20 ml H$_2$O.
10. ELISA plate reader with 405 nm filter.
11. Epidermal growth factor receptor (EGFR), Sigma E 3641, Biotin labeled EGF (EGF-B), Molecular Probes E-3477.
12. Biotin labeled anti EGFR MAbs or human antibodies.
13. Nonspecific human antibodies for negative controls, or purified human IgG1 κ, Sigma I-I3889.
14. Automated ELISA plate washer: Titertek MAP C.

Anti Human IRG, κ ELISA:

To screen hybridoma plates for human IgG, κ producing MAbs, ELISA plates were coated with 1 µg/ml of anti-human IgG γ-chain specific antibody, Jackson ImmunoResesarch #109-006-098, overnight or longer at 4° C. Plates were washed in a plate washer and 100 µl/well PBS-T plus 1% BSA was added. Plates were incubated at least 15 minutes and 10-50 µl of cell culture supernatant was added to ELISA plate wells with a few wells in each plate included with IgG as a positive control and cell culture medium as a negative control. Plates were incubated 1-2 hr at room temperature, washed, and alkaline phosphatase labeled anti-Human κ antibody (Sigma A-3813) 1:5000 in PBS-T plus 1% BSA was added. Plates were incubated for 1 hr at room temperature, washed 4 times in a plate washer, and pNPP substrate was added. Plates were incubated 10-60 minutes and absorbance was read at 405 nm in an ELISA plate reader.

ELISA Procedure for Testing Specificity of Anti-EGFR Human Antibodies—Direct Binding of Antibody to EGFR Coated ELISA Plates:

To verify that anti-EGFR antibodies specifically bind to EGFR, Nunc Maxisorp plates were coated with 100 µl/well of EGFR at 0.4 µl g/ml in PBS overnight at 4° C. or for 2 hr at room temperature. Plates were washed in PBS-T three times, 100 µl/well of PBS-T plus 1% BSA was added to block nonspecific sites on the plastic surface, and incubated at least 15 minutes before loading samples. Dilutions of samples to be tested were loaded in PBS-T plus 1% BSA. Supernatants were diluted a minimum of 1:3 in PBS-T 1% BSA for loading into ELISA plates. Samples and standards were loaded at 100 µl well, incubated for 1 hr at room temperature, and plates were washed three times in PBS-T. 100 µl/well of PBS-T 1% BSA containing alkaline phosphatase labeled goat antihuman γ specific antibody at a 1:3000 to 1:5000 dilution was added. Alternatively, alkaline phosphatase labeled anti-human κ can be used. Plates were incubated 1 hr at room temp, washed 4 times, and pNPP substrate was added. A absorbance was read at 405 nm.

ELISA Procedure for Testing Specificity of Anti-EGFR Human Antibodies—ELISA EGF/EGFR Blocking Assay:

To verify that anti-EGFR antibody binds to EGFR and additionally blocks the binding of biotin labeled epidermal growth factor to the Epidermal growth factor receptor (EGFR), Nunc Maxisorp plates were coated with 100 µl/well of EGFR at 0.4 µg/ml in PBS overnight at 4° C. or for 2 hr at room temperature. Plates were washed in PBS-T three times, 100 µl/well of PBS-T plus 1% BSA was added to block nonspecific sites on the plastic surface, and incubated at least 15 minutes before loading samples. Dilutions of samples to be tested were loaded in PBS-T plus 1% BSA. Supernatants were diluted a minimum of 1:3 in PBS-T 1% BSA for loading into ELISA plates. Samples and standards were loaded at 100 µl well, incubated for 30 minutes at room temperature, and 20 µl/well of Biotin labeled EGF at 0.5 µg/ml was added and plates were incubated for 1 hr (this is added to the sample solution already on the plates). Alternatively, samples can be incubated for 1 hr, washed, and 100 µl/well EGF-biotin at 0.1 µg/ml added and incubated for 1 hr. Plates were washed 3 times, 100 µl/well of PBS-T 1% BSA containing streptavidin alkaline phosphatase at 1:2000 dilution was added, and incubated 1 hr. Plates were washed 4 times, pNPP substrate was added, and absorbance was read at 405 nm.

Competitive ELISA for Determining Epitope Specificity of Anti-EGFR Human Antibodies—Competition with Commercial Murine MAbs 225, 528, AB5, and 29.1:

This assay was performed to determine which MAbs are most like antibodies 225, 528, AB5 and 29.1. MAbs 225, 528, and AB5 block EGF binding to its receptor and inhibit in-vivo endogenous tyrosine kinase activity of EGFR. MAb 29.1 is a non blocking MAb that binds to a carbohydrate residue of EGFR. Plates were coated for at least 2 hr at room temperature, or overnight at 4° C., with 0.4 µg/ml of EGFR in PBS and washed and blocked with 100 µl/well of PBS-T 1% BSA. The blocking solution was flicked out and 100 µl/well of PBS-T-1% BSA was added to columns 1-6 on the left side of the plate while an unlabeled mouse MAb at 1 µg/ml (100 µl/well) was added to the right side of the plate in columns 7-12. Plates were incubated at room temperature for 1 hour and 25 µl of cell culture supernatant was added to the equivalent position of each half of the plate so that each supernatant is loaded onto one well with PBS-T-1% BSA and one well with mouse MAb. Plates were incubated 1 hr, washed, and alkaline phosphatase labeled anti-Human IgG Fc antibody was added. Plates were incubated 1 hr. Plates were washed and substrate was added. Absorbence was read at 405 nm. The % competition from MAb was determined by the following formula: (OD supernatant without competition—OD supernatant with MAb competition/OD supernatant without competition)×100.

Competitive ELISA for Determining Epitope Specificity of Anti-EGFR Human Antibodies—Competitive ELISA with Biotin Labeled Human Antibodies:

Competitive ELISA assays were also performed to determine the specificity of the anti-EGFR human antibodies. Plates were coated for at least 2 hr at room temperature, or overnight at 4° C., with 0.4 µg/ml of EGFR in PBS. Plates were washed and blocked with 100 µl/well of PBS-T 1% BSA. 50 µl of (10-30 µg/ml) of unlabeled human antibodies or mouse MAbs was added to the top well(s) of the plate column and 50 µl was sequentially transferred and mixed serially down each column to create a three fold dilution series of each antibody. 50 µl was discarded from the bottom well after mixing. Plates were incubated for 1 hr and 20 µ/well of biotinylated anti-EGFR human antibody or unlabeled mouse anti-Human EGFR antibodies was added to the entire plate so that the final concentration of competing antibody was approximately 0.1-0.2 µg/ml. Plates were incubated for 1 hour at room temperature, washed, and 100 µl/well streptavidin alkaline phosphatase (1:2000 in PBS-T-BSA) or Alkaline phosphatase labeled goat anti-Mouse IgG was added. Plates were incubated 1 hour, washed, and substrate was added. Absorbence was read at 405 nm.

FACS Procedure for Testing Specificity of Anti-EGFR Human Antibodies—EGF/EGFR Blocking:

This assay was used to verify that anti-EGFR antibody binds to EGFR on the cell surface, and by doing so, blocks the binding of biotin labeled epidermal growth factor (EGF-B) to the Epidermal growth factor receptor (EGFR). This FACS based method uses the human epidermal carcinoma cell line A431 which expresses about $10^6$ EGFR molecules/cell.

Materials for EGFR FACS assays:
1. A431 cells (ATCC CRL 1555) confluent in one or more T-175 flasks. A 431 cells are cultured in DMEM plus 10% FCS.
2. Trypsin-EDTA solution, Sigma T-3924.
3. Biotin labeled EGF. Prepare a stock solution of about 5 µg/ml, use 10 µl/well.
4. Round bottomed 96 well plates.
5. PBS, sterile.
6. PBS plus 1% BSA plus 0.02% sodium azide (FACS buffer).
7. PE-labeled Streptavidin, Sigma S 3402. Dilute 1:20 in FACS buffer.
8. PE-labeled or FITC labeled anti human IgG, FC γ specific, Pharminigen 34164X, 34165X.
9. Low speed centrifuge with swinging buckets and adapter for 96 well plates (Beckman).
10. FACS
11. BD FACS tubes.

Procedure:
A431 cells were harvested by trypsin EDTA treatment. Medium from tissue culture flask was removed and flask was rinsed briefly with 10-20 ml sterile PBS or HBSS. 5-10 ml of trypsin EDTA was added and flask was returned to incubator for a few minutes. As cells began to detach from the plastic surface, a 10 ml pipette was used to gently syringe the cells from the plastic surface and to generate a single cell suspension without too many cell clumps. Cells were transferred to a 50 ml tube with 20-30 ml of cell culture medium (with FBS), centrifuged for 10 min at 1000 g, and washed twice by centrifugation and resuspension of cells in cold FACS buffer. Cell solution was filtered through a nylon mesh to remove cell clumps (the top of BD FACS tubes are equipped for this). Cells were counted and the volume was adjusted so that there are between 1 to $5 \times 10^6$ cells ml. Cells were dispensed into a round bottom 96 well plate at about 200,000 cells/well and centrifuged for about 1 min at 1000 g and then the liquid was flicked out (cells should remain in well bottom). Plates were kept on ice or at 4° C. In a separate 96-well plate, antibody sample dilutions in FACS buffer was prepared by preparing a three fold dilution series of antibody starting at 10 µg/ml and decreasing to 4.5 ng/ml. 100 µl of each antibody dilution, isotype controls, and buffer controls was added to the round bottom plate. The antibody samples and controls were mixed with the cells and incubated for 30 minutes on ice. 10 µl of biotin labeled EGF was added to the antibody cell solution and incubated an additional 30 minutes. The cells were washed three times by centrifugation and resuspension in FACS buffer. 50 μl well of Streptavadin PE was added, mixed, and incubated for 30 minutes on ice. The cells were washed three times and resuspended in 50 μl FACS buffer. The contents of each well were transferred to a tube containing 300-400 μl FACS buffer. 5000-10000 cells were analyzed in each sample by FACS in the FL-2 channel. MCF versus Antibody concentration was plotted.

Human or Animal Derived Materials:

A431 Human epidermoid carcinoma cell line (CRL-1555, Lot 203945, ATCC Manassas, Va.). Trypsin EDTA (Cellgrow Cat #25-053-Cl). P3 X63 ag8.653 myeloma cell line: ATCC CRL 1580, lot F-15183 Origin-Hybridoma Cloning Factor (Igen 21001). OPI supplement (Sigma 0-5003) Fetal bovine serum (SH30071 lot #s ALE10321, and AGH6843) from Hyclone, Logan, Utah. Origen Freeze Medium (Igen, #210002)

ELISA:

For determining the binding of human antibodies to EGFR, an ELISA with EGFR (Sigma, St Louis, M) coated overnight in a concentration of 1 μg/ml in PBS on a 96-wells microtiter plate (Greiner, Frickenhausen, Germany) was used. After blocking the plate with ELISA buffer (PBS/0.05% Tween 20 and 1% chicken serum (Gibco BRL)) at a concentration of 100 μl/well, monoclonal antibody diluted in ELISA buffer was added and incubated for 1 hour at 37° C. The plates were subsequently washed 3 times and incubated with peroxidase labeled goat anti-human IgG Fc specific (Jackson, West Grace, P) for 1 hour at 37° C. The assay was developed with ABTS (Roche Diagnostics, Mannheim, Germany) for 30 minutes. Absorbance was measured with a microplate reader (Biotek, Winooski, Canada) at 415 nm. With regard to blocking studies, the plates were pre-incubated for 10 minutes with 50 μl blocking agent in ELISA buffer before adding 50 μl fully human antibody. For determining human IgG in mouse serum ELISA plates were coated with rabbit anti-human kappa, light chains (DAKO) overnight in PBS in a 96-wells microtiter plate (Greiner). After blocking the plate with ELISA buffer (PBS/0.05% Tween20 and 1% chicken serum) 100 μl/well, mouse serum diluted in ELISA buffer was added and incubated for 1 hour at 37° C. The plates were subsequently washed 3 times and incubated with peroxidase labeled rabbit F(ab')$_2$ fragments anti human IgG (DAKO) for 1 hour at 37° C. The assay was developed with ABTS (Roche) for 30 minutes. Absorbance was measured with a microplate reader (Biotek) at 415 nm.

Flow Cytometry:

EGFR over expressing tumor cells were incubated with MAb for 30 minutes at 4° C. Cells were washed three times in phosphate buffered saline supplemented with 1% bovine serum albumin (Roche) and 0.01% azide. Counter-staining was performed with FITC-conjugated F(ab')$_2$ fragments of a goat anti-mouse antibody or with FITC-conjugated F(ab')$_2$ fragments of a rabbit anti-human IgG antibody. With regard to inhibition experiments, the cells were pre incubated with EGF or TGF-α for 10 minutes at 4° C. All samples were analyzed on a FACScan flowcytometer (Becton-Dickinson, San Jose, Calif.).

Phosphorylation Studies:

Sub-confluent cultures of A431 cells in 24-wells plates (NUNC, Kamstrup, Denmark) were treated overnight with low serum conditions (0.5%). Different antibody dilutions were added to the wells and incubated for 30 minutes at 37° C. and 5% carbon dioxide. Cells were stimulated with or without 5 ng/ml EGF (Prepotech, Rocky Hill, N.J.) for 5 min at 37° C. and 5% carbon dioxide. Cell extracts were prepared as described by Tomic et al. (Tomic et al, 1995) using 100 μl of lysis buffer per well. Fifty μl of A431 cell extract was analyzed by sodium SDS-PAGE and immunoblotting with anti-phospho-tyrosine antibodies (PY20, Transduction Laboratories, Kentucky), goat anti mouse IgG-HRP antibodies (Transduction Laboratories), and ECL detection. For stimulation with TGF-α (Prepotech, Rocky Hill, N.J.) sub-confluent cultures of A431 cells in 24 well plates (Nunc) were treated overnight with low-serum medium (0.5%). Antibodies were added in a fixed dose of 10 or 0 μg/ml and incubated as described as above. The cells were stimulated with an increasing amount TGF-α. Cells were treated as above.

In Vitro Cell Growth Inhibition:

Cell growth inhibition features of fully human antibodies were evaluated with a non-radioactive inhibition assay. Briefly, 100 μl of 2×10$^4$/ml A431 cells was added to flat-bottomed tissue culture plates and placed in a cell culture incubator. After 2 hours 100 μl antibody dilution was added and placed back in the cell culture incubator. The cells were incubated for 6-7 days, supernatants were decanted, and 100 μl 0.25% glutaraldehyde in PBS was added to each well. After incubation for 45 minutes at room temperature the wells were washed two times with demi-water. 50 μl of 1% crystal violet in demi-water was added and incubated for 15 minutes at room temperature. After washing the plate twice with demi-water, the plates were developed with 100% methanol during 30 minutes on a plate shaker. Absorbance was measured with a microplate reader using a 550 nm filter with a 650 nm reference filter. Inhibition is measured in triplicates. Percentage of relative cell proliferation was determined by dividing the average absorbance from the triplicate of a particular antibody concentration by the average absorbance from wells which had no antibody added, then times 100.

Effector Cell Isolation:

Peripheral white blood cells were isolated by a method slightly modified from that described in Repp, et al. (1991) Blood 78: 885-889. Briefly, heparin-anticoagulated blood was layered over a ficoll gradient. After centrifugation, effector cells were harvested from the interphase and the remaining erythrocytes were removed by hypotonic lysis. Cytospin preparations were used to assess the purity of isolated cells which was higher than 95%. The viability of cells, determined by trypan blue exclusion, exceeded 95%.

ADCC Assays:

The capacity of fully human antibodies to lyse tumor cells was evaluated in $^{51}$Chromium release assays (Valerius, et al. (1993) Blood, 82: 931-939). Isolated human white blood cells were used as effector source. In brief, tumor targets were incubated with 100 μCi $^{51}$Cr for two hours. After a three times wash with culture medium, 5×10$^3$ target cells were added to round-bottomed tissue culture plates containing 50 μl of isolated effector cells and sensitizing MAb in different concentrations and diluted in culture medium. The final volume was 200 μl and the effector to target cell ratio (E:T) 80:1. The assays were incubated overnight at 37° C. and stopped by centrifugation. The chromium release was measured in supernatants in triplicates. Percentage of cellular cytotoxicity was calculated using the formula:

$$\% \text{ Specific Lysis} = \frac{\text{Experimental } cpm - \text{Spontaneous } cpm}{\text{Maximum } cpm - \text{Spontaneous } cpm} \times 100$$

with maximal $^{51}$Cr release determined by adding ZAP-oglobin® (10% final concentration) to target cells and basal release measured in the absence of sensitizing antibodies and effector cells. Only very low levels of antibody mediated, non-cellular cytotoxicity (without effector cells) was observed under these assay conditions (<5% specific lysis).

Affinity Measurements Using SPR Technology:

Binding affinity of anti EGFR antibodies was determined using BIAcore 300 (Biacore, Upsula, Sweden). EGFR purified from A431 cells purchased from Sigma was immobilized on a CM5 chip according to the manufacturer's instructions. Measurements were done with antibody F(ab') fragments at different concentrations. Association and dissociation constants were determined using BIAevaluation software (version 3.1).

Mice and Tumor Models:

Nude Balb/c mice (NuNu) were purchased from Harlan (Horst, The Netherlands). All experiments described were performed with female mice of eight to twelve weeks old. Mice were housed in the Transgenic Mouse Facility of the Central Laboratory Animal Facility (Utrecht, The Netherlands) and experiments were approved by the Utrecht University animal ethics committee. When participating in an experiment, mice were checked thrice a week for signs of toxicity and discomfort including level of activity, skin abnormalities, diarrhea, and general appearance. A well-established subcutaneous (s.c.) tumor model was used. Briefly the high EGFR expressing A431 cells were inoculated, on the right side of the mouse, at a dose of $3 \times 10^6$ cells. The tumors grow uniform and can be easily measured by vernier calipers. The tumor volume is reported as length×width×height (in $mm^3$). The monoclonal antibodies were injected intraperitoneally (i.p.) according to the study protocol. The tumor cells were tested for stable EGFR expression after in vivo passage by flow cytometry and immunohistochemistry. In order to determine pharmacokinetics, mice, with and without tumors, were injected i.p. with 2F8 antibody. Weekly blood samples were taken via the tail vein before and for six weeks after the injection. The samples were analyzed by human IgG ELISA.

Statistical Analysis:

Group data are reported as mean±standard error of the mean (SEM). Differences between groups are analyzed by unpaired (or, where appropriate, paired) Student's t-test. Levels of significance are indicated. Significance was accepted at the $p<0.05$ level.

Example 1

Generation of Cmu Targeted Mice for the Production of Anti-EGFR Human Antibodies, Also Referred to as "HuMabs"

Construction of a CMD Targeting Vector

The plasmid pICEmu contains an EcoRI/XhoI fragment of the murine Ig heavy chain locus, spanning the mu gene, that was obtained from a Balb/C genomic lambda phage library (Marcu et al. Cell 22: 187, 1980). This genomic fragment was subcloned into the XhoI/EcoRI sites of the plasmid pICEMI9H (Marsh et al; Gene 32, 481-485, 1984). The heavy chain sequences included in pICEmu extend downstream of the EcoRI site located just 3' of the mu intronic enhancer, to the XhoI site located approximately 1 kb downstream of the last transmembrane exon of the mu gene; however, much of the mu switch repeat region has been deleted by passage in *E. coli*. The targeting vector was constructed as follows. A 1.3 kb HindIII/SmaI fragment was excised from pICEmu and subcloned into HindIII/SmaI digested pBluescript (Stratagene, La Jolla, Calif.). This pICEmu fragment extends from the HindIII site located approximately 1 kb 5' of Cmu1 to the SmaI site located within Cmu1. The resulting plasmid was digested with SmaI/SpeI and the approximately 4 kb SmaI/XbaI fragment from pICEmu, extending from the SmaI site in Cmu1 3' to the XbaI site located just downstream of the last Cmu exon, was inserted. The resulting plasmid, pTAR1, was linearized at the SmaI site, and a neo expression cassette inserted. This cassette consists of the neo gene under the transcriptional control of the mouse phosphoglycerate kinase (pgk) promoter (XbaI/TaqI fragment; Adra et al. (1987) Gene 60: 65-74) and containing the pgk polyadenylation site (PvuII/HindIII fragment; Boer et al. (1990) Biochemical Genetics 28: 299-308). This cassette was obtained from the plasmid pKJ1 (described by Tybulewicz et al. (1991) Cell 65: 1153-1163) from which the neo cassette was excised as an EcoRI/HindIII fragment and subcloned into EcoRI/HindIII digested pGEM-7Zf (+) to generate pGEM-7 (KJ1). The neo cassette was excised from pGEM-7 (KJ1) by EcoRI/SalI digestion, blunt ended and subcloned into the SmaI site of the plasmid pTAR1, in the opposite orientation of the genomic Cmu sequences. The resulting plasmid was linearized with Not I, and a herpes simplex virus thymidine kinase (tk) cassette was inserted to allow for enrichment of ES clones bearing homologous recombinants, as described by Mansour et al. (1988) Nature 336: 348-352. This cassette consists of the coding sequences of the tk gene bracketed by the mouse pgk promoter and polyadenylation site, as described by Tybulewicz et al. (1991) Cell 65: 1153-1163. The resulting CMD targeting vector contains a total of approximately 5.3 kb of homology to the heavy chain locus and is designed to generate a mutant mu gene into which has been inserted a neo expression cassette in the unique SmaI site of the first Cmu exon. The targeting vector was linearized with PvuI, which cuts within plasmid sequences, prior to electroporation into ES cells.

Generation and Analysis of Targeted ES Cells

AB-1 ES cells (McMahon, A. P. and Bradley, A., (1990) Cell 62: 1073-1085) were grown on mitotically inactive SNL76/7 cell feeder layers (ibid.) essentially as described (Robertson, E. J. (1987) in *Teratocarcinomas and Embryonic Stem Cells: a Practical Approach* (E. J. Robertson, ed.) Oxford: IRL Press, p. 71-112). The linearized CMD targeting vector was electroporated into AB-1 cells by the methods described Hasty et al. (Hasty, P. R. et al. (1991) Nature 350: 243-246). Electroporated cells were plated into 100 mm dishes at a density of $1-2 \times 10^6$ cells/dish. After 24 hours, G418 (200 micrograms/ml of active component) and FIAU ($5 \times 10^{-7}$ M) were added to the medium, and drug-resistant clones were allowed to develop over 8-9 days. Clones were picked, trypsinized, divided into two portions, and further expanded. Half of the cells derived from each clone were then frozen and the other half analyzed for homologous recombination between vector and target sequences.

DNA analysis was carried out by Southern blot hybridization. DNA was isolated from the clones as described Laird et al. (Laird, P. W. et al., (1991) Nucleic Acids Res. 19: 4293). Isolated genomic DNA was digested with SpeI and probed with a 915 bp SacI fragment, probe A, which hybridizes to a sequence between the mu intronic enhancer and the mu switch region. Probe A detects a 9.9 kb SpeI fragment from the wild type locus, and a diagnostic 7.6 kb band from a mu locus which has homologously recombined with the CMD targeting vector (the neo expression cassette contains a SpeI site). Of 1132 G418 and FIAU resistant clones screened by Southern blot analysis, 3 displayed the 7.6 kb SpeI band indicative of homologous recombination at the mu locus. These 3 clones were further digested with the enzymes BglI, BstXI, and EcoRI to verify that the vector integrated homologously into the mu gene. When hybridized with probe A, Southern blots of wild type DNA digested with BglI, BstXI, or EcoRI produce fragments of 15.7, 7.3, and 12.5 kb, respectively, whereas the presence of a targeted mu allele is indicated by fragments of 7.7, 6.6, and 14.3 kb, respectively. All 3 positive clones detected by the SpeI digest showed the expected BglI, BstXI, and EcoRI restriction fragments diagnostic of insertion of the neo cassette into the Cmu1 exon.

Generation of Mice Bearing the Mutated Mu Gene

The three targeted ES clones, designated number 264, 272, and 408, were thawed and injected into C57BL/6J blastocysts as described by Bradley (Bradley, A. (1987) in *Teratocarcinomas and Embryonic Stem Cells: a Practical Approach*. (E. J. Robertson, ed.) Oxford: IRL Press, p. 113-151). Injected blastocysts were transferred into the uteri of pseudopregnant females to generate chimeric mice representing a mixture of cells derived from the input ES cells and the host blastocyst. The extent of ES cell contribution to the chimera can be visually estimated by the amount of agouti coat coloration, derived from the ES cell line, on the black C57BL/6J background. Clones 272 and 408 produced only low percentage chimeras (i.e. low percentage of agouti pigmentation) but clone 264 produced high percentage male chimeras. These chimeras were bred with C57BL/6J females and agouti offspring were generated, indicative of germline transmission of the ES cell genome. Screening for the targeted mu gene was carried out by Southern blot analysis of BglI digested DNA from tail biopsies (as described above for analysis of ES cell DNA). Approximately 50% of the agouti offspring showed a hybridizing BglI band of 7.7 kb in addition to the wild type band of 15.7 kb, demonstrating a germline transmission of the targeted mu gene.

Analysis of Transgenic Mice for Functional Inactivation of Mu Gene

To determine whether the insertion of the neo cassette into Cmu1 has inactivated the Ig heavy chain gene, a clone 264 chimera was bred with a mouse homozygous for the JHD mutation, which inactivates heavy chain expression as a result of deletion of the JH gene segments (Chen et al, (1993) Immunol. 5: 647-656). Four agouti offspring were generated. Serum was obtained from these animals at the age of 1 month and assayed by ELISA for the presence of murine IgM. Two of the four offspring were completely lacking IgM (see Table 2). Genotyping of the four animals by Southern blot analysis of DNA from tail biopsies by BglI digestion and hybridization with probe A (see FIG. 1), and by StuI digestion and hybridization with a 475 bp EcoRI/StuI fragment (ibid.) demonstrated that the animals which fail to express serum IgM are those in which one allele of the heavy chain locus carries the JHD mutation, the other allele the Cmu1 mutation. Mice heterozygous for the JHD mutation display wild type levels of serum Ig. These data demonstrate that the Cmu1 mutation inactivates expression of the mu gene.

TABLE 2

| Mouse | Serum IgM (micrograms/ml) | Ig H chain genotype |
|---|---|---|
| 42 | <0.002 | CMD/JHD |
| 43 | 196 | +/JHD |
| 44 | <0.002 | CMD/JHD |
| 45 | 174 | +/JHD |
| 129 × BL6 F1 | 153 | +/+ |
| JHD | <0.002 | JHD/JHD |

Table 2 shows the levels of serum IgM, detected by ELISA, for mice carrying both the CMD and JHD mutations (CMD/JHD), for mice heterozygous for the JHD mutation (+/JHD), for wild type (129Svx C57BL/6J)F1 mice (+/+), and for B cell deficient mice homozygous for the JHD mutation (JHD/JHD).

Example 2

Generation of HCO12 Transgenic Mice for the Production of Anti-EGFR Human Antibodies The HCO12 Human Heavy Chain Transgene The HCO12 transgene was generated by coinjection of the 80 kb insert of pHC2 (Taylor et al., 1994, Int. Immunol., 6: 579-591) and the 25 kb insert of pVx6. The plasmid pVx6 was constructed as described below.

An 8.5 kb HindIII/SalI DNA fragment, comprising the germline human VH1-18 (DP-14) gene together with approximately 2.5 kb of 5' flanking, and 5 kb of 3' flanking genomic sequence was subcloned into the plasmid vector pSP72 (Promega, Madison, Wis.) to generate the plasmid p343.7.16. A 7 kb BamHI/HindIII DNA fragment, comprising the germline human VH5-51 (DP-73) gene together with approximately 5 kb of 5' flanking and 1 kb of 3' flanking genomic sequence, was cloned into the pBR322 based plasmid cloning vector pGP1f (Taylor et al. 1992, Nucleic Acids Res. 20: 6287-6295), to generate the plasmid p251f. A new cloning vector derived from pGP1f, pGP1k, was digested with EcoRV/BamHI, and ligated to a 10 kb EcoRV/BamHI DNA fragment, comprising the germline human VH3-23 (DP47) gene together with approximately 4 kb of 5' flanking and 5 kb of 3' flanking genomic sequence. The resulting plasmid, p112.2RR.7, was digested with BamHI/SalI and ligated with the 7 kb purified BamHI/SalI insert of p251f. The resulting plasmid, pVx4, was digested with XhoI and ligated with the 8.5 kb XhoI/SalI insert of p343.7.16.

A clone was obtained with the VH1-18 gene in the same orientation as the other two V genes. This clone, designated pVx6, was then digested with NotI and the purified 26 kb insert coinjected—together with the purified 80 kb NotI insert of pHC2 at a 1:1 molar ratio—into the pronuclei of one-half day (C57BL/6J×DBA/2J)F2 embryos as described by Hogan et al. (B. Hogan et al., Manipulating the Mouse Embryo, A Laboratory Manual, $2^{nd}$ edition, 1994, Cold Spring Harbor Laboratory Press, Plainview N.Y.). Three independent lines of transgenic mice comprising sequences from both Vx6 and HC2 were established from mice that developed from the injected embryos. These lines are designated (HCO12) 14881, (HCO12)15083, and (HCO12)15087. Each of the three lines were then bred with mice comprising the CMD mutation described in Example 1, the JKD mutation (Chen et al. 1993, EMBO J. 12: 811-820), and the (KCo5)9272 transgene (Fishwild et al. 1996, Nature Biotechnology 14: 845-851). The resulting mice express human immunoglobulin heavy and kappa light chain transgenes in a background homozygous for disruption of the endogenous mouse heavy and kappa light chain loci.

Example 3

Production of Human Monoclonal Antibodies Against EGFR

Two different strains of mice were used to generate EGFR reactive human monoclonal antibodies. Strain ((CMD)++; (JKD)++; (HCo7)11952+/++; (KCo5)9272+/++) (referred to herein as "HCO7 mice", and strain ((CMD)++; (JKD)++; (HCo12)15087+/++; (KCo5)9272+/++) (referred to herein as "HCO12 mice"). Each of these strains are homozygous for disruptions of the endogenous heavy chain (CMD) and kappa light chain (JKD) loci. Both strains also comprise a human kappa light chain transgene (HCo7), with individual animals either hemizygous or homozygous for insertion #11952. The two strains differ in the human heavy chain transgene used. Mice were hemizygous or homozygous for either the HCo7 or the HCo12 transgene. The CMD mutation is described above in Example 1. The generation of (HCo12)15087 mice is described in Example 2. The JKD mutation (Chen et al. 1993, EMBO J. 12: 811-820) and the (KCo5)9272 (Fishwild et al. 1996, *Nature Biotechnology* 14: 845-851) and (HCo7) 11952 mice, are described in U.S. Pat. Nos. 5,770,429 and 5,545,806 (Lonberg & Kay, Jun. 23, 1998).

The immunization schedule used is listed in Table 3 below. Mice were immunized twice with A 431 cells followed by soluble antigen in Ribi Adjuvant. The EGFR specific serum titer was determined by ELISA after the third immunization. Three different immunizations were done for the final boosts before the fusion. These included two or three sequential intravenous (iv) boosts via the tail vein with 10 μg of antigen in 50 μl PBS or two sequential intraperitoneal (i.p.) boosts with 25 μg soluble EGFR in Ribi adjuvant (see Table 3). The three mice that were used in the fusion were part of a larger cohort of mice that included both HCo7 and HCo12 genotypes.

TABEL 3

Immunization Schedule

| Mouse | A431 cells Day 1 | A431 cells Day 20 | ELISA Titer Day 30 | EGFR in Ribi ip Day 33 | ELISA Titer Day 43 | Fusion Day 46 | EGFR in RIBI ip Day 50 | Fusion Day 53 |
|---|---|---|---|---|---|---|---|---|
| 20241 | 2 × 10$^6$ | 1 × 10$^7$ | 0 | 25 μg | 4050 | | 25 μg | Ribi 2 × 25 μg*** |
| 20242 | 2 × 10$^6$ | 1 × 10$^7$ | 0 | 25 μg | 4050 | | 25 μg | 2 iv × 10 μg* |
| 20243 | 2 × 10$^6$ | 1 × 10$^7$ | 450 | 25 μg | 12150 | 3 iv × 10 μg* | | |

*EGFR in PBS (10 μg) iv on days −4, −3, and −2
**EGFR in PBS (10 μg) iv on day −4, and −3
***EGFR in Ribi (25 μg) i.p. on day −4 and −3

Immunization strategy used for the first two injections, 2-10×10$^6$ live A431 cells i.p., resulted in poor anti-EGFR titers (see Table 2). However, when these mice were given a third immunization with 25 μl g/mouse of soluble EGFR in Ribi adjuvant, serum titers increased more than 30 fold. These results clearly demonstrate that cells expressing a large amount of EGFR on the cell surface are very effective at initiating a primary immune response that then was greatly enhanced with only one dose of purified antigen in adjuvant.

The final boost before fusion for mouse 20243 was done as i.v. tail vein boosts with 10 μg soluble EGFR in PBS on days −4, −3, and −2. The Triton X-100 in the soluble EGFR caused an irritation to the tail of the mouse. Therefore, to reduce the possibility of irritation, mouse 20242 received only two i.v. vein boosts with soluble EGFR on days −4 and −3, and mouse 20241 received two i.p. immunizations on days −4 and −3 with 25 μg EGFR in Ribi adjuvant. The three fusions resulted in 46 human γ,κ-antigen positive hybridomas (see Table 4). Mouse 20241 alone, which received the i.p. boosts with adjuvant, produced 35 antigen specific Human Gamma Kappa antibodies.

TABLE 4

| Mouse | γκ+ | γ/κ + EGFR+ | γ1κ + EGFR+ | γ3κ + EGFR+ |
|---|---|---|---|---|
| 20243 | 120 | 14 | 13 | 1 |
| 20242 | 35 | 2 | 2 | 0 |
| 20241 | * | 30 | 28 | 2 |

Example 4

Hybridoma Preparation

The P3 X63 ag8.653 myeloma cell line (ATCC CRL 1580, lot F-15183) was used for the fusions. The original ATCC vial was thawed and expanded in culture. A seed stock of frozen vials was prepared from this expansion. A fresh vial of cells was thawed one to two weeks before the fusions.

High Glucose DMEM (Mediatech, Cellgro #10013) containing 10% FBS, Pennicillin-Streptomycin (Sigma, P-7539), and 5.5×10$^{-5}$M 2-mercaptoethanol (GibcoBRL, 21985-023) was used to culture A431 cells and myeloma cells. Additional media supplements were added to the Hybridoma growth media, which included: 3% Origin-Hybridoma Cloning Factor (Igen, 21001), OPI supplement (Sigma, 0-5003), 1.1×10$^{-3}$ M Oxalo acetic acid, 4.5×10$^{-4}$ M sodium Pyruvate, and 24 international units/L bovine Insulin, HAT (Sigma, H 0262) 1.0×10$^{-4}$ M Hypoxanthine, 4.0×10$^{-7}$ M Aminopterin, 1.6×10$^{-5}$M Thymidine, or HT (Sigma, H0137) 1.0×10$^{-4}$ M Hypoxanthine, 1.6×10$^{-5}$M Thymidine.

Characterized Fetal bovine serum (SH30071 lot #s AJE10321 and AGH6843) was obtained from Hyclone, Logan, Utah. Serum Free medium contained DMEM, antibiotics and 2-mercaptoethanol only.

Spleens from all three mice were normal in size and yielded from 2×10$^7$ to 1×10$^8$ splenocytes. The splenocytes were fused.

The initial ELISA screen for human IgG κ antibodies was performed 7-10 days post fusion. Human IgG, κ positive wells were screened on soluble EGFR coated ELISA plates. Antigen positive hybridomas were transferred to 24 well plates and eventually to tissue culture flasks. EGFR specific hybridomas were subcloned by limiting dilution to assure monoclonality. Antigen positive hybridomas were preserved at several stages in the development process by freezing cells in DMEM 10% FBS plus 10% DMSO (Sigma, D2650) or in Origen Freeze Medium (Igen, #210002). Cells were stored at −80° C. or in LN$_2$.

Initial EGFR specific hybridomas were subsequently evaluated for epitope specificity and their ability to block the binding of EGF to the EGFR receptor. Mouse monoclonal anti-EGFR antibodies 225 and 528 have previously been shown to bind to EGFR, block binding of EGF to EGFR and to be anti-cancer immunotherapeutic agents in animal and human studies. Therefore these antibodies were used, in addition to a non-blocking antibody, in a competitive ELISA format to identify human antibodies that have immunotherapeutic characteristics.

Example 5

Binding Affinity

Binding affinity for hybridoma 2F8 was determined using BIAcore 3000 (Biacore, Upsula, Sweden). EGFR purified from A431 cells purchased from Sigma was immobilized on a CM5 chip according to the manufacturer's instructions. Antibody 2F8 had an equilibrium association constant ($K_A$) of $5.47 (\pm 0.52) \times 10^8$ $M^{-1}$.

Example 6

Competitive ELISA Assays

Figure 2:
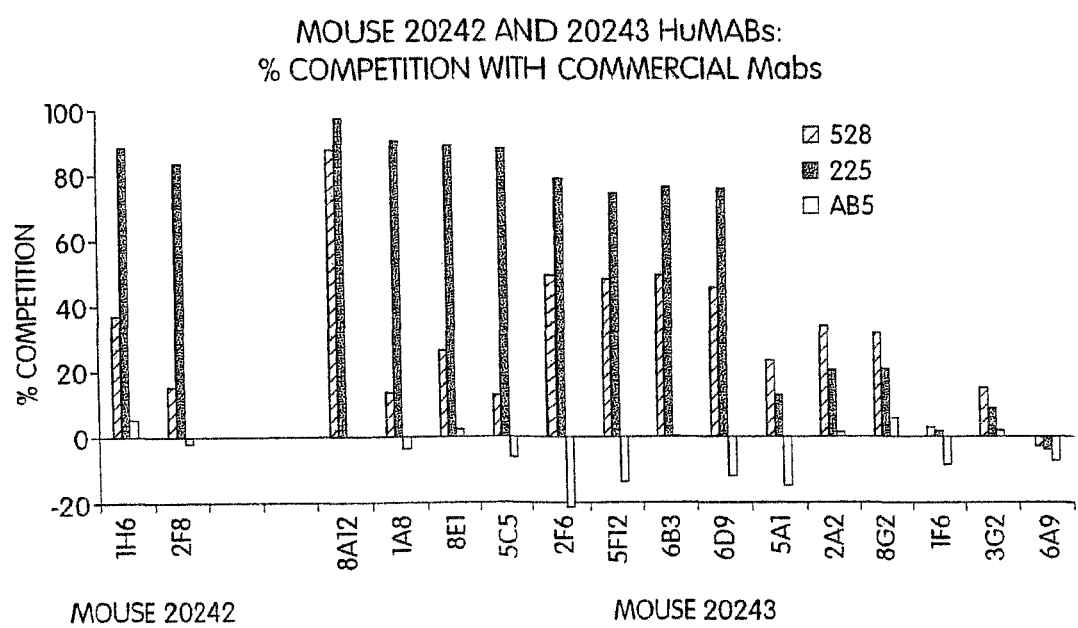
FIG. 2 is a graph showing competitive ELISA with human antibody supernatants from mouse 20242 and 20243 versus murine monoclonal anti-EGFR MAbs 225, 528, and AB5.

Competitive ELISA assays were used as the initial qualifying assay as soon as antigen positive hybridomas were established in 24 well plates. In general, strong competition (80-100%) indicates that an antibody binds to the same epitope or to a region of the antigen in close proximity to the competing antibody. Weaker competition of less than 50% indicates that the antibody and its competitor bind to regions of the antigen not in close proximity. Initial assays were done with supernatants from uncloned hybridomas many of which contained more than one hybridoma per well. Later assays were done with subclones of the original wells. FIGS. 1 and 2 show (the data in FIGS. 1 and 2 are arranged based on degree of competition with MAb 225) that even with crude cell culture supernatants, antibodies can be identified that bind to similar or identical epitopes as the 225 and 528 antibodies. Also evident in this experiment is the different distribution in competitive binding patterns of antibodies derived from mouse 20241 or from mouse 20242 and 20243. For example, the first seven antibodies from the #20241 mouse (FIG. 1) compete strongly with both MAb 225 and 528. The remainder of the antibodies from 20241 competed moderately or weakly with the 225 and 528 antibodies. Five antibodies (1H6, 2F8, 1A8, 5C5, and 8E1) from the 20242 and 20243 mice showed strong competition with antibody 225 and no competition or weak competition from MAb 528 (FIG. 2). Antibodies 2F6, 8A12, 5F12, 6B3, and 6D9 from mouse 20242 and 20243 competed with both MAb 225 and 528, although the competition was stronger against the 225 antibody. Other antibodies from these mice did not compete or were weakly competitive with the commercial MAbs.

Figure 3:
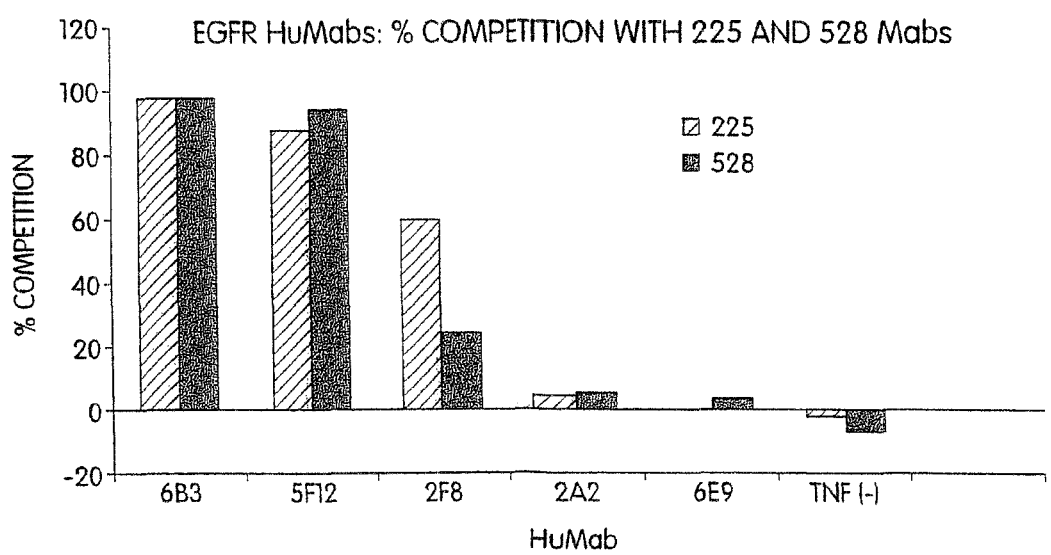
FIG. 3 is a graph showing competitive ELISA with purified human antibodies versus murine monoclonal anti-EGFR MAbs 225 and 528.
Figure 4A:
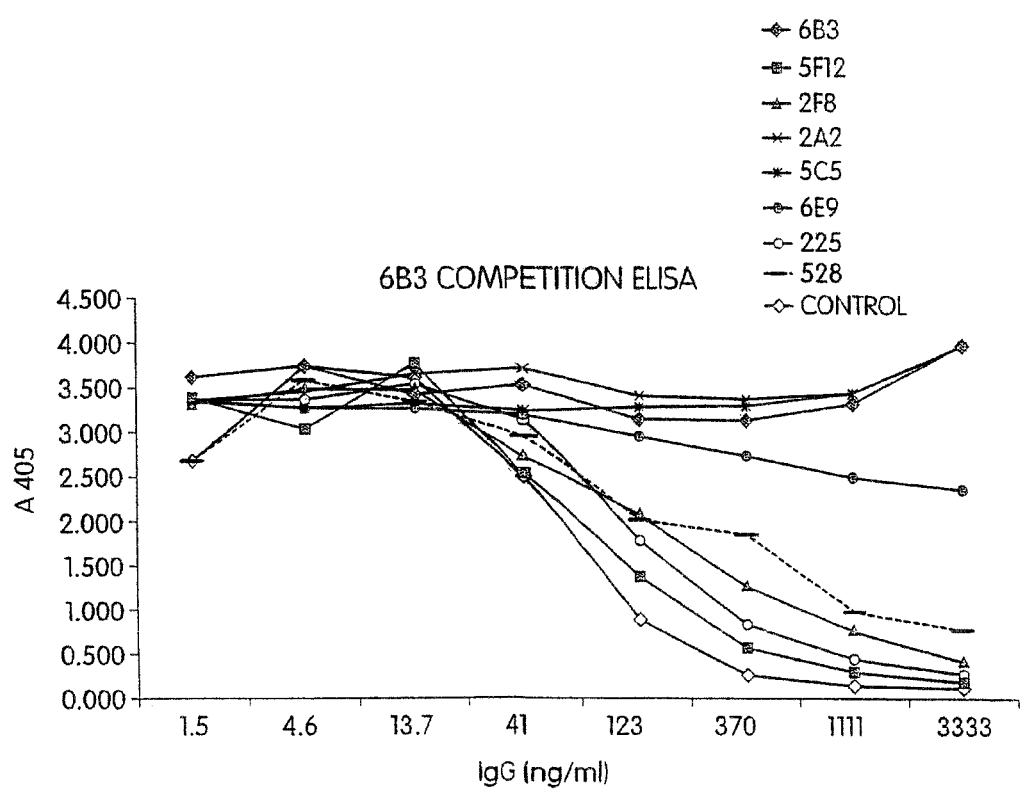
FIGS. 4A, 4B, 4C, and 4D are graphs showing competitive ELISA with HuMabs (A) 6B3, (B) 5F12, (C) 2F8, and (D) 2A2.
Figure 4B:
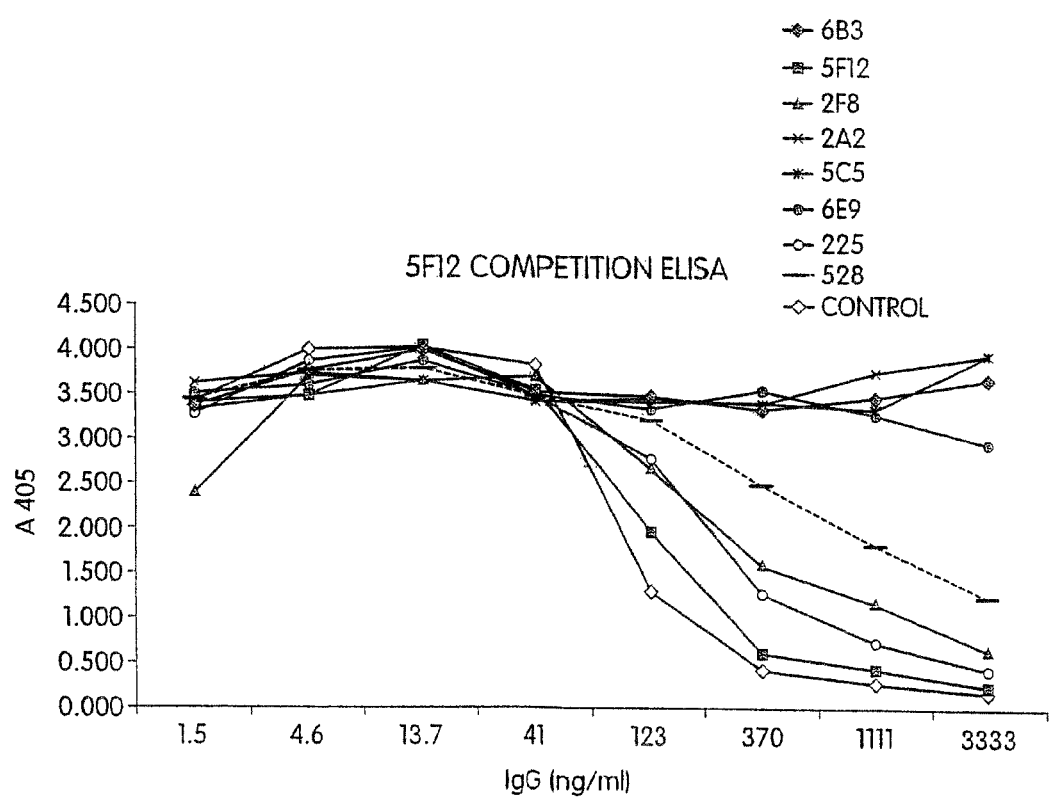
Figure 4C:
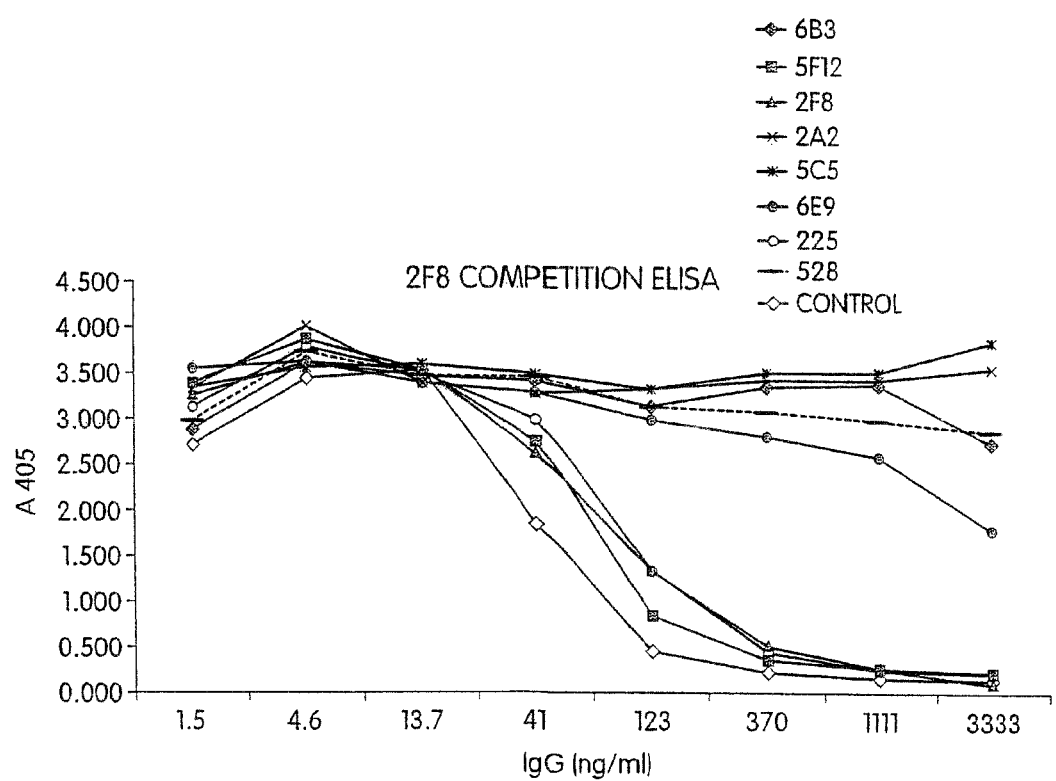
Figure 4D:
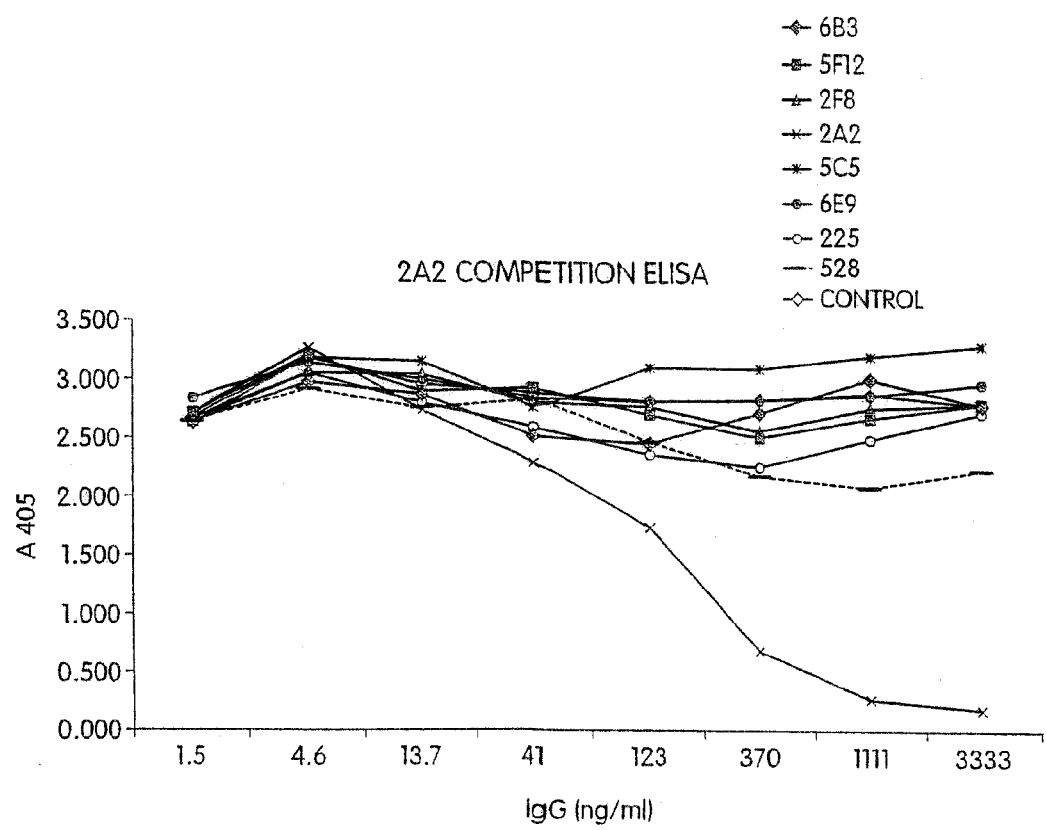

These initial competitive ELISA results were verified with purified antibodies produced by sub-cloned cells. FIGS. 3 and 4 show that antibodies 5F12 and 6B3 compete strongly with both MAb 225 and 528 and also demonstrate reciprocal competition with each other. This data indicate that these antibodies bind to the same epitope or to a region of the EGFR molecule in close proximity to the 225 or 528 binding site. Antibody 2F8 competes moderately with MAb 225 and does not significantly compete with antibody 528 (FIGS. 3 and 4). However, antibody 2F8, 6B3 and 5F12 show strong cross competition. This data suggests that antibody 2F8 is binding to a separate epitope from the 225 and 528 antibodies and binds to a region of the EGFR receptor that is adjacent to or overlaps with the epitope to which HuMabs 6B3 and 5F12 bind. Antibodies 2A2 and 6E9 do not compete with either MAb and bind to EGFR epitopes unrelated to the binding sites of the 225 and 528 MAbs (FIGS. 3 and 4).

Example 7

EGF/EGFR Blocking Assays

Figure 5A:
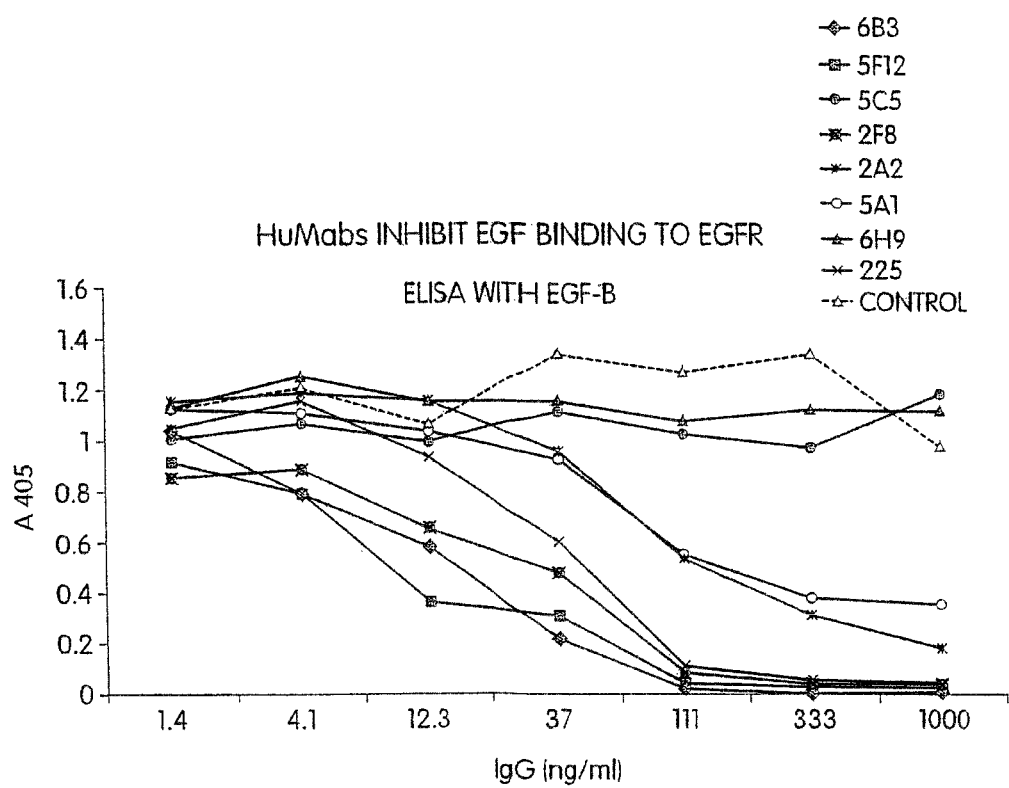
FIGS. 5A and 5B are graphs showing inhibition of EGF-biotin binding to EGFR by anti-EGFR HuMabs and murine MAbs (ELISA format).
Figure 5B:
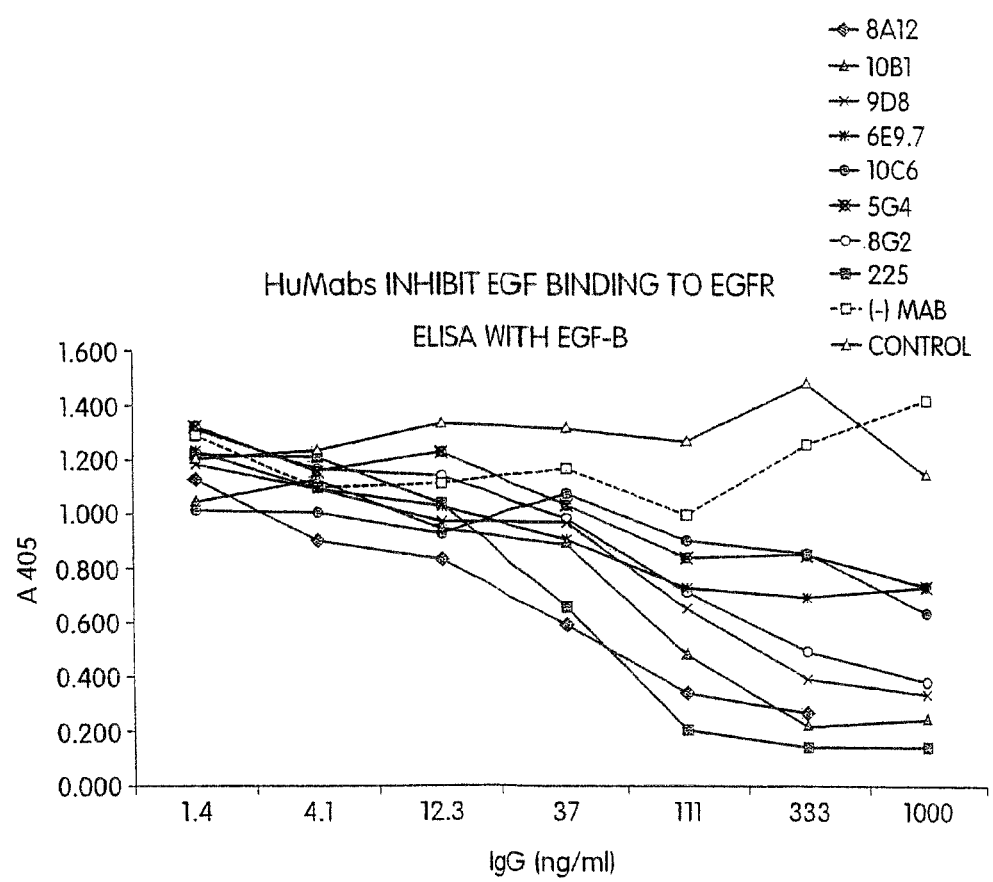
Figure 6:
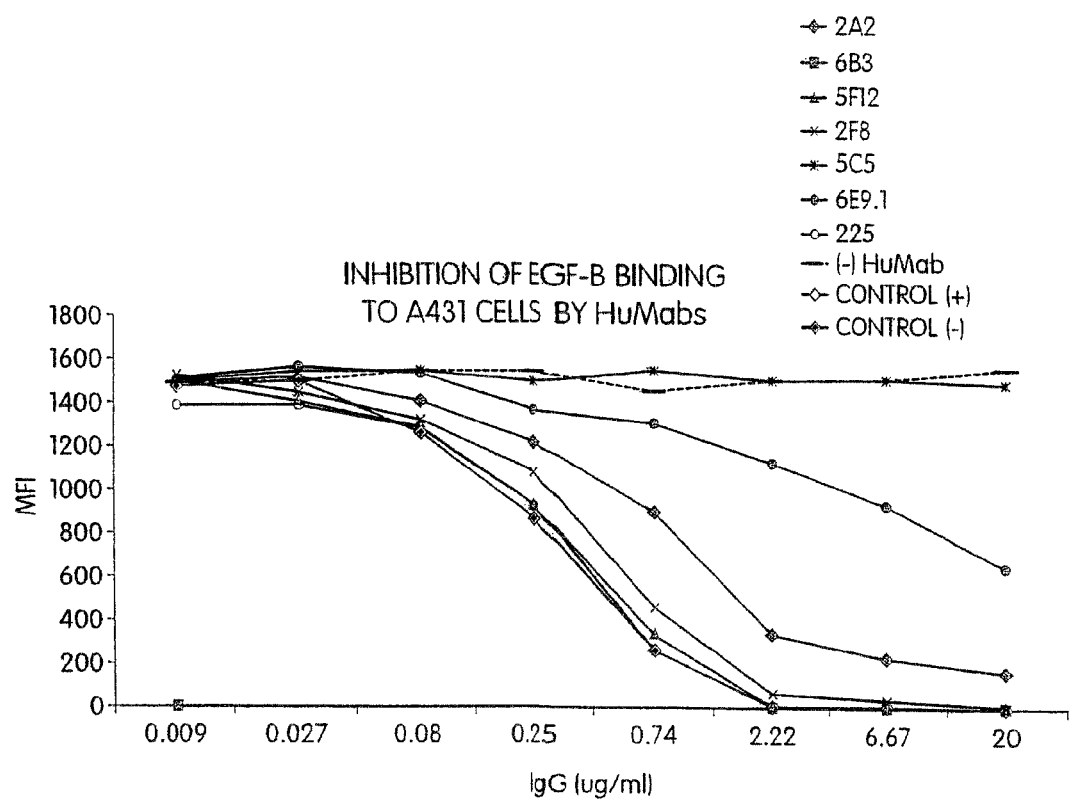
FIG. 6 is a graph showing inhibition of EGF-biotin binding to EGFR on A431 cells by anti-EGFR HuMabs and murine MAbs.
Figure 7:
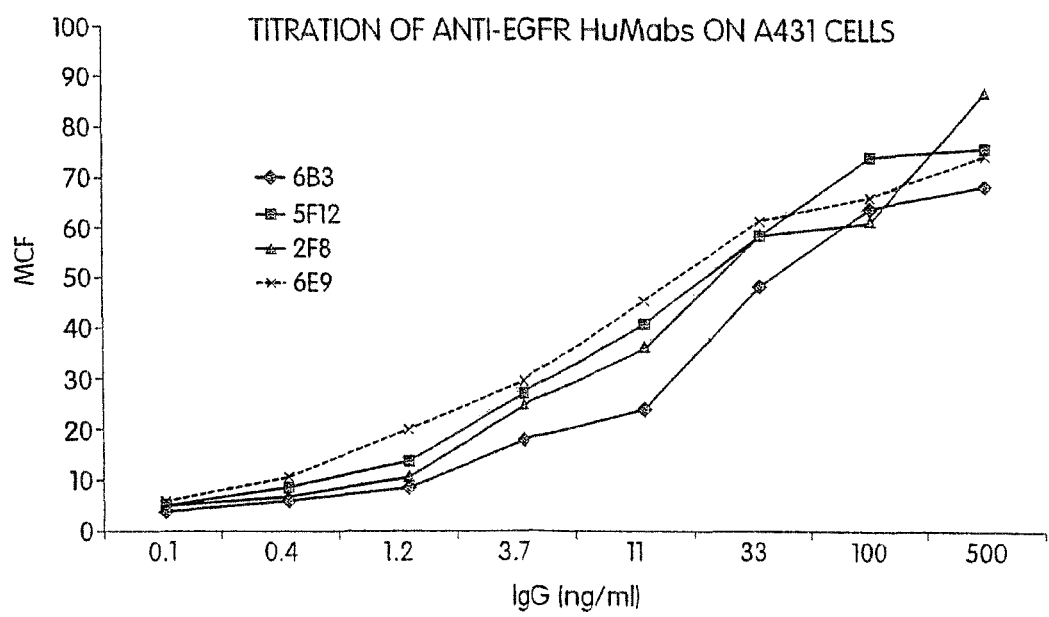
FIG. 7 is a graph showing titration of anti-EGFR HuMabs on A431 cells.

Antigen positive subclones were further evaluated in EGF/EGFR blocking assays. These assays included subclones of antibodies that compete strongly with MAb 225 and/or 528, as well as, antibodies that are weak or non competitive with 225 or 528. Several antibodies were expanded in culture medium and purified by protein A chromatography. FIGS. 5 and 6 show that antibodies 2F8, 5F12, and 6B3, which are moderate to strong competitors of the 225 antibody in ELISA, are strong blockers of EGF binding to EGFR. This is evident in assays done in ELISA format or by FACS on human A431 epidermoid cancer cells. In both assays, the human antibodies were as good as or better than MAb 225. Antibodies 2F8, 5F12, 6B3, and 6E9 also have similar binding characteristics on the surface of A431 cells (FIG. 7).

The in vitro EGF/EGFR blocking and ELISA competition studies demonstrated that the 2F8, 5F12, and 6B3 antibodies have similar properties to other anti-EGFR murine and human antibodies that have been shown to be immunotherapeutic agents (Sato, et al. (1983) Mol. Biol. Med. 511-529; Gill, et al. (1984) J. of Biol. Chem. 259(12):7755-7760). The 2F8 antibody was equivalent to or better than the 6B3 and 5F12 antibodies overall in the various evaluations.

Example 8

Figure 8:
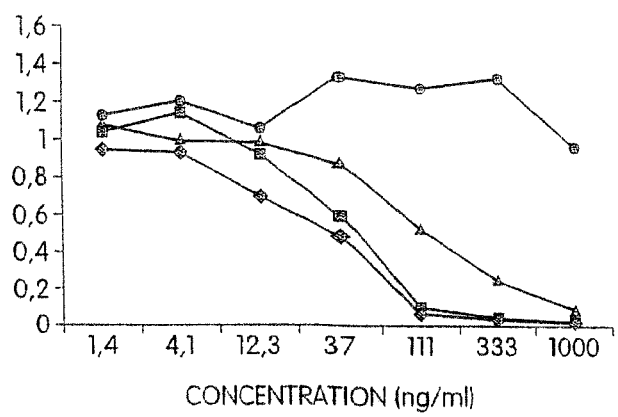
FIG. 8 is a graph showing the ability of 2F8 to inhibit the binding of EGF binding to purified and native EGFR. The effect of 2F8 (diamonds), murine 225 (squares), EGF (triangles) or human IgG1 kappa isotype control (bullets) is measured on the binding of EGF-biotin to immobilized EGFR. As depicted in FIG. 8, 2F8 is able to inhibit EGF-biotin binding with an IC50 of 17 nM, significantly lower than 225 (IC50 of 30 nM).

Inhibition of EGF/TGF-α Binding to the EGF Receptor Using Human Monoclonal Antibodies to the EGF Receptor Inhibition studies were performed on A431 cells using flow cytometry, ELISA, and inhibition of ligand-induced autophosphorylation. Murine MAbs 225 or 525 were used as positive controls. An irrelevant human IgG isotype control, was used as an isotype control. A single human antibody, 2F8, was chosen for all the further studies. This antibody is also referred to herein as "Humax-EGFR™". FIG. 8 shows the EGF blocking capacity of 2F8 in a concentration dependent manner. 2F8 and m225 block to the same extent while the blocking capacity of EGF is less.

Figure 9:
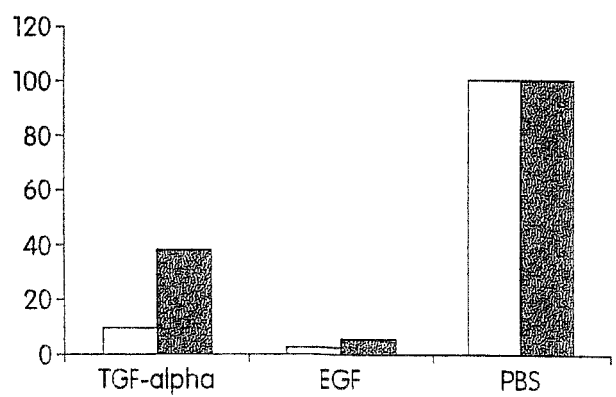
FIG. 9 is a bar graph showing the ability of 2F8 to inhibit the binding of EGF and TGF-α to A431 cells. A431 cells are derived from an ovarian epidermoid carcinoma and express in excess of $1 \times 10^6$ EGFR molecules on their cell surface. Inhibition of 2F8-binding to A431 cells was determined using flow cytometer analysis. Cells were pre-incubated with either 5 (open bars) or 50 µg/ml (closed bars) ligand before adding 2F8. Binding of antibody without ligand (PBS group) was designated as 100%. As shown, EGF and TGF-α binding to A431 cells is efficiently blocked by 2F8. These results indicate that 2F8 binds close to, or at the same site, on EGFR as the ligands.

FIG. 9 further shows the blocking capacity of 2F8 in that it efficiently inhibits the binding of EGF and TGF-α to A431 cells (cells derived from an ovarian epidermoid carcinoma and express in excess of $1 \times 10^6$ EGFR molecules on their cell surface). Inhibition of 2F8-binding to A431 cells was determined using flow cytometer analysis. Cells were pre-incubated with either 5 (open bars) or 50 µg/ml (closed bars) ligand before adding 2F8. Binding of antibody without ligand (PBS group) was designated as 100%. These results indicate that 2F8 binds close to, or at the same site, on EGFR as the ligands.

Example 9

Figure 10A:
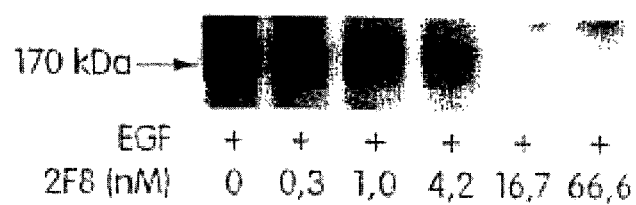
FIGS. 10A and 10B show the effect of monoclonal anti EGFR on autophosphorylation of A431 cells. Serum deprived subconfluent A431 cells were treated with different antibodies (10 µg/ml) as indicated in the methods, stimulated with either EGF (A) or TGF-α (B), and extracted. The EGFR phosphorylation was analyzed by SDS-PAGE and immunoblotting with antiphosphotyrosine antibodies.
Figure 10B:
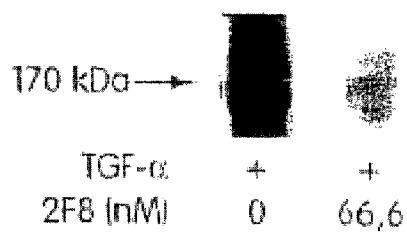
Figure 11A:
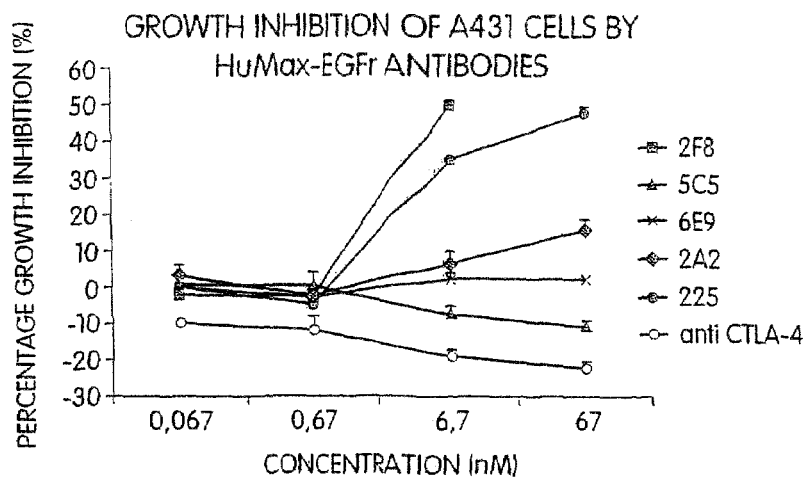
FIGS. 11A, 11B, and 11C are graphs showing growth inhibition of EGFR-expressing tumor cell lines by anti-EGFR human antibodies. The EGFR-expressing tumor cell lines A431 (A), HN5 (B) and MDA-MB-468 (C) were incubated with various concentrations of HuMab 2F8 (squares), 5C5 (triangles), 6E9 (crosses), 2A2 (diamonds) antibody negative control anti-CTLA4 (open circles), antibody positive control 225 (closed circles) or with medium only (control) for seven (7) days. Thereafter, cell growth was evaluated using crystal violet staining of fixed cells. The percentage growth inhibition was calculated as the amount of protein left after seven (7) days incubation compared to the amount of protein present in the medium only control. The data represent triplicate measurements, and are representative of three experiments performed on different days.
Figure 11B:
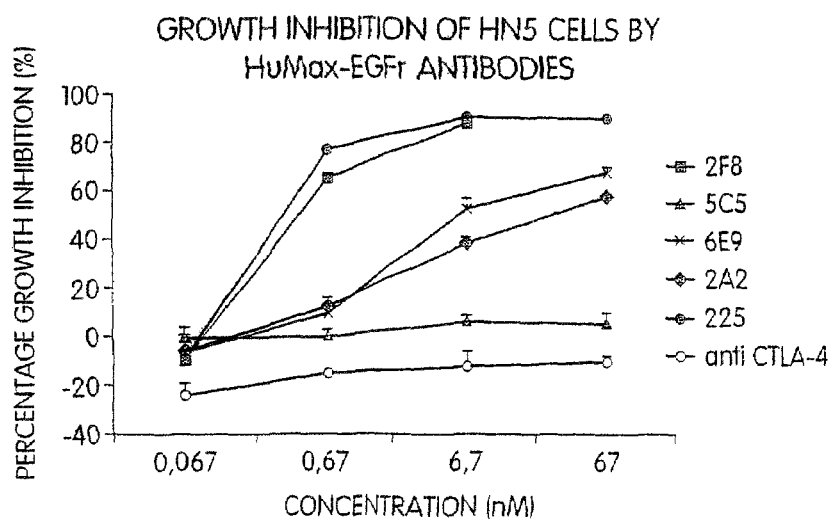
Figure 11C:
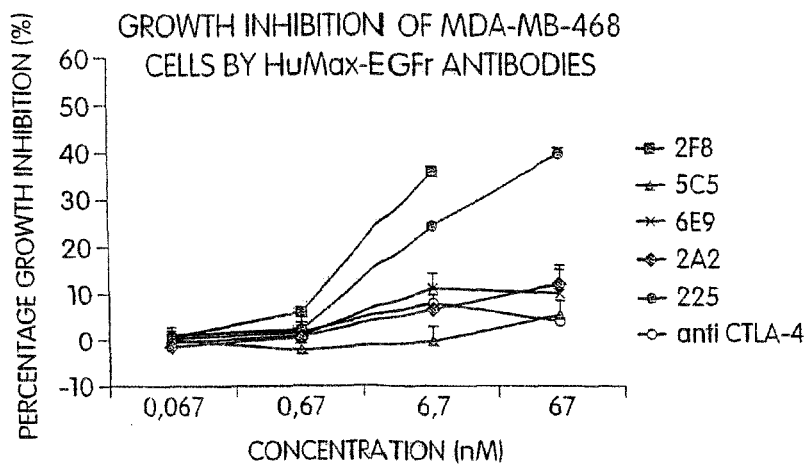
Figure 12:
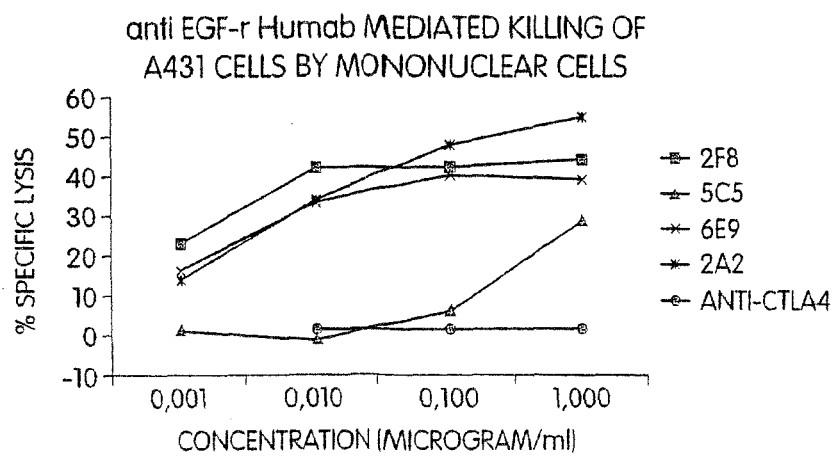
FIG. 12 is a graph showing human PMN mediated antibody dependent cellular cytotoxicity. PMN were isolated as described. $^{51}$Chromium labeled A431 cells were plated in 96 wells flat bottom plates. PMN were added in effector:target ratio 100:1 and antibodies were added in different concentrations. After overnight incubation, the $^{51}$Cr release was measured.
Figure 13:
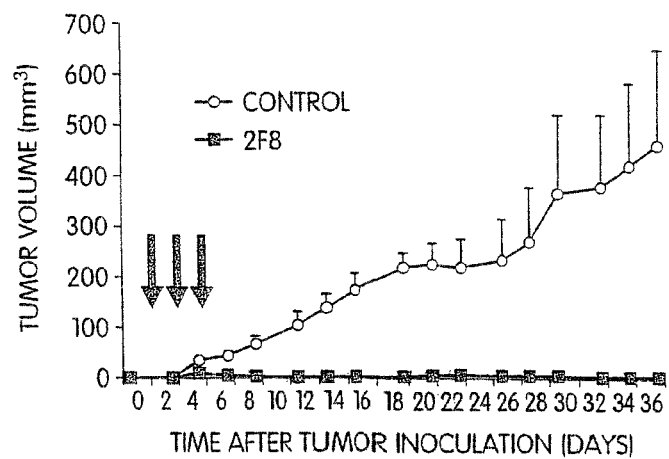
FIG. 13 is a graph showing the prevention of tumor formation by HuMab 2F8 in an athymic murine model. Groups of six (6) mice were injected subcutaneously in the flank with $3 \times 10^6$ tumor cells in 200 µl PBS at day zero (0). Subsequently, mice were injected i.p. on days 1 (75 µg/200 µl), 3 (25 µg/200 µl), and 5 (25 µg/200 µl) (arrows) with either HuMab 2F8 (closed squares) i.p. of human IgG1-κ MAb as a control (open circles). The data are presented as mean tumor volume+SEM, and are representative of 3 individual experiments, yielding similar results.

Inhibition of Tumor Cell Activation Using Human Monoclonal Antibodies to the EGF Receptor To evaluate the ability of 2F8 to inhibit tumor cell activation, the effect of 2F8 on EGF-triggered cellular responses, such as activation of the intrinsic tyrosine kinase activity and concomitant cell proliferation, was examined. One of the first events after EGF or TGF-α binding to the EGFR is the induction of autophosphorylation of the receptor. Incubation of EGF with A431 cells results in tyrosine phosphorylation of the EGFR ($M_r$ 170,000) (FIG. 10A). While 2F8 did not activate the receptor kinase activity by itself, the antibody blocked EGF-triggered EGFR tyrosine phosphorylation in a dose-dependent manner with a complete inhibition at a concentration of 16.6 nM (antibody:EGF molar ratio, 20:1, FIG. 10A). Cells were treated with antibody and TGF-α showed that tyrosine phosphorylation was fully blocked by 2F8 at a concentration of 66 nM (antibody:TGF-α molar ratio, 7, 3:1, FIG. 10B).

Figure 14:
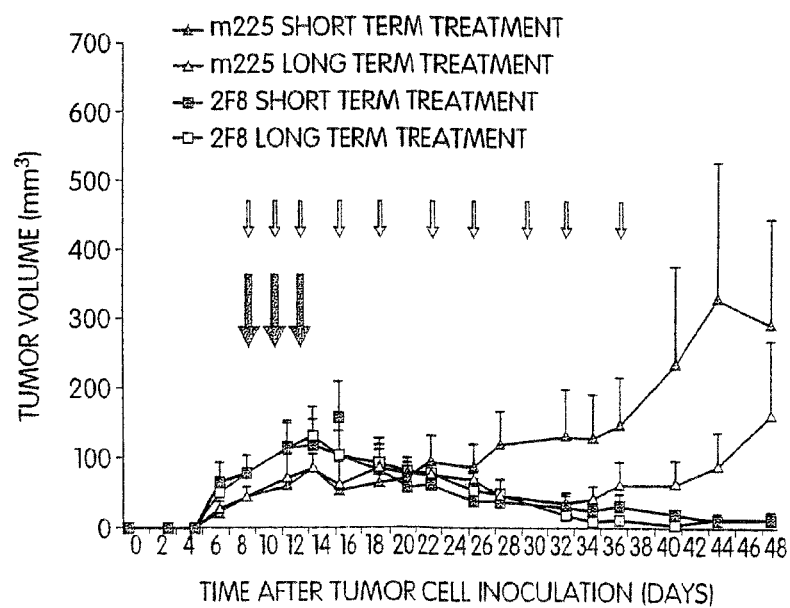
FIG. 14 is a graph showing the eradication of established A431 tumor xenografts by HuMab 2F8 in comparison to murine anti-EGFR MAb (m225). Mice were injected subcutaneously in the flank with $3 \times 10^6$ tumor cells in 200 µl PBS on day zero (0). At day 10, mice were randomly allocated to treatment groups and treated on days 12 (75 µg/200 µl), 14 (25 µg/200 µl), and 16 (25 µg/200 µl) (arrows) with HuMab 2F8 (closed squares, 2F8 short-term) or with murine anti-EGFR MAb 225 (closed triangles, m225 short-term). Furthermore, groups were included receiving 75 µg/200 µl HuMab 2F8 or m225 on day 12, continued by 25 µg/200 µl HuMab 2F8 or m225 on days 14, 16, 19, 22, 26, 29, 33, 36, and 40 (open squares, 2F8 long-term; open triangles, m225 long-term). The data are presented as mean tumor volume+SEM, and are representative of 3 individual experiments, yielding similar results. Black arrows indicate treatment days for the short-term treatment, open arrows indicate treatment days for the long-term treatment.

Engagement of EGF/TGF-α with the receptor results in cell activation which is reflected in cell proliferation. Therefore the inhibitory effect of 2F8 on growth of tumor cells (A431, MDA-MD-468 and HN5 cells) was evaluated. The experiments were carried out in the absence of exogenous EGF. Mouse antibodies were used as a comparison. Humax-EGFR inhibited the growth of A431 cells in a concentration dependent manner with a maximal inhibition of 50%, a level similar to that obtained with mouse antibody 225 (FIG. 14). The control antibody had no effect on the cell proliferation (FIG. 14). Growth inhibition was also obtained with two other cell lines at similar levels (HN5 and MDA-MB468, panels B and C). As no exogenous EGF was added to the culture, these results indicate the ability of 2F8 to block autocrine stimulation and thus to inhibit autocrine EGF/TGF-α induced tumor cell activation.

Example 10

Human Monoclonal Antibodies to the EGF Receptor Induce ADCC

ADCC is a potent immune effector mechanism triggered by the recognition of tumor cells by antibodies. To evaluate the ability of human PMN cells to kill A431 cells in the presence of 2F8, A431 cells were loaded with $^{51}$Cr and subsequently incubated with antibody and effector cells (PMN) overnight. After incubation, chromium release was measured. As shown in FIG. 14, 2F8 is capable of inducing ADCC against A431 cells using human PMN. 2F8 is capable of mediating PMN-induced lysis of 45% of the A431 target cells, which is higher then observed with the MAb 425 (FIG. 14).

Importantly, while capable of recruiting immune effector cells and inducing ADCC, 2F8 is unable to induce complement-mediated lysis of tumor cells.

Example 11

Human Monoclonal Antibodies to the EGF Receptor Prevent Tumor Formation

To show the ability of HuMab 2F8 to prevent tumor formation in an athymic murine model, groups of six (6) mice were injected subcutaneously in the flank with $3\times10^6$ tumor cells in 200 μl PBS at day zero (0). Subsequently, mice were injected i.p. on days 1 (75 μg/200 μl), 3 (25 μg/200 μl), and 5 (25 μg/200 μl) (arrows) with either HuMab 2F8 (closed squares) i.p. of human IgG1-K MAb as a control (open circles) (FIG. 14). The data are presented as mean tumor volume+SEM, and are representative of 3 individual experiments, yielding similar results.

Eradication of established A431 tumor xenografts by HuMab 2F8 in comparison to m225 is shown in FIG. 14. Mice were injected subcutaneously in the flank with $3\times10^6$ tumor cells in 200 μl PBS on day zero (0). At day 10, mice were randomly allocated to treatment groups and treated on days 12 (75 μg/200 μl), 14 (25 μg/200 μl), and 16 (25 μg/200 μl) (arrows) with HuMab 2F8 (closed squares, 2F8 short-term) or with murine anti-EGFR MAb m225 (closed triangles, m225 short-term). Furthermore, groups were included receiving 75 μg/200 μl HuMab 2F8 or m225 on day 12, continued by 25 μg/200 μl HuMab 2F8 or m225 on days 14, 16, 19, 22, 26, 29, 33, 36, and 40 (open squares, 2F8 long-term; open triangles, m225 long-term). The data are presented as mean tumor volume+SEM, and are representative of 3 individual experiments, yielding similar results. Black arrows indicate treatment days for the short-term treatment, open arrows indicate treatment days for the long-term treatment.

EQUIVALENTS

Those skilled in the art will recognize, or be able to ascertain using no more than routine experimentation, many equivalents of the specific embodiments of the invention described herein. Such equivalents are intended to be encompassed by the following claims.

INCORPORATION BY REFERENCE

All patents, pending patent applications and other publications cited herein are hereby incorporated by reference in their entirety. Any combination of the embodiments disclosed in the dependent claims are contemplated to be within the scope of the invention.

We claim:

1. A method of treating a disease mediated by over expression of EGFR, comprising administering to a subject having the disease an antibody which binds to human EGFR in an amount effective to treat the disease, wherein the disease is cancer, and wherein the antibody is selected from the group consisting of:
   (a) a human or humanized monoclonal antibody which binds the same epitope on human EGFR recognized by an antibody comprising heavy and light chain variable regions comprising the amino acid sequences set forth in SEQ ID NOs: 2 and 4, respectively; and
   (b) a human or humanized monoclonal antibody which binds to human EGFR, competes with antibody 225, but does not compete with antibody 528.

2. The method of claim 1, wherein the antibody binds the same epitope on human EGFR recognized by an antibody comprising heavy and light chain variable regions comprising the amino acid sequences set forth in SEQ ID NOs: 2 and 4, respectively.

3. The method of claim 1, wherein the antibody binds to human EGFR, competes with antibody 225, but does not compete with antibody 528.

4. The method of claim 1, wherein the antibody comprises a heavy or light chain variable region comprising the amino acid sequence set forth in SEQ ID NO: 2 or 4, respectively.

5. The method of claim 1, wherein the antibody comprises: (a) a heavy chain variable region comprising CDR1, CDR2, and CDR3 sequences comprising the amino acid sequences set forth in SEQ ID NOs:5, 6, and 7, respectively; and (b) a light chain variable region comprising CDR1, CDR2, and CDR3 sequences comprising the amino acid sequences set forth in SEQ ID NO:8, 9, and 10, respectively, wherein the antibody binds to human EGFR.

6. The method of claim 1, wherein the antibody comprises a heavy or light chain variable region encoded by the nucleotide sequence as set forth in SEQ ID NO:1 or SEQ ID NO:3, respectively.

7. The method of claim 1, wherein the antibody is a human IgG1 antibody.

8. The method of claim 1, wherein the antibody is an Fab fragment or a single chain antibody.

9. The method of claim 1, wherein the antibody is produced by a hybridoma which includes a B cell obtained from a transgenic non-human animal having a genome comprising a human heavy chain transgene and a human light chain transgene fused to an immortalized cell.

10. The method of claim 1, wherein the antibody is produced by a transfectoma comprising nucleic acids encoding a human heavy chain and a human light chain.

11. The method of claim 1, wherein the antibody binds to human EGFR with an equilibrium association constant ($K_A$) of at least $10^8$ $M^{-1}$.

12. The method of claim 1, wherein the antibody blocks EGFR ligand binding to human EGFR by at least 50% in an enzyme-linked immunosorbent assay (ELISA).

13. The method of claim 1, wherein the antibody binds to cells expressing EGFR and induces lysis (ADCC) of the cells in the presence of human effector cells.

14. The method of claim 1, wherein the antibody binds to cells expressing EGFR, but does not induce complement-mediated lysis of the cells in vivo.

15. The method of claim 1, wherein the antibody binds to EGFR and inhibits EGF- or TCF-α-induced autophosphorylation of EGFR.

16. The method of claim 1, wherein the cancer is selected from the group consisting of bladder cancer, breast cancer, colon cancer, ovarian cancer, prostate cancer, and renal cancer.

17. The method of claim 1, wherein the cancer is selected from the group consisting of uterine/cervical cancer, esophageal cancer, pancreatic cancer, colorectal cancer, head and neck cancer, non-small cell lung cancer and stomach cancer.

18. The method of claim 17, wherein the cancer is colorectal cancer or head and neck cancer.

19. The method of claim 1, wherein the antibody is conjugated to a second antibody, or fragment thereof, which binds a Fc receptor.

20. The method of claim 1, wherein the antibody is conjugated to a cytotoxin.

21. The method of claim 1, further comprising the co-administration of a therapeutic agent.

22. The method of claim 21, wherein the therapeutic agent is selected from the group consisting of doxorubicin (adriamycin), cisplatin bleomycin sulfate, carmustine, chlorambucil, and cyclophosphamide hydroxyurea.

23. The method of claim 1, comprising administration of one or more further therapies selected from the group consisting of chemotherapeutic agents, immunosuppressive agents, anti-inflammatory agents, anti-psoriasis agents, radiation therapy, hyperthermia, transplantation, surgery, and phototherapy.

* * * * *